United States Patent
Albert et al.

(10) Patent No.: US 9,115,134 B2
(45) Date of Patent: Aug. 25, 2015

(54) 6-TRIAZOLOPYRIDAZINE SULFANYL BENZOTHIAZOLE DERIVATIVES AS MET INHIBITORS

(71) Applicant: SANOFI, Paris (FR)

(72) Inventors: Eva Albert, Paris (FR); Eric Bacque, Paris (FR); Conception Nemecek, Paris (FR); Antonio Ugolini, Paris (FR); Sylvie Wentzler, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 14/011,110

(22) Filed: Aug. 27, 2013

(65) Prior Publication Data

US 2014/0005189 A1    Jan. 2, 2014

Related U.S. Application Data

(60) Division of application No. 12/693,736, filed on Jan. 26, 2010, now Pat. No. 8,546,393, which is a continuation of application No. PCT/FR2008/001172, filed on Aug. 6, 2008.

(30) Foreign Application Priority Data

Aug. 9, 2007    (FR) ..................................... 07 05789
Apr. 2, 2008    (FR) ..................................... 08 01819

(51) Int. Cl.
C07D 487/04    (2006.01)
A61K 31/5025    (2006.01)

(52) U.S. Cl.
CPC .......... *C07D 487/04* (2013.01); *A61K 31/5025* (2013.01)

(58) Field of Classification Search
CPC ........................... C07D 487/04; A61K 31/5025
See application file for complete search history.

(56) References Cited

U.S. PATENT DOCUMENTS

2010/0298315 A1    11/2010    Albert et al.

FOREIGN PATENT DOCUMENTS

| FR | 2 499 995 | 8/1982 |
| WO | WO 03/028721 A2 | 4/2003 |
| WO | WO-2007/064797 A2 | 6/2007 |
| WO | WO-2007/064797 A3 | 6/2007 |
| WO | WO 2007/075567 A1 | 7/2007 |
| WO | WO 2007/138472 A2 | 12/2007 |
| WO | WO 2008/008539 | 1/2008 |
| WO | WO 2008/051808 | 5/2008 |

OTHER PUBLICATIONS

Cancer definition in MedicineNet.com—(2004).*
Stomach cancer—Mayoclinic.com—Apr. 9, 2011.*
GastricMALTLymphoma—LymphomaAssociation—2011.*
Adult Brain Tumors Treatment, National Cancer Institute, pp. 1-21 (Jan. 24, 2013).*
Types of Brain Cancer at http://www.cancercenter.com/brain-cancer/types-of-brain-cancer.cfm (Mar. 12, 2013).*
Colorectal Cancer at cancer.net (published Sep. 2012), pp. 1-2.*
"Types of Breast Cancer", published in breastcancer.org (Sep. 30, 2012); p. 1.*
Graveel et al. Cold Spring Harb Perspect Biol 2013;5:a009209.*
Shah et al., PloS ONE 8(3):e54014; p. 1-9 (Mar. 2013)).*
Marketwatch—Jan. 16, 2014.*
Wen et al., Neuro-Oncology 13 (4):437-446, 2011).*
Schafer et al. Drug discovery Today 2008, 13 (21/22), 913-916.*
Luo et al. (Cell 136, Mar. 6, 2009; 823-837).*
Manning et al. (Science 298, p. 1912-1934 (2002)).*
Anonymous, "6-Benzothiazolethiol, 2-Amino-(9CI) Product Description", [on-line] 2007, http://www.chemicalbook.com/ChemicalProductProperty_EN_CB81296260.htm.
Berge S.M. et al., "Pharmaceutical Salts", Journal of Pharmaceutical Sciences 66(1):1-19 (Jan. 1977).
Das J. et al., "2-Aminothiazole as a Novel Kinase Inhibitor Template. Structure-Activity Relationship Studies Toward the Discovery of N-(2-Chloro-6-Methylphenyl)-2-[[6-[4-(2-Hydroxyethyl)-1-Piperazinyl)]-2-Methyl-4-Pyrimidinyl] Amino)]-1,3-Thiazole-5-Carboxamide (Dasatinib, BMS-354825) as a Potent Pan-Src Kinase Inhibitor", J. Med. Chem. 49:6819-6832 (2006).
Desmarteau D.D. et al., "Easy Preparation of Bioactive Peptides from the Novel Na-Trifluoroethyl Amino Acids", Chemistry Letters, pp. 1052-1053 (2000).
Enguehard C. et al., "Reactivity of a 6-Chloroimidazo[1,2-B]Pyridazine Derivative Towards Suzuki Cross-Coupling Reaction", Synthesis 4:595-600 (2001).
Francavilla P. et al., "Synthesis of New S-Triazolo[4,3-B]Pyridazines", J. Het. Chem., pp. 415-419 (Jun. 1971).
Patani G.A. et al., "Bioisosterism: A Rational Approach in Drug Design", Chem. Rev. 96:3147-3176 (1996).
Schopfer U. et al., "A General Palladium-Catalysed Synthesis of Aromatic and Heteroaromatic Thioethers", Tetrahedron 57:3069-3073 (2001).
U.S. Final Office Action dated Feb. 27, 2013 from U.S. Appl. No. 12/693,736.
U.S. Office Action dated Oct. 18, 2012 from U.S. Appl. No. 12/693,736.
International Search Report dated May 8, 2009 received from the European Patent Office from related Application No. PCT/FR2008/001172.

(Continued)

Primary Examiner — Valerie Rodriguez-Garcia
(74) Attorney, Agent, or Firm — Morrison & Foerster LLP

(57) ABSTRACT

The disclosure relates to compounds of formula (I):

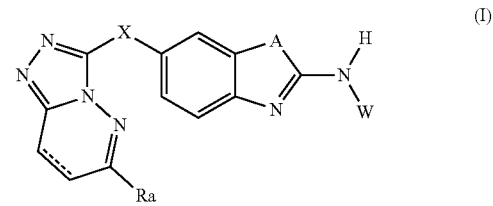

wherein ----, A, W, X, and Ra are as defined in the disclosure, and salts thereof, and to pharmaceutical compositions comprising said compounds, to processes for preparing them, and to their use as medicaments, in particular as MET inhibitors.

18 Claims, No Drawings

(56) References Cited

OTHER PUBLICATIONS

Written Opinion dated Aug. 6, 2008 received from the International Searching Authority from related Application No. PCT/FR2008/001172.

National Cancer Institute; "NCI Cancer Bulletin"; vol. 4, No. 19, Jun. 12, 2007.

Athauda, et al., "c-Met Ectodomain Shedding Rate Correlates with Malignant Potential"; Clin. Cancer Research 2006:12(14), Jul. 15, 2006, pp. 4154-4162.

Jiang, et al., "Hepatocyte growth factor/scatter factor, its molecular, cellular and clinical implications in cancer"; Clinical Reviews in Oncology/Hemotology 29 (1999) 209-248.

Pennacchietti, et al., "Hepatocyte Growth Factor/Scatter Factor Growth"; Encyclopedia of Biological Chemistry, vol. 2, 2004, pp. 367-371.

Weidner, et al., "Properties and Functions of Scatter Factor Hepatocyte Growth Factor and Its Receptor c-Met"; Am.J. Respir. Cell Mol. Biol., vol. 8, pp. 229-237, 1993.

* cited by examiner

6-TRIAZOLOPYRIDAZINE SULFANYL BENZOTHIAZOLE DERIVATIVES AS MET INHIBITORS

CROSS REFERENCE TO RELATED APPLICATIONS

The present application is a divisional of application having U.S. Ser. No. 12/693,736, filed on Jan. 26, 2010, which is a continuation of International Application having Ser. No. PCT/FR2008/001172, filed on Aug. 6, 2008, which claims priority of French Patent Application Nos. 0705789, filed on Aug. 9, 2007 and 0801819, filed on Apr. 2, 2008, the contents of all of which are incorporated herein by reference.

The present invention relates to novel 6-triazolopyridazine sulphanyl benzothiazole and benzimidazole derivatives, to a process for preparing them, to the novel intermediates obtained, to their use as medicaments, to pharmaceutical compositions containing them and to the novel use of such 6-triazolopyridazine sulphanyl benzothiazole and benzimidazole derivatives.

The present invention relates more particularly to novel 6-triazolopyridazine sulphanyl benzothiazole and benzimidazole derivatives having an anticancer activity, via the modulation of the activity of proteins, in particular kinases.

To date, most of the commercial compounds used in chemotherapy are cytotoxic, which poses major problems of side effects and of patient tolerance. These effects could be limited if the medicaments used act selectively on cancer cells, to the exclusion of healthy cells. One of the solutions for limiting the adverse effects of a chemotherapy may thus consist in using medicaments that act on metabolic pathways or constituent elements of these pathways, predominantly expressed in the cancer cells, and which would be sparingly expressed or not expressed in healthy cells. The protein kinases are a family of enzymes that catalyze the phosphorylation of hydroxyl groups of specific residues of proteins, such as tyrosine, serine or threonine. Such phosphorylations can largely modify the function of proteins: thus, protein kinases play an important role in regulating a wide variety of cell processes, including in particular metabolism, cell proliferation, cell adhesion and motility, cell differentiation or cell survival, certain protein kinases playing a central role in the initiation, development and accomplishment of cell cycle events.

Among the various cellular functions in which the activity of a protein kinase is involved, certain processes represent attractive targets for treating certain diseases. As an example, mention may in particular be made of angiogenesis and the control of the cell cycle and also that of cell proliferation, in which protein kinases can play an essential role. These processes are in particular essential for the growth of solid tumours and also for other diseases: in particular molecules that inhibit such kinases are capable of limiting undesired cell proliferations such as those observed in cancers, and may play a part in preventing, regulating or treating neurodegenerative diseases such as Alzheimer's disease or neuronal apoptosis.

A subject of the present invention is novel derivatives with inhibitory effects on protein kinases. The products according to the present invention may thus in particular be used for preventing or treating diseases that may be modulated by inhibition of protein kinases.

The products according to the present invention in particular show anticancer activity, via the modulation of the activity of kinases. Among the kinases for which a modulation of the activity is sought, MET and also mutants of the MET protein are preferred.

The present invention also relates to the use of said derivatives for the preparation of a medicament for use in human therapy.

Thus, one of the objects of the present invention is to provide compounds that have an anticancer activity, by acting in particular on kinases. Among the kinases for which a modulation of the activity is sought, MET is preferred.

In the pharmacological section hereinafter, it is shown, in biochemical tests and on cell lines, that the products of the present invention thus inhibit in particular the autophosphorylation activity of MET and the proliferation of cells whose growth depends on MET or on mutant forms thereof.

MET, or Hepatocyte Growth Factor Receptor, is a receptor with tyrosine kinase activity, expressed in particular by epithelial and endothelial cells. HGF, Hepatocyte Growth Factor, is described as the specific ligand for MET. HGF is secreted by mesenchymal cells and activates the MET receptor, which homodimerizes. Consequently, the receptor autophosphorylates on the tyrosines of the catalytic region Y1230, Y1234 and Y1235.

Stimulation of MET with HGF induces cell proliferation, scattering (or dispersion) and motility, resistance to apoptosis, invasion and angiogenesis.

MET and likewise HGF are found to be overexpressed in many human tumours and a wide variety of cancers. MET is also found to be amplified in gastric tumours and glyoblastomas. Many point mutations of the MET gene have also been described in tumours, in particular in the kinase domain, but also in the juxtamembrane domain and the SEMA domain. Overexpression, amplification or mutations cause constitutive activation of the receptor and deregulation of its functions.

The present invention thus relates in particular to novel inhibitors of the MET protein kinase and of its mutants, that can be used for antiproliferative and antimetastatic treatment, in particular in oncology.

The present invention also relates to novel inhibitors of the MET protein kinase and of its mutants, that can be used for an anti-angiogenic treatment, in particular in oncology.

A subject of the present invention is the products of formula (I):

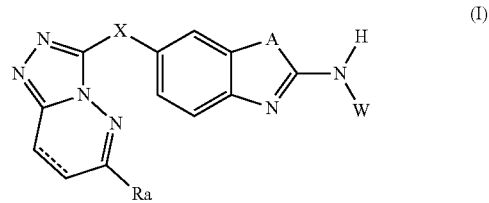

in which

---- represents a single or double bond;

Ra represents a hydrogen atom; a halogen atom; an alkoxy radical optionally substituted with a chlorine atom, a hydroxyl radical or a heterocycloalkyl radical, itself optionally substituted; an O-cycloalkyl radical; an optionally substituted heteroaryl radical; an optionally substituted phenyl radical; an NHCOalk or NHCOcycloalk radical; or an NR1R2 radical as defined hereinafter;

X represents S, SO or $SO_2$;

A represents NH or S;

W represents a hydrogen atom; an alkyl or cycloalkyl radical optionally substituted with alkoxy, heterocycloalkyl or NR3R4; or the COR radical in which R represents:
- a cycloalkyl radical or an alkyl radical optionally substituted with an NR3R4, alkoxy, hydroxyl, phenyl, heteroaryl or heterocycloalkyl radical, themselves optionally substituted;
- an alkoxy radical optionally substituted with NR3R4, alkoxy, hydroxyl or with heterocycloalkyl; an O-phenyl radical or an O—(CH$_2$)$_n$-phenyl radical, with phenyl being optionally substituted and n representing an integer from 1 to 4;
- or the NR1R2 radical in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical containing from 3 to 10 members and optionally one or more other heteroatoms chosen from O, S, N and NH, this radical, including the possible NH that it contains, being optionally substituted;

with R3 and R4, which may be identical or different, representing a hydrogen atom or an alkyl radical, a cycloalkyl radical, a heteroaryl radical or a phenyl radical that is optionally substituted, or else R3 and R4 form, with the nitrogen atom to which they are attached, a cyclic radical containing from 3 to 10 members and optionally one or more other heteroatoms chosen from O, S, N and NH, this radical, including the possible NH that it contains, being optionally substituted;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, NH$_2$, NHalk and N(alk)$_2$ radicals and alkyl, cycloalkyl, heterocycloalkyl, CH$_2$-heterocycloalkyl, phenyl, CH$_2$-phenyl, heteroaryl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, oxo, alkyl and alkoxy containing from 1 to 4 carbon atoms, NH$_2$, NHalk and N(alk)$_2$, said products of formula (I) being in any of the possible racemic, enantiomeric and diastereoisomeric isomer forms, and also the addition salts with mineral and organic acids or with mineral and organic bases of said products of formula (I).

The subject of the present invention is the products of formula (I) as defined above or hereinafter in which $\overline{\phantom{---}}$, X and A have the meanings indicated above or hereinafter;

Ra represents an alkoxy radical optionally substituted with a chlorine atom, a hydroxyl radical or a heterocycloalkyl radical, itself optionally substituted; an O-cycloalkyl radical; an NHCOalk radical; or an NR1aR2a radical; such that R1a and R2a represent a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals;

and W represents a hydrogen atom; an alkyl radical optionally substituted with alkoxy, heterocycloalkyl or NR3R4; or the COR radical in which R represents:
- a cycloalkyl radical or an alkyl radical optionally substituted with an NR3R4, alkoxy, hydroxyl, phenyl, heteroaryl or heterocycloalkyl radical, themselves optionally substituted;
- an alkoxy radical optionally substituted with NR3R4, alkoxy, hydroxyl or with heterocycloalkyl; an O-phenyl radical or an O—(CH$_2$)$_n$-phenyl radical, with phenyl being optionally substituted and n representing an integer from 1 to 4;
- or the NR1R2 radical in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical containing from 3 to 10 members and optionally one or more other heteroatoms chosen from O, S, N and NH, this radical, including the possible NH that it contains, being optionally substituted;

with R3 and R4, which may be identical or different, representing a hydrogen atom or an alkyl radical, a cycloalkyl radical, a heteroaryl radical or a phenyl radical that is optionally substituted, or else R3 and R4 form, with the nitrogen atom to which they are attached, a cyclic radical containing from 3 to 10 members and optionally one or more other heteroatoms chosen from O, S, N and NH, this radical, including the possible NH that it contains, being optionally substituted;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, NH$_2$, NHalk and N(alk)$_2$ radicals and alkyl, cycloalkyl, heterocycloalkyl, CH$_2$-heterocycloalkyl, phenyl, CH$_2$-phenyl, heteroaryl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, oxo, alkyl and alkoxy containing from 1 to 4 carbon atoms, NH$_2$, NHalk and N(alk)$_2$, said products of formula (I) being in any of the possible racemic, enantiomeric and diastereoisomeric isomer forms, and also the addition salts with mineral and organic acids or with mineral and organic bases of said products of formula (I).

A subject of the present invention is the products of formula (I) as defined above or hereinafter in which $\overline{\phantom{---}}$, X and A have the meanings indicated above or hereinafter;

Ra represents an alkoxy radical optionally substituted with a heterocycloalkyl radical, itself optionally substituted; an NHCOalk radical or an NR1aR2a radical; such that R1a and R2a represent a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals;

and W represents a hydrogen atom; an alkyl radical optionally substituted with alkoxy, heterocycloalkyl or NR3R4; or the COR radical in which R represents:
- a cycloalkyl radical or an alkyl radical optionally substituted with an NR3R4, alkoxy, hydroxyl, phenyl, heteroaryl or heterocycloalkyl radical, themselves optionally substituted;
- an alkoxy radical optionally substituted with NR3R4, alkoxy, hydroxyl or with heterocycloalkyl; an O-phenyl radical or an O—(CH$_2$)$_n$-phenyl radical, with phenyl being optionally substituted and n representing an integer from 1 to 4;
- or the NR1R2 radical in which R1 and R2 are such that one of R1 and R2 represents a hydrogen atom or an alkyl radical and the other of R1 and R2 represents a hydrogen atom or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical containing from 3 to 10 members and optionally one or more other heteroatoms chosen from O, S, N and NH, this radical, including the possible NH that it contains, being optionally substituted;

with R3 and R4, which may be identical or different, representing a hydrogen atom or an alkyl radical, a cycloalkyl radical, a heteroaryl radical or a phenyl radical that is optionally substituted, or else R3 and R4 form, with the nitrogen atom to which they are attached, a cyclic radical containing from 3 to 10 members and optionally one or more other heteroatoms chosen from O, S, N and NH, this radical, including the possible NH that it contains, being optionally substituted;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, NH$_2$, NHalk and N(alk)$_2$ radicals and alkyl, cycloalkyl, heterocycloalkyl, CH$_2$-heterocycloalkyl, phenyl, CH$_2$-phenyl, heteroaryl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, oxo, alkyl and alkoxy containing from 1 to 4 carbon atoms, NH$_2$, NHalk and N(alk)$_2$, said products of formula (I) being in any of the possible racemic, enantiomeric and diastereoisomeric isomer forms, and also the addition salts with mineral and organic acids or with mineral and organic bases of said products of formula (I).

A subject of the present invention is the products of formula (I) as defined above in which ---- represents a single or double bond;

Ra represents a hydrogen atom; a halogen atom; an alkoxy radical optionally substituted with a heterocycloalkyl radical, itself optionally substituted; an optionally substituted heteroaryl radical; an optionally substituted phenyl radical; an NHCOalk or NHCOcycloalk radical; or an NR1R2 radical as defined hereinafter;

X represents S, SO or SO$_2$;

A represents NH or S;

W represents a hydrogen atom; an alkyl radical optionally substituted with alkoxy, heterocycloalkyl or NR3R4; or the COR radical in which R represents:
- a cycloalkyl radical or an alkyl radical optionally substituted with an NR3R4, alkoxy, hydroxyl, phenyl, heteroaryl or heterocycloalkyl radical; themselves optionally substituted;
- an alkoxy radical optionally substituted with NR3R4, alkoxy, hydroxyl or with heterocycloalkyl; an O-phenyl radical or an O—(CH$_2$)$_n$-phenyl radical, with phenyl being optionally substituted and n representing an integer from 1 to 4;
- or the NR1R2 radical in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical containing from 3 to 10 members and optionally one or more other heteroatoms chosen from O, S, N and NH, this radical, including the possible NH that it contains, being optionally substituted;

with R3 and R4, which may be identical or different, representing a hydrogen atom or an alkyl radical, a cycloalkyl radical, a heterocycloalkyl radical, a heteroaryl radical or a phenyl radical that is optionally substituted, or else R3 and R4 form, with the nitrogen atom to which they are attached, a cyclic radical containing from 3 to 10 members and optionally one or more other heteroatoms chosen from O, S, N and NH, this radical, including the possible NH that it contains, being optionally substituted;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, NH$_2$, NHalk and N(alk)$_2$ radicals and alkyl, cycloalkyl, heterocycloalkyl, CH$_2$-heterocycloalkyl, phenyl, CH$_2$-phenyl, heteroaryl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, oxo, alkyl and alkoxy containing from 1 to 4 carbon atoms, NH$_2$, NHalk and N(alk)$_2$, said products of formula (I) being in any of the possible racemic, enantiomeric and diastereoisomeric isomer forms, and also the addition salts with mineral and organic acids or with mineral and organic bases of said products of formula (I).

The present invention which thus relates to the products of formula (I) as defined above in which ---- represents a single or double bond, thus relates specifically to the products of formula (I') which represent the products of formula (I) in which ---- represents a single bond and the products of formula (I") which represent the products of formula (I) in which ---- represents a double bond. Thus, all the products of formula (I) as defined above or hereinafter represent in particular products of formula (I') in which ---- represents a single bond. The products of formula (I) as defined above or hereinafter also represent products of formula (I") in which ---- represents a double bond.

A subject of the present invention is the products of formula (I) as defined above or hereinafter in which ----, Ra and X have the values defined above or hereinafter and:

A represents NH or S;

W represents a hydrogen atom; an alkyl radical optionally substituted with alkoxy or heterocycloalkyl; or the COR radical in which R represents:
  a cycloalkyl radical or an alkyl radical optionally substituted with an NR3R4, alkoxy, hydroxyl, phenyl, heteroaryl or heterocycloalkyl radical, themselves optionally substituted;
  an alkoxy radical optionally substituted with NR3R4, alkoxy, hydroxyl or with heterocycloalkyl; an O-phenyl radical or an O—$(CH_2)_n$-phenyl radical, with phenyl being optionally substituted and n representing an integer from 1 to 4;
  or the NR1R2 radical, in which R1 and R2 are such that one of R1 and R2 represents a hydrogen atom or an alkyl radical and the other of R1 and R2 represents a hydrogen atom, a cycloalkyl radical or an alkyl radical optionally substituted with NR3R4 or with alkoxy, or else R1 and R2 form, with the nitrogen atom to which they are attached, a cyclic radical containing from 3 to 10 members and optionally one or more other heteroatoms chosen from O, S, N and NH, this radical, including the possible NH that it contains, being optionally substituted;
with NR3R4 such that R3 and R4, which may be identical or different, represent a hydrogen atom or an alkyl radical, or else R3 and R4 form, with the nitrogen atom to which they are attached, a cyclic radical containing from 3 to 10 members and optionally one or more other heteroatoms chosen from O, S, N and NH, this radical, including the possible NH that it contains, being optionally substituted;
the heterocycloalkyl, heteroaryl and phenyl radicals and also the cyclic radicals that R1 and R2 or R3 and R4 can form with the nitrogen atom to which they are attached, defined above, being optionally substituted with one or more radicals chosen from halogen atoms, hydroxyl, alkoxy, $NH_2$, NHalk and $N(alk)_2$ radicals and alkyl, heterocycloalkyl, $CH_2$-heterocycloalkyl, phenyl, $CH_2$-phenyl, heteroaryl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, alkyl and alkoxy containing from 1 to 4 carbon atoms, $NH_2$, NHalk and $N(alk)_2$;
said products of formula (I) being in any of the possible racemic, enantiomeric and diastereoisomeric isomer forms, and also the addition salts with mineral and organic acids or with mineral and organic bases of said products of formula (I).

A subject of the present invention is thus the products of formula (I) as defined above in which ----, Ra, X, A and W have any one of the values defined above or hereinafter, and the NR1R2 radical is such that one of R1 and R2 represents a hydrogen atom or an alkyl radical and the other of R1 and R2 represents a hydrogen atom or an alkyl radical optionally substituted with NR3R4 or with alkoxy, or else R1 and R2 form, with the nitrogen atom to which they are attached, a cyclic radical containing from 3 to 10 members and optionally one or more other heteroatoms chosen from O, S, N and NH, this radical, including the possible NH that it contains, being optionally substituted;
all the other substituents having the definitions indicated above;
said products of formula (I) being in any of the possible racemic, enantiomeric and diastereoisomeric isomer forms, and also the addition salts with mineral and organic acids or with mineral and organic bases of said products of formula (I).

A subject of the present invention is the products of formula (I) as defined above or hereinafter
in which
---- represents a single or double bond;
Ra represents a hydrogen atom or else a halogen atom or else an optionally substituted phenyl radical;
X represents S, SO or $SO_2$;
A represents NH or S;
W represents a hydrogen atom or the COR radical in which R represents:
  a cycloalkyl radical or an alkyl radical optionally substituted with a phenyl, heteroaryl, NR3R4 or heterocycloalkyl radical, themselves optionally substituted;
  an alkoxy radical optionally substituted with NR3R4, i.e. an O—(CH2)n-NR3R4 radical; an O-phenyl radical or an O—$(CH_2)_n$-phenyl radical, with phenyl being optionally substituted and n representing an integer from 1 to 4;
  or the NR1R2 radical in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical optionally containing one or more other heteroatoms chosen from O, S, N and NH, this radical, including the possible NH that it contains, being optionally substituted;
with R3 and R4, which may be identical or different, representing a hydrogen atom or an alkyl radical, a cycloalkyl radical, a heteroaryl radical or an optionally substituted phenyl radical, or else R3 and R4 form, with the nitrogen atom to which they are attached, a cyclic radical optionally containing one or more other heteroatoms chosen from O, S, N and NH, this radical, including the possible NH that it contains, being optionally substituted;
all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, $NH_2$, NHalk, $N(alk)_2$ radicals and alkyl, cycloalkyl, $CH_2$-heterocycloalkyl, $CH_2$-phenyl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, oxo, alkyl and alkoxy containing from 1 to 4 carbon atoms, $NH_2$, NHalk and $N(alk)_2$,
said products of formula (I) being in any of the possible racemic, enantiomeric and diastereoisomeric isomer forms, and also the addition salts with mineral and organic acids or with mineral and organic bases of said products of formula (I).

Products of formula (I) as defined above or hereinafter in which ----, Ra and X have the values defined above or hereinafter and:

A represents NH or S;
W represents a hydrogen atom or an alkyl radical or the COR radical in which R represents:
  an alkyl radical optionally substituted with $OCH_3$ or NR3R4;
  a cycloalkyl radical;
  an alkoxy radical optionally substituted with $OCH_3$ or NR3R4, i.e. an $O-(CH2)n-OCH_3$ radical or an $O-(CH_2)_n-NR3R4$ radical, an O-phenyl radical or an $O-(CH_2)_n$-phenyl radical, with phenyl being optionally substituted and n representing an integer from 1 to 2;
  or the NR1R2 radical, in which R1 and R2 are such that one of R1 and R2 represents a hydrogen atom, a cycloalkyl radical or an alkyl radical and the other of R1 and R2 represents an alkyl radical optionally substituted with NR3R4, or else R1 and R2 form with the nitrogen atom to which they are attached, a cyclic radical optionally containing one or more other heteroatoms chosen from O, S, N and NH, this radical, including the possible NH that it contains, being optionally substituted;
with NR3R4 such that R3 and R4, which may be identical or different, represent a hydrogen atom or an alkyl radical, or else R3 and R4 form, with the nitrogen atom to which they are attached, a cyclic radical optionally containing one or more other heteroatoms chosen from O, S, N and NH, this radical, including the possible NH that it contains, being optionally substituted;
the phenyl radicals and also the cyclic radicals that R1 and R2 or R3 and R4 can form with the nitrogen atom to which they are attached, defined above, being optionally substituted with one or more radicals chosen from halogen atoms, hydroxyl, alkoxy, $NH_2$, NHalk and $N(alk)_2$ radicals and alkyl, $CH_2$-heterocycloalkyl, $CH_2$-phenyl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, alkyl and alkoxy containing from 1 to 4 carbon atoms, $NH_2$, NHalk and $N(alk)_2$;
said products of formula (I) being in any of the possible racemic, enantiomeric and diastereoisomeric isomer forms, and also the addition salts with mineral and organic acids or with mineral and organic bases of said products of formula (I).

A subject of the present invention is thus the products of formula (I) as defined above in which ----, Ra and X have any one of the values defined above or hereinafter,
A represents NH or S;
W represents a hydrogen atom or the COR radical in which R represents:
  an alkyl radical optionally substituted with NR3R4;
  an alkoxy radical optionally substituted with NR3R4, i.e. an $O-(CH_2)_n-NR3R4$ radical, an O-phenyl radical or an $O-(CH_2)_n$-phenyl radical, with phenyl being optionally substituted and n representing an integer from 1 to 2;
  or the NR1R2 radical, in which R1 and R2 are such that one of R1 and R2 represents a hydrogen atom or an alkyl radical and the other of R1 and R2 represents an alkyl radical optionally substituted with NR3R4, or else R1 and R2 form, with the nitrogen atom to which they are attached, a cyclic radical optionally containing one or more other heteroatoms chosen from O, S, N and NH, this radical, including the possible NH that it contains, being optionally substituted;
with NR3R4 such that R3 and R4, which may be identical or different, represent a hydrogen atom or an alkyl radical, or else R3 and R4 form, with the nitrogen atom to which they are attached, a cyclic radical optionally containing one or more other heteroatoms chosen from O, S, N and NH, this radical, including the possible NH that it contains, being optionally substituted;
the phenyl radicals and also the cyclic radicals that R1 and R2 or R3 and R4 can form with the nitrogen atom to which they are attached, defined above, being optionally substituted with one or more radicals chosen from halogen atoms, hydroxyl, alkoxy, $NH_2$, NHalk and $N(alk)_2$ radicals and alkyl, $CH_2$-heterocycloalkyl, $CH_2$-phenyl, CO-phenyl and S-heteroaryl radicals, such that, in the latter radicals, the alkyl, heterocycloalkyl, phenyl and heteroaryl radicals are themselves optionally substituted with one or more radicals chosen from halogen atoms and the radicals: hydroxyl, alkyl and alkoxy containing from 1 to 4 carbon atoms, $NH_2$, NHalk and $N(alk)_2$;
said products of formula (I) being in any of the possible racemic, enantiomeric and diastereoisomeric isomer forms, and also the addition salts with mineral and organic acids or with mineral and organic bases of said products of formula (I).

A subject of the present invention is thus the products of formula (I) as defined above in which ----, X, A and W have the meanings indicated above or hereinafter, Ra represents a hydrogen atom or else a chlorine atom or else the radical:

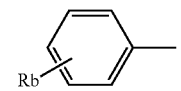

with Rb representing a halogen atom or an S-heteroaryl radical optionally substituted with a radical chosen from halogen atoms and the radicals: hydroxyl, alkyl and alkoxy containing from 1 to 4 carbon atoms, $NH_2$, NHalk and $N(alk)_2$,
said products of formula (I) being in any of the possible racemic, enantiomeric and diastereoisomeric isomer forms, and also the addition salts with mineral and organic acids or with mineral and organic bases of said products of formula (I).

In the products of formula (I) and in the text hereinbelow:
  the term "alkyl (or Alk) radical" denotes linear and, where appropriate, branched methyl, ethyl, propyl, isopropyl, butyl, isobutyl, sec-butyl, tert-butyl, pentyl, isopentyl, hexyl, isohexyl and also heptyl, octyl, nonyl and decyl radicals and also the linear or branched positional isomers thereof: alkyl radicals containing from 1 to 6 carbon atoms and more particularly alkyl radicals containing from 1 to 4 carbon atoms of the above list are preferred;
  the term "alkoxy radical" denotes linear and, where appropriate, branched methoxy, ethoxy, propoxy, isopropoxy, linear, secondary or tertiary butoxy, pentoxy or hexoxy radicals and also the linear or branched positional isomers thereof: alkoxy radicals containing from 1 to 4 carbon atoms of the above list are preferred;
  the term "halogen atom" denotes chlorine, bromine, iodine or fluorine atoms, and preferably the chlorine, bromine or fluorine atom;

the term "cycloalkyl radical" denotes a saturated carbocyclic radical containing 3 to 10 carbon atoms and thus denotes in particular cyclopropyl, cyclobutyl, cyclopentyl and cyclohexyl radicals, and most particularly cyclopropyl, cyclopentyl and cyclohexyl radicals;

the term "heterocycloalkyl radical" thus denotes a monocyclic or bicyclic carbocyclic radical containing from 3 to 10 members, interrupted with one or more heteroatoms, which may be identical or different, chosen from oxygen, nitrogen or sulphur atoms: mention may, for example, be made of morpholinyl, thiomorpholinyl, aziridyl, azetidyl, piperazinyl, piperidyl, homopiperazinyl, pyrrolidinyl, imidazolidinyl, pyrazolidinyl, tetrahydrofuryl, tetrahydrothienyl, hexahydropyran, oxodihydropyridazinyl or else oxetanyl radicals, all these radicals being optionally substituted;

the terms "aryl" and "heteroaryl" denote monocyclic or bicyclic, unsaturated or partially unsaturated, respectively carbocyclic and heterocyclic radicals containing at most 12 members, which may optionally contain a —C(O) member, the heterocyclic radicals containing one or more heteroatoms, which may be identical or different, chosen from O, N or S with N, where appropriate, optionally substituted;

the term "aryl radical" thus denotes monocyclic or bicyclic radicals containing 6 to 12 members, such as, for example, phenyl, naphthyl, biphenyl, indenyl, fluorenyl and anthracenyl radicals, more particularly phenyl and naphthyl radicals, and even more particularly the phenyl radical. It may be noted that a carbocyclic radical containing a —C(O) member is, for example, the tetralone radical;

the term "heteroaryl radical" thus denotes monocyclic or bicyclic radicals containing 5 to 12 members: monocyclic heteroaryl radicals, for instance the radicals: thienyl such as 2-thienyl and 3-thienyl, furyl such as 2-furyl or 3-furyl, pyrannyl, pyrrolyl, pyrrolinyl, pyrazolinyl, imidazolyl, pyrazolyl, pyridyl such as 2-pyridyl, 3-pyridyl and 4-pyridyl, pyrazinyl, pyrimidinyl, pyridazinyl, oxazolyl, thiazolyl, isothiazolyl, diazolyl, thiadiazolyl, thiatriazolyl, oxadiazolyl, isoxazolyl such as 3- or 4-isoxazolyl, furazanyl or tetrazolyl, which may be free or salified, all these radicals being optionally substituted, among which more particularly the radicals: thienyl such as 2-thienyl and 3-thienyl, furyl such as 2-furyl, pyrrolyl, pyrrolinyl, pyrazolinyl, imidazolyl, pyrazolyl, oxazolyl, isoxazolyl, pyridyl, pyridazinyl, these radicals being optionally substituted; bicyclic heteroaryl radicals, for instance the radicals: benzothienyl such as 3-benzothienyl, benzothiazolyl, quinolyl, isoquinolyl, dihydroquinolyl, quinolone, tetralone, adamentyl, benzofuryl, isobenzofuryl, dihydrobenzofuran, ethylenedioxyphenyl, thianthrenyl, benzopyrrolyl, benzimidazolyl, benzoxazolyl, thionaphthyl, indolyl, azaindolyl, indazolyl, purinyl, thienopyrazolyl, tetrahydroindazolyl, tetrahydrocyclopentapyrazolyl, dihydrofuropyrazolyl, tetrahydropyrrolopyrazolyl, oxotetrahydropyrrolopyrazolyl, tetrahydropyranopyrazolyl, tetrahydropyridinopyrazolyl or oxodihydropyridinopyrazolyl, all these radicals being optionally substituted.

As examples of heteroaryl or bicyclic radicals, mention may more particularly be made of pyrimidinyl, pyridyl, pyrrolyl, azaindolyl, indazolyl or pyrazolyl radicals, optionally substituted with one or more substituents, which may be identical or different, as indicated above.

The carboxyl radical(s) of the products of formula (I) may be salified or esterified with the various groups known to those skilled in the art, among which mention may, for example, be made of:

among the salification compounds, mineral bases such as, for example, an equivalent of sodium, of potassium, of lithium, of calcium, of magnesium or of ammonium or organic bases such as, for example, methylamine, propylamine, trimethylamine, diethylamine, triethylamine, N,N-dimethylethanolamine, tris(hydroxymethyl)aminomethane, ethanolamine, pyridine, picoline, dicyclohexylamine, morpholine, benzylamine, procaine, lysine, arginine, histidine or N-methylglucamine, among the esterification compounds, alkyl radicals for forming alkoxycarbonyl groups, such as, for example, methoxycarbonyl, ethoxycarbonyl, tert-butoxycarbonyl or benzyloxycarbonyl, these alkyl radicals possibly being substituted with radicals chosen, for example, from halogen atoms, and hydroxyl, alkoxy, acyl, acyloxy, alkylthio, amino or aryl radicals, such as for instance in chloromethyl, hydroxypropyl, methoxymethyl, propionyloxymethyl, methylthiomethyl, dimethylaminoethyl, benzyl or phenethyl groups.

The addition salts with mineral or organic acids of the products of formula (I) may, for example, be the salts formed with hydrochloric acid, hydrobromic acid, hydroiodic acid, nitric acid, sulphuric acid, phosphoric acid, propionic acid, acetic acid, trifluoroacetic acid, formic acid, benzoic acid, maleic acid, fumaric acid, succinic acid, tartaric acid, citric acid, oxalic acid, glyoxylic acid, aspartic acid, ascorbic acid, alkylmonosulphonic acids such as, for example, methanesulphonic acid, ethanesulphonic acid or propanesulphonic acid, alkyldisulphonic acids such as, for example, methanedisulphonic acid or alpha,beta-ethanedisulphonic acid, arylmonosulphonic acids such as benzenesulphonic acid and aryldisulphonic acids.

It may be recalled that stereoisomerism can be defined in its broad sense as the isomerism of compounds having the same structural formulae, but the various groups of which are arranged differently in space, such as in particular in monosubstituted cyclohexanes, the substituent of which can be in the axial or equatorial position, and the various possible rotational conformations of ethane derivatives. However, another type of stereoisomerism exists, due to the different spatial arrangements of substituents attached either on double bonds or on rings, which is commonly known as geometrical isomerism or cis-trans isomerism. The term stereoisomers is used in the present application in its broadest sense and therefore relates to all the compounds indicated above.

The cyclic radicals that, on the one hand, R1 and R2 can form with the nitrogen atom to which they are attached and, on the other hand, R3 and R4 can form with the nitrogen atom to which they are attached are optionally substituted with one or more radicals chosen from those indicated above for the possible substituents of the heterocycloalkyl radicals, i.e. one or more radicals chosen from halogen atoms, hydroxyl, oxo, alkoxy, $NH_2$; NHalk and $N(alk)_2$ radicals, and alkyl, heterocycloalkyl, $CH_2$-heterocycloalkyl, phenyl, $CH_2$-phenyl, heteroaryl and CO-phenyl radicals, such that, in these latter radicals, the alkyl, heterocycloalkyl and phenyl radicals are themselves optionally substituted with one or more radicals chosen from halogen atoms and the radicals: hydroxyl, oxo, alkyl and alkoxy containing from 1 to 4 carbon atoms, $NH_2$; NHalk and $N(alk)_2$.

The cyclic radicals that, on the one hand, R1 and R2 can form with the nitrogen atom to which they are attached and, on the other hand, that R3 and R4 can form with the nitrogen atom to which they are attached, are in particular optionally substituted with one or more radicals, which may be identical or different, chosen from halogen atoms and alkyl, hydroxyl, alkoxy, $CH_2$-pyrrolidinyl, $CH_2$-phenyl, heteroaryl and phenyl radicals, in which the alkyl, pyrrolidinyl and phenyl radicals are themselves optionally substituted with one or more radicals, which may be identical or different, chosen from halogen atoms and alkyl, hydroxyl, oxo and alkoxy radicals.

The heterocycloalkyl radicals as defined above represent in particular azepanyl, morpholinyl, pyrrolidinyl, piperidyl, and piperazinyl radicals, themselves optionally substituted, as defined above or hereinafter.

When NR1R2 or NR3R4 forms a ring as defined above, such an amino ring may be chosen in particular from pyrrolidinyl, pyrazolidinyl, pyrazolinyl, piperidyl, azepinyl, morpholino or piperazinyl radicals, these radicals being themselves optionally substituted as indicated above or hereinafter: for example, with one or more radicals, which may be identical or different, chosen from halogen atoms and alkyl, hydroxyl, alkoxy, phenyl and $CH_2$-phenyl radicals, the alkyl or phenyl radicals being themselves optionally substituted with one or more radicals, which may be identical or different, chosen from halogen atoms and alkyl, hydroxyl and alkoxy radicals.

The NR1R2 or NR3R4 ring may more particularly be chosen from the radicals pyrrolidinyl, morpholino optionally substituted with one or two alkyl radicals or piperazinyl optionally substituted on the second nitrogen atom with an alkyl, phenyl and/or $CH_2$-phenyl radical, themselves optionally substituted with one or more radicals, which may be identical or different, chosen from halogen atoms and alkyl, hydroxyl and alkoxy radicals.

A subject of the present invention is in particular the products of formula (I) in which A represents NH, the substituents Ra, X and W being chosen from all the values defined for these radicals above or below, said products of formula (I) being in any of the possible racemic, enantiomeric and diastereoisomeric isomer forms, and also the addition salts with mineral and organic acids or with mineral and organic bases of said products of formula (I).

A subject of the present invention is in particular the products of formula (I) in which A represents S, the substituents Ra, X and W being chosen from all the values defined for these radicals above and below, said products of formula (I) being in any of the possible racemic, enantiomeric and diastereoisomeric isomer forms, and also the addition salts with mineral and organic acids or with mineral and organic bases of said products of formula (I).

In particular, the present invention relates to the products of formula (I) corresponding to formula (Ia) or (Ib):

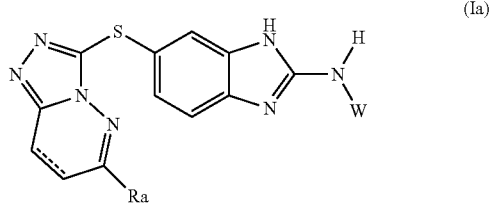

(Ia)

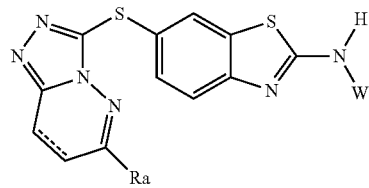

(Ib)

in which ----, Ra and W are chosen from all the meanings indicated above or hereinafter,
said products of formula (Ia) and (Ib) being in any of the possible racemic, enantiomeric and diastereoisomeric isomer forms, and also the addition salts with mineral and organic acids or with mineral and organic bases of said products of formulae (Ia) and (Ib).

The present invention therefore relates in particular to the products of formula (I) as defined above or hereinafter in which ---- represents a single bond, corresponding to the products of formula (I'):

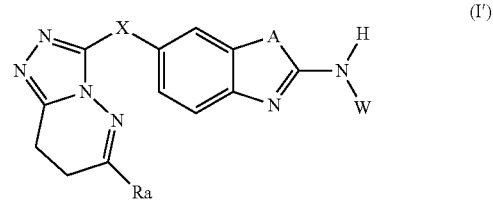

(I')

the substituents Ra, X, A and W are chosen from all the meanings indicated above or hereinafter,
said products of formula (I') being in any of the possible racemic, enantiomeric and diastereoisomeric isomer forms, and also the addition salts with mineral and organic acids or with mineral and organic bases of said products of formula (I').

The present invention therefore relates in particular to the products of formula (I) as defined above or hereinafter in which ---- represents a double bond, corresponding to the products of formula (I"):

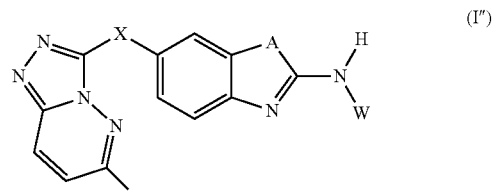

(I")

in which the substituents Ra, X, A and W are chosen from all the meanings indicated above or hereinafter,
said products of formula (I") being in any of the possible racemic, enantiomeric and diastereoisomeric isomer forms, and also the addition salts with mineral and organic acids or with mineral and organic bases of said products of formula (I").

The present invention therefore relates in particular to the products of formula (Ia) as defined above or hereinafter in which ---- represents a single bond, corresponding to the products of formula (Ia):

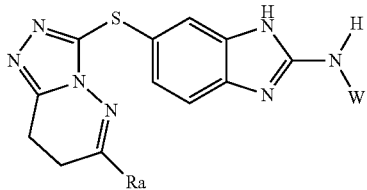
(I'a)

in which Ra and W are chosen from all the meanings indicated above or hereinafter,
said products of formula (I'a) being in any of the possible racemic, enantiomeric and diastereoisomeric isomer forms, and also the addition salts with mineral and organic acids or with mineral and organic bases of said products of formula (I'a).

The present invention therefore relates in particular to the products of formula (Ia) as defined above or hereinafter in which ---- represents a double bond, corresponding to the products of formula (I"a):

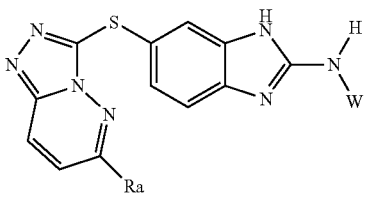
(I"a)

in which Ra and W are chosen from all the meanings indicated above or hereinafter,
said products of formula (I"a) being in any of the possible racemic, enantiomeric and diastereoisomeric isomer forms, and also the addition salts with mineral and organic acids or with mineral and organic bases of said products of formula (I"a).

The present invention therefore relates in particular to the products of formula (Ib) as defined above or hereinafter in which ---- represents a single bond, corresponding to the products of formula (I'b):

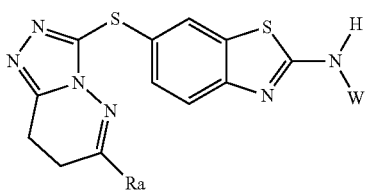
(I'b)

in which Ra and W are chosen from all the meanings indicated above or hereinafter,
said products of formula (I'b) being in any of the possible racemic, enantiomeric and diastereoisomeric isomer forms, and also the addition salts with mineral and organic acids or with mineral and organic bases of said products of formula (I'b).

The present invention therefore relates in particular to the products of formula (Ib) as defined above or hereinafter in which ---- represents a double bond, corresponding to the products of formula (I"b):

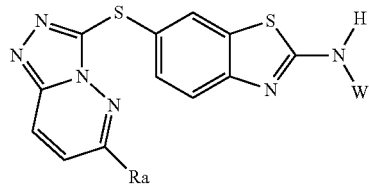
(I"b)

in which Ra and W are chosen from all the meanings indicated above or hereinafter,
said products of formula (I"b) being in any of the possible racemic, enantiomeric and diastereoisomeric isomer forms, and also the addition salts with mineral and organic acids or with mineral and organic bases of said products of formula (I"b).

When, in the products of formula (I), Ra represents the radical:

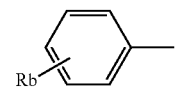

Rb is in particular in the para-position.
When Rb defined above represents a halogen atom, Rb represents in particular fluorine.

A subject of the present invention is most particularly the products of formula (I) as defined above, corresponding to the following formulae:
methyl (6-{[6-(4-fluorophenyl)[1,2,4]triazolo[4,3-b]pyridazin-3-yl]sulphanyl}-1,3-benzothiazol-2-yl)carbamate
6-{[6-(4-fluorophenyl)[1,2,4]triazolo[4,3-b]pyridazin-3-yl]sulphanyl}-1,3-benzothiazol-2-amine
methyl (6-{[6-(4-fluorophenyl)[1,2,4]triazolo[4,3-b]pyridazin-3-yl]sulphanyl}-1H-benzimidazol-2-yl)carbamate
1-(6-{[6-(4-fluorophenyl)[1,2,4]triazolo[4,3-b]pyridazin-3-yl]sulphanyl}-1H-benzimidazol-2-yl)-3-(2-morpholin-4-ylethyl)urea
6-{[6-(4-fluorophenyl)[1,2,4]triazolo[4,3-b]pyridazin-3-yl]sulphanyl}-1H-benzimidazol-2-amine
1-(2-morpholin-4-ylethyl)-3-[6-([1,2,4]triazolo[4,3-b]pyridazin-3-ylsulphanyl)-1,3-benzothiazol-2-yl]urea
1-(6-{[6-(4-fluorophenyl)[1,2,4]triazolo[4,3-b]pyridazin-3-yl]sulphanyl}-1,3-benzothiazol-2-yl)-3-(2-morpholin-4-ylethyl)urea
1-{2-[(2R,6S)-2,6-dimethylmorpholin-4-yl]ethyl}-3-(6-{[6-(4-fluorophenyl)-[1,2,4]triazolo[4,3-b]pyridazin-3-yl]sulphanyl}-1,3-benzothiazol-2-yl)urea
(6-{[6-(4-fluorophenyl)[1,2,4]triazolo[4,3-b]pyridazin-3-yl]sulphanyl}-1,3-benzothiazol-2-yl)carbamate of 2-morpholin-4-ylethyl
1-(6-{[6-(4-fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea
N-(6-{[6-(4-fluorophenyl)[1,2,4]triazolo[4,3-b]pyridazin-3-yl]sulphanyl}-1,3-benzothiazol-2-yl)-4-morpholin-4-ylbutanamide
1-[2-(diethylamino)ethyl]-3-(6-{[6-(4-fluorophenyl)[1,2,4]triazolo[4,3-b]pyridazin-3-yl]sulphanyl}-1,3-benzothiazol-2-yl)urea
1-{6-[(6-methoxy[1,2,4]triazolo[4,3-b]pyridazin-3-yl)sulphanyl]-1,3-benzothiazol-2-yl}-3-[2-(morpholin-4-yl)ethyl]urea N-[6-({6-[(2-methoxyethyl)amino][1,2,4]triazolo[4,3-b]pyridazin-3-yl}sulphanyl)-1,3-benzothiazol-2-yl]acetamide 6-{[6-(4-fluorophenyl)[1,2,4]triazolo[4,3-b]pyridazin-3-yl]sulphanyl}-N-[2-(morpholin-4-yl)ethyl]-1,3-benzothiazol-2-amine phenyl 6-{[6-(4-fluorophenyl)[1,2,4]triazolo[4,3-b]pyridazin-3-yl]sulphanyl}-1,3-benzothiazol-2-yl)carbamate 1-{6-[(6-ethoxy[1,2,4]triazolo[4,3-b]pyridazin-3-yl)sulphanyl]-1,3-benzothiazol-2-yl}-3-[2-(morpholin-4-yl)ethyl]urea 1-{6-[(6-ethoxy-7,8-dihydro[1,2,4]triazolo[4,3-b]pyridazin-3-yl)sulphanyl]-1,3-benzothiazol-2-yl}-3-[2-(morpholin-4-yl)ethyl]urea N-[6-({6-[(2-methoxyethyl)amino][1,2,4]triazolo[4,3-b]pyridazin-3-yl}sulphanyl)-1,3-benzothiazol-2-yl]cyclopropanecarboxamide 1-(6-{[6-(4-fluorophenyl)[1,2,4]triazolo[4,3-b]pyridazin-3-yl]sulphanyl}-1,3-benzothiazol-2-yl)-3-[2-(4-oxidomorpholin-4-yl)ethyl]urea 6-{[6-(1-methyl-1H-pyrazol-4-yl)[1,2,4]triazolo[4,3-b]pyridazin-3-yl]sulphanyl}-1,3-benzothiazol-2-amine 1-(6-{[6-(4-fluorophenyl)-7,8-dihydro[1,2,4]triazolo[4,3-b]pyridazin-3-yl]sulphanyl}-1,3-benzothiazol-2-yl)-3-[2-(morpholin-4-yl)ethyl]urea oxetan-2-ylmethyl (6-{[6-(4-fluorophenyl)[1,2,4]triazolo[4,3-b]pyridazin-3-yl]sulphanyl}-1,3-benzothiazol-2-yl)carbamate N-{6-[(6-methoxy[1,2,4]triazolo[4,3-b]pyridazin-3-yl)sulphanyl]-1,3-benzothiazol-2-yl}cyclopropanecarboxamide N-(6-{[6-(4-fluorophenyl)[1,2,4]triazolo[4,3-b]pyridazin-3-yl]sulphanyl}-1,3-benzothiazol-2-yl)acetamide 1-{6-[(6-methoxy[1,2,4]triazolo[4,3-b]pyridazin-3-yl)sulphanyl]-1,3-benzothiazol-2-yl}-3-[2-(pyrrolidin-1-yl)ethyl]urea 6-[(6-ethoxy[1,2,4]triazolo[4,3-b]pyridazin-3-yl)sulphanyl]-1,3-benzothiazol-2-amine 6-{[6-(3-fluorophenyl)[1,2,4]triazolo[4,3-b]pyridazin-3-yl]sulphanyl}-1,3-benzothiazol-2-amine 1-cyclopropyl-3-{6-[(6-ethoxy[1,2,4]triazolo[4,3-b]pyridazin-3-yl)sulphanyl]-1,3-benzothiazol-2-yl}urea N-(6-{[6-(4-fluorophenyl)[1,2,4]triazolo[4,3-b]pyridazin-3-yl]sulphanyl}-1,3-benzothiazol-2-yl)cyclopropanecarboxamide N-(6-{[6-(4-fluorophenyl)-7,8-dihydro[1,2,4]triazolo[4,3-b]pyridazin-3-yl]sulphanyl}-1,3-benzothiazol-2-yl)cyclopropanecarboxamide 1-(6-{[6-(3-fluorophenyl)[1,2,4]triazolo[4,3-b]pyridazin-3-yl]sulphanyl}-1,3-benzothiazol-2-yl)-3-[2-(morpholin-4-yl)ethyl]urea and also the addition salts with mineral and organic acids or with mineral and organic bases of said products of formula (I).

A subject of the present invention is also any process for preparing the products of formula (I) as defined above.

A subject of the present invention is thus any process for preparing the products of formula (I) as defined above in which A represents NH.

A subject of the present invention is thus any process for preparing the products of formula (I) as defined above in which A represents S.

The products according to the invention can be prepared using conventional organic chemistry methods. Schemes 1, 2, 3, 4, 5, 6 and 7 below illustrate the methods used for preparing the products of formula (I). In this respect, they cannot constitute a limitation of the scope of the invention, with regard to the methods for preparing the compounds claimed.

The products of formula (I) as defined above according to the present invention may thus in particular be prepared according to the processes described in schemes 1, 2, 3, 4, 5, 6 and 7 below.

A subject of the present invention is thus also the process for preparing products of formula (I) according to scheme 1 as defined hereinafter.

A subject of the present invention is thus also the process for preparing products of formula (I) according to scheme 2 as defined hereinafter.

A subject of the present invention is thus also the process for preparing products of formula (I) according to scheme 3 as defined hereinafter.

A subject of the present invention is thus also the process for preparing products of formula (I) according to scheme 4 as defined hereinafter.

A subject of the present invention is thus also the process for preparing products of formula (I) according to scheme 5 as defined hereinafter.

A subject of the present invention is thus also the process for preparing products of formula (I) according to scheme 6 as defined hereinafter.

A subject of the present invention is thus also the process for preparing products of formula (I) according to scheme 7 as defined hereinafter.

Just as, among the products of formula (I) as defined above in which ---- represents a single or double bond, the products of formula (I') which represent the products of formula (I) in which ---- represents a single bond and the products of formula (I") which represent the products of formula (I) in which ---- represents a double bond are defined, similarly, for the synthesis intermediates as defined hereinafter, of formulae (a), (b), (c), (d), (e) and (f) in which ---- represents a single or double bond, the compounds of formulae (a'), (b'), (c'), (d'), (e') and (f') in which ---- represents a single bond, and the compounds of formulae (a"), (b"), (c"), (d"), (e") and (f") in which ---- represents a double bond are defined.

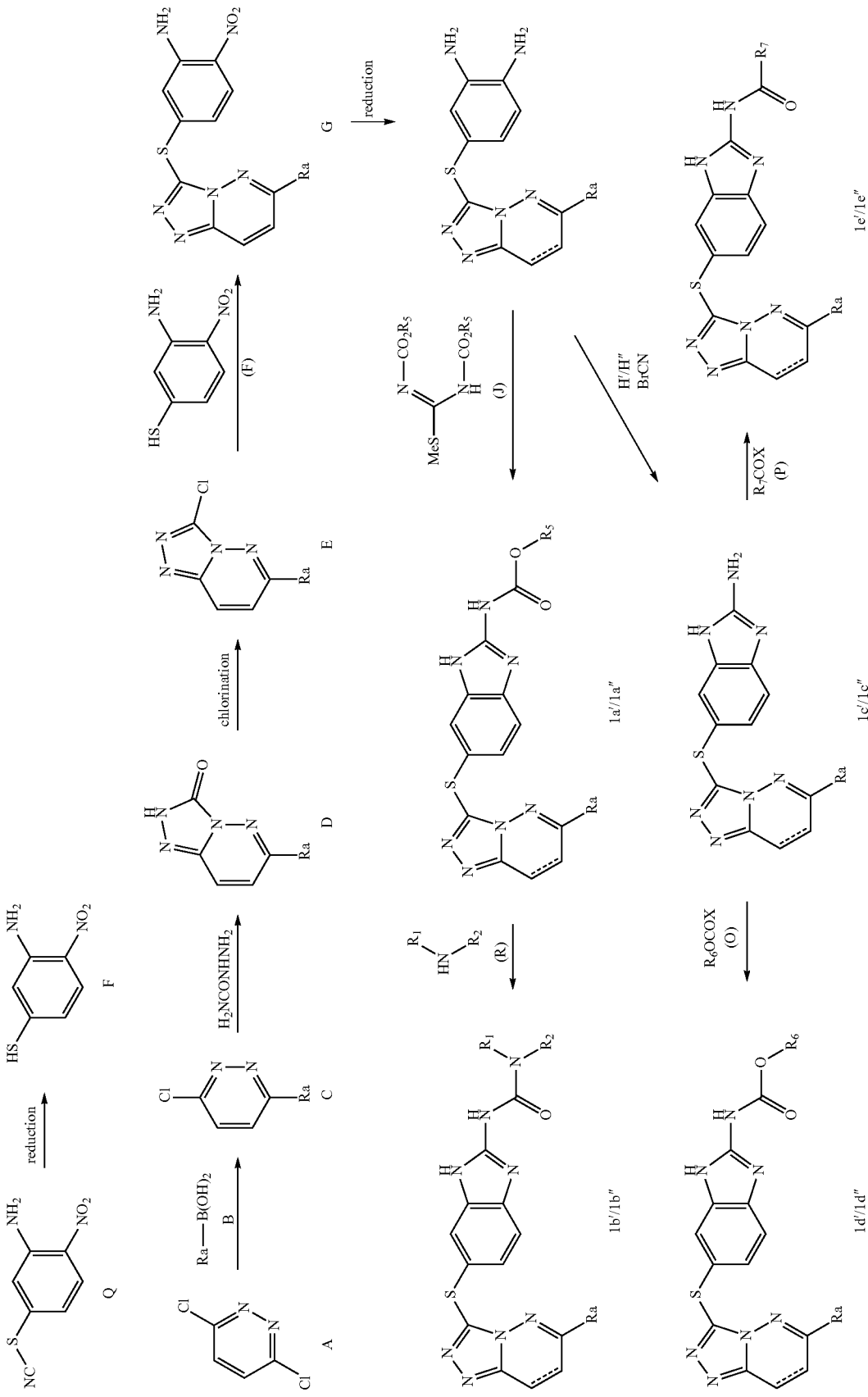
Scheme 1: syntheses of benzimidazole derivatives of formulae (1a'), (1b'), (1''c), (1d''), (1e''), (1a'), (1b'), (1c'), (1d') and (1e')

In scheme 1 above, the substituents Ra, R1 and R2 have the meanings indicated above for the products of formulae (I') and (I"), the substituent R5, in the compounds of formulae (J), (1a') and (1a"), represents an alkyl radical and the substituent R6, in the compounds of formulae (O), (1d') and (1d"), represent an alkyl radical optionally substituted with NR3R4 (a —(CH$_2$)$_n$—NR3R4 radical), alkoxy, hydroxyl, heterocycloalkyl, phenyl or —(CH$_2$)$_n$-phenyl, with phenyl being optionally substituted and n representing an integer from 1 to 4. The substituent R7 in the compounds of formulae (P) and (1e')/(1e") represents a cycloalkyl or alkyl radical optionally substituted with an NR3R4, alkoxy, hydroxyl, phenyl, heteroaryl or heterocycloalkyl radical, themselves optionally substituted.

In above scheme 1, the benzimidazoles of general formulae (1a"), (1b"), (1c"), (1d") and (1e") and also the reduced analogues thereof of general formulae (1a'), (1b'), (1c'), (1d') and (1e') can be prepared from 3,6-dichloropyrazine (A) (commercial compound).

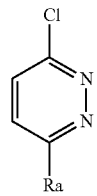

C

The compounds (C) can be obtained, for example, by coupling 3,6-dichloropyrazine with a boronic acid of formula (B) with Ra as defined above, under the conditions described, for example, by A. Gueiffier et al. (Synthesis; 2001; 4; 595) in the presence of tetrakis(triphenylphosphine)palladium(0), in a solvent such as dioxane and in the presence of a base such as sodium hydrogen carbonate, at a temperature in the region of 115° C.

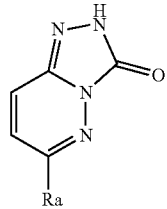

D

The compounds (D) such that Ra is different from H can be obtained, for example, by reaction of hydrazinecarboxamide hydrochloride with the compounds of formula (C) in a solvent, such as butanol, and in the presence of a base such as triethylamine, at a temperature in the region of 140° C.

The compounds (D) such that Ra=H can be obtained as described by P. Francavilla and F. Lairia (Journal of Heterocyclic Chemistry; 1971; 415) by hydrogenolysis of a compound (D) with Ra=Cl (commercial compound), for example, in the presence of ammonium formate and palladium-on-charcoal, in a solvent such as methanol at a temperature in the region of 70° C.

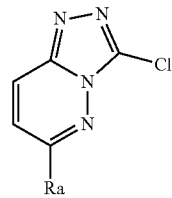

E

The compounds (E) can be obtained, for example, by reaction of phosphoric trichloride (phosphorus oxychloride) with the compounds of formula (D). The reaction is carried out, for example, at a temperature in the region of 150° C., in a sealed tube under microwaves.

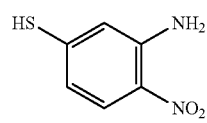

F

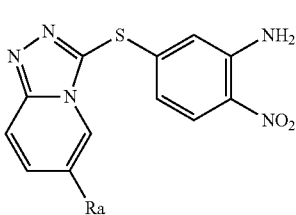

G

The compounds (G) can be obtained, for example, by reaction of 3-amino-4-nitrobenzenethiol of formula (F) with the compounds of formula (E). The compounds of formula (F) are obtained by reduction, in situ, of 3-amino-4-nitrophenyl thiocyanate (Q) (commercial compound), for example, in the presence of sodium borohydride in a solvent such as N,N-dimethylformamide, at a temperature in the region of 20° C.

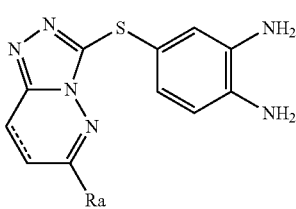

H'/H"

The compounds (H") such that ---- represents a double bond can be obtained, for example, by reduction with iron (0) on the compounds of formula (G), in a solvent such as methanol, in the presence of acetic acid, at a temperature in the region of 70° C.

The compounds (H') such that ---- represents a single bond can be obtained, for example, by reduction with zinc (0) on the compounds of formula (G), in the presence of acetic acid, at a temperature in the region of 20° C.

More particularly, the carbamates of general formulae (1a') and (1a") can be prepared in particular as described in patent WO03028721A2, but using respectively a 3,4-diaminophenyl sulphide of formulae (H') and (H") and a pseudo thiourea of formula (J), in the presence of acetic acid and in a protic solvent such as methanol, at a temperature in the region of 80° C.

More particularly, the benzimidazoles of general formulae (1b') and (1b") can be prepared respectively by reaction of an amine NHR1R2 of formula (R) (with R1 and R2 as defined above) with a carbamate of formulae (1a') and (1a"), for example in the presence of an aprotic solvent such as 1-methyl-2-pyrrolidinone. The reaction is carried out, for example, at a temperature in the region of 120° C., in a sealed tube under microwaves.

More particularly, the 2-amino benzimidazoles of general formulae (1c') and (1c") can be prepared, for example, by reaction of cyanogen bromide with a compound of formulae respectively (H') and (H"), in the presence of a protic solvent such as ethanol. The reaction is carried out at a temperature in the region of 80° C.

More particularly, the general carbamates of formulae (1d') and (1d") can be obtained by reaction with a chlorocarbonate of formula (O) (X=Cl) on a compound of general formulae respectively (1c') and (1c"), for example in a solvent such as tetrahydrofuran, in the presence of a base such as sodium hydrogen carbonate at a temperature in the region of 20° C.

More particularly, the carboxamides (1e') and (1e") can be obtained respectively from the amines of general formulae (1c') and (1c")

- by reaction of the amines (1c') and (1c") with an acid chloride of formula (P) (X=Cl), in the presence, for example, of a solvent such as pyridine, at a temperature in the region of 20° C.
- by reaction of the amines (1c') and (1c") with an acid anhydride of formula (P) (X=OCOR7), in the presence, for example, of a solvent such as pyridine at a temperature in the region of 20° C.
- by coupling of the amines (1c') and (1c") with an acid of formula (P) (X=OH) under the conditions described, for example, by D. D. DesMarteau; V. Montanari (Chem Lett, 2000 (9), 1052), in the presence of 1-hydroxybenzotriazole and 1-(3-dimethylaminopropyl)-3-ethylcarbodiimide and in the presence of a base such as triethylamine, at a temperature in the region of 40° C.

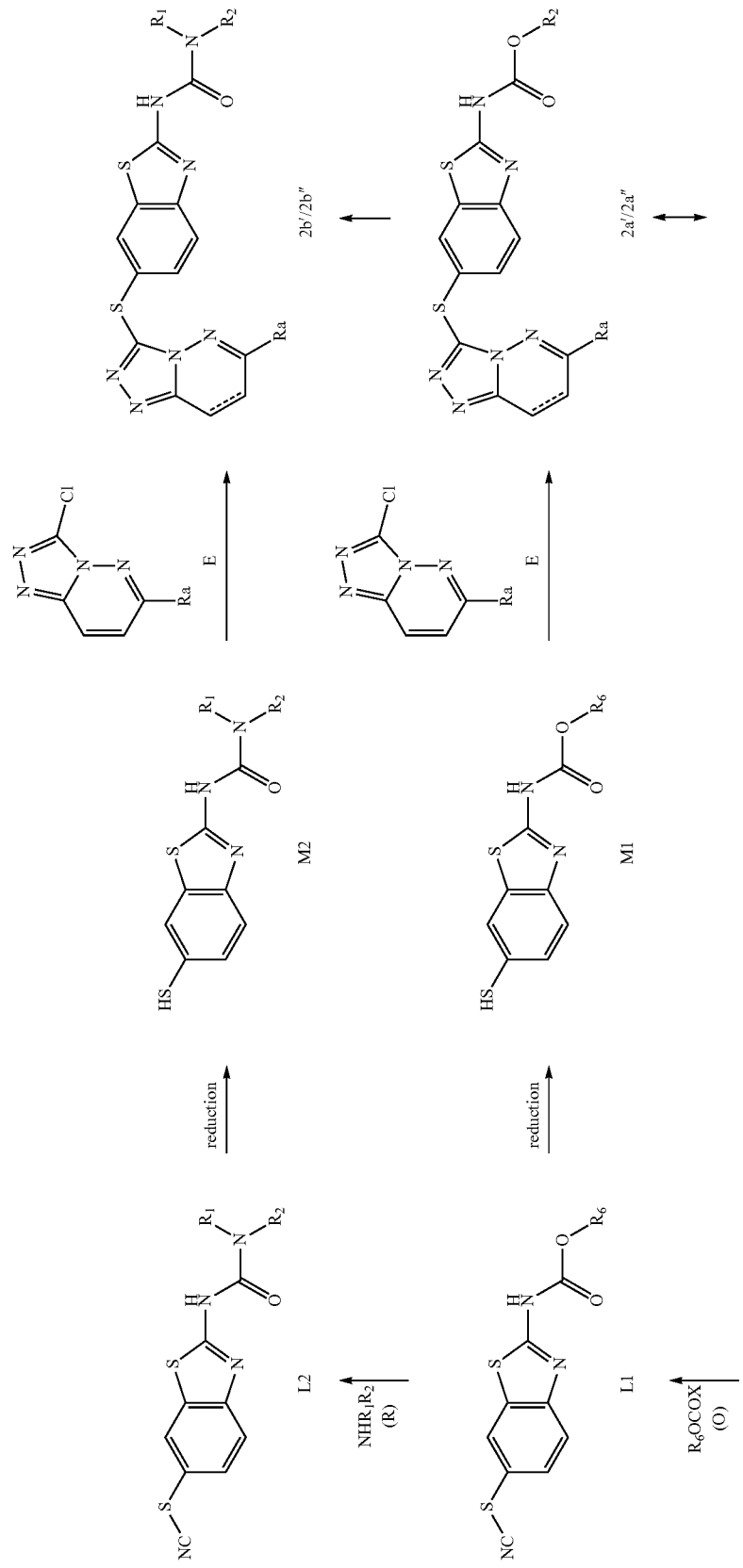
Scheme 2: Synthesis of benzothiazole derivatives of formulae (2a'), (2b'), (2c'), (2d'), (2a'), (2b'), (2c'), (2d')

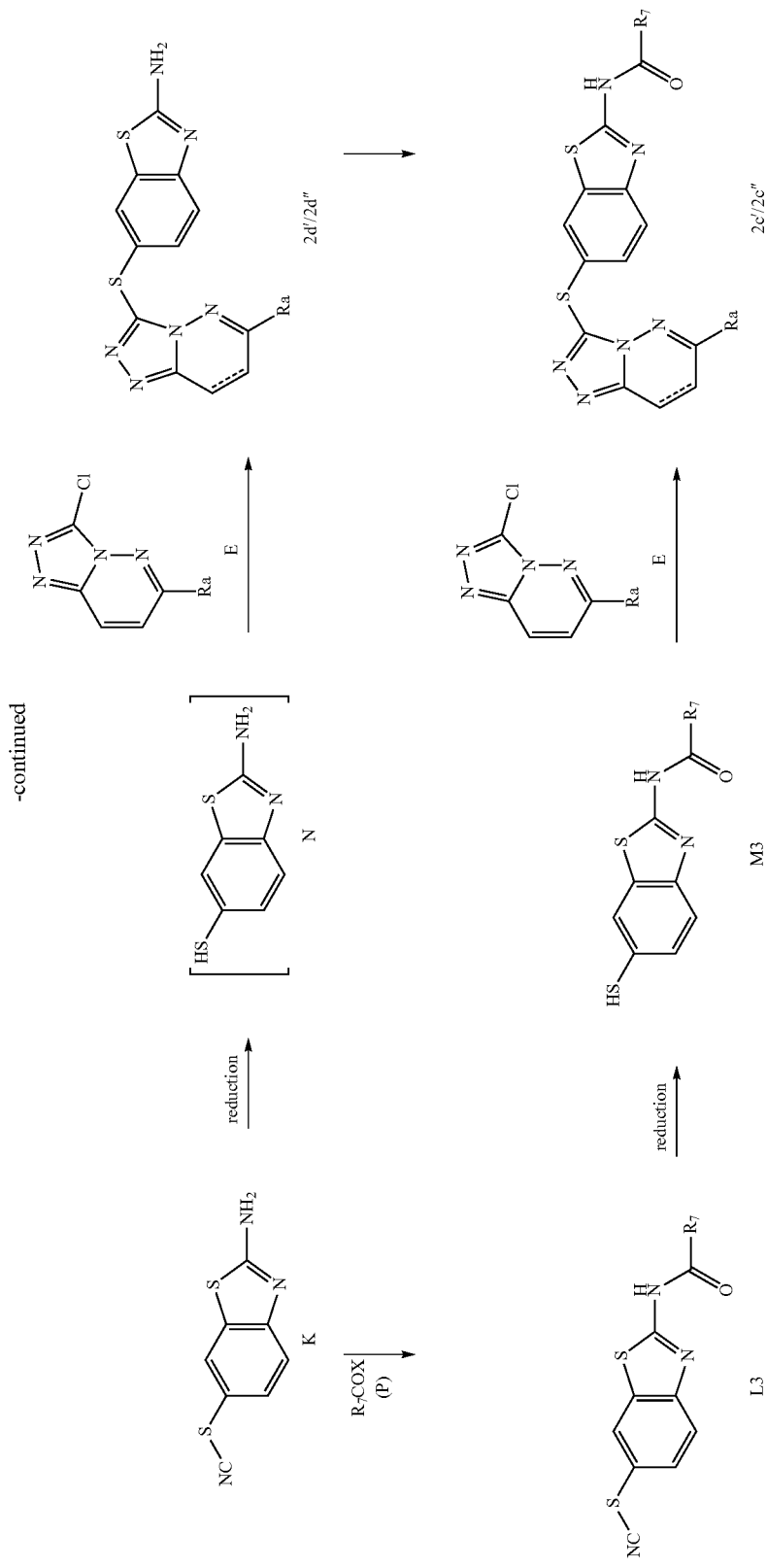

In scheme 2 above, the substituents Ra, R1 and R2 have the meanings indicated above for the products of formulae (I') and (I") and the substituent R6, in the compounds of formulae (O), (L1), (M1) and (2a')/(2a"), represents an alkyl radical optionally substituted with an NR3R4 (a —(CH$_2$)$_n$—NR3R4 radical), alkoxy, hydroxyl, heterocycloalkyl, phenyl or —(CH$_2$)$_n$-phenyl group, with phenyl being optionally substituted and n representing an integer from 1 to 4, such that OR6 represents the corresponding values of R as defined above for the products of formulae (I') and (I"). The substituent R7 in the compounds of formulae (M3), (L3), (P) and (2c')/(2c") represents a cycloalkyl or alkyl radical optionally substituted with an NR3R4, alkoxy or hydroxyl radical or a phenyl, heteroaryl or heterocycloalkyl radical, themselves optionally substituted.

In scheme 2 above, the benzothiazoles of general formulae (2a"), (2b"), (2c") and (2d") and also the reduced analogues thereof of general formulae (2a'), (2b'), (2c') and (2d') can be prepared from 2-amino-1,3-benzothiazol-6-yl thiocyanate (K) (commercial compound).

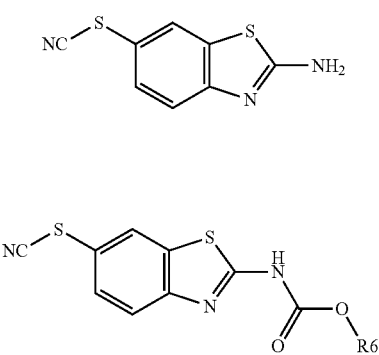

The carbamates of general formula (L1) can be obtained, for example, by reaction with a chlorocarbonate of formula (O) (X=Cl) on 2-amino-1,3-benzothiazol-6-yl thiocyanate (K), in a solvent such as tetrahydrofuran, in the presence of a base such as sodium hydrogen carbonate, at a temperature in the region of 20° C.

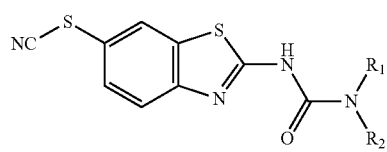

The compounds of general formula (L2) can be obtained, for example, by reaction of the carbamates of formula (L1) where R6=phenyl, with amines NHR1R2 of formula (R) (with R1 and R2 as defined above), in the presence of an aprotic solvent such as tetrahydrofuran, at a temperature in the region of 20° C.

The ureas (2b') and (2b") can be obtained, for example, respectively from the carbamates (2a') and (2a") where R6=phenyl, in the same way as the ureas (L2) are obtained by reaction of amines with the carbamates of type (L1).

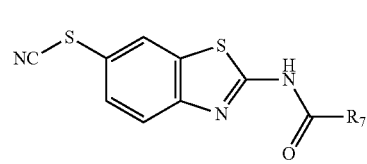

The compounds of general formula (L3) can be obtained, for example:
  by reaction of an acid chloride of formula (P) (X=Cl) with 2-amino-1,3-benzothiazol-6-yl thiocyanate (K), in the presence, for example, of a solvent such as pyridine, at a temperature in the region of 20° C.
  by reaction of an acid anhydride of formula (P) (X=OCOR7) with 2-amino-1,3-benzothiazol-6-yl thiocyanate (K), in the presence, for example, of a solvent such as pyridine, at a temperature in the region of 20° C.
  by coupling of 2-amino-1,3-benzothiazol-6-yl thiocyanate (K) with an acid of formula (P) (X=OH) under the conditions described, for example, by D. D. DesMarteau; V. Montanari (Chem Lett, 2000 (9), 1052), in the presence of 1-hydroxybenzotriazole and 1-(3-dimethylaminopropyl)-3-ethylcarbodiimide and in the presence of a base such as triethylamine, at a temperature in the region of 40° C.

In the same way as the carboxamides (L3) can be obtained by acylation of the amine (K), the carboxamides (2c') and (2c") can be obtained respectively from the amines (2d') and (2d").

The compounds of general formulae (M1), (M2) and (M3) can be obtained, for example, by reduction of compounds of general formulae (L1), (L2), (L3) with DL-dithiothreitol, in the presence of sodium dihydrogen carbonate, in a solvent such as ethanol and at a temperature in the region of 80° C.

The compound of general formula (N) can be prepared in situ by reduction of the compound of formula (K) so as to give directly the amino derivatives of formulae (2d') and (2d"), for example with sodium borohydride in a solvent such as N,N-dimethylformamide, in the presence of a base such as triethylamine and at a temperature in the region of 95° C. or between 20° C. and 95° C.

More particularly, the benzothiazoles of general formulae (2d') and (2d") can also be prepared respectively from carbamates of formulae (2a') and (2a") where R6=t-butyl, by reaction, for example, with trifluoroacetic acid in a solvent such as dichloromethane, at a temperature in the region of 20° C.

Reciprocally, the benzothiazoles of general formulae (2a') and (2a") can also be prepared from benzothiazoles of formulae respectively (2d') and (2d"), for example by reaction with a chlorocarbonate of formula (O) (X=Cl), in a solvent such as tetrahydrofuran, in the presence of a base such as sodium hydrogen carbonate, at a temperature in the region of 20° C.

More particularly, the benzothiazoles of general formulae (2a"), (2b"), (2c") and (2d") and also the reduced analogues thereof of general formulae (2a'), (2b'), (2c') and (2d') can be prepared, for example:
  1) either by coupling of a compound of formula (E) with derivatives (M1), (M2) and (M3) and (N) generated in situ by reduction of the derivatives (L1), (L2), (L3) and (K) with sodium borohydride, in a solvent such as N,N-dimethylformamide and in the presence of a base such as triethylamine, at a temperature in the region of 95° C. or else between 50° C. and 95° C.

2) or by coupling of the isolated derivatives (M1), (M2) and (M3) and of a compound of formula (E), in the presence of sodium borohydride in a solvent such as N,N-dimethylformamide and in the presence of a base such as triethylamine, at a temperature in the region of 95° C.
3) or by coupling of the isolated derivatives (M1), (M2) and (M3) and of a compound of formula (E) under the conditions described, for example, by U. Schopfer et al. (Tetrahedron, 2001, 57, 3069) in the presence of n-tributylphosphine, potassium tert-butoxide, tris(dibenzylideneacetone)-dipalladium(0) and bis(2-diphenylphosphinophenyl)ether in a solvent such as toluene at a temperature in the region of 110° C.
4) or by coupling of a compound of formula (E) with derivatives (M1), (M2) and (M3) and (N) generated in situ by reduction of the derivatives (L1), (L2), (L3) and (K) in the presence of DL-dithiothreitol and of sodium dihydrogen carbonate, in a solvent such as ethanol and at a temperature in the region of 80° C.

The reducing conditions 1) and 2) can give products of formulae (2a), (2b), (2c) and (2d) such that ---- represents a single or double bond, whereas the conditions 3) and 4) give products of formula (2a), (2b), (2c) and (2d) such that ---- represents a double bond.

The compounds of formula (E) can be obtained, for example, as indicated in scheme 3 above, from commercial 3,6-dichloro[1,2,4]triazolo[4,3-b]pyridazine of formula (S).

More particularly, the compounds of formula (E) where Ra represents an OR8 radical can be obtained by treatment of 3,6-dichloro[1,2,4]triazolo[4,3-b]pyridazine (S) with an alkoxide of formula (U), at a temperature in the region of 80° C. and in a solvent such as N,N-dimethylformamide.

More particularly, the compounds of formula (E) where Ra represents an NR$_1$R$_2$ radical can be obtained by treatment of 3,6-dichloro[1,2,4]triazolo-[4,3-b]pyridazine (S) with an amine of formula (R), at a temperature in the region of 20° C. and in a solvent such as N,N-dimethylformamide, or, in the case where NR1R2 is NH$_2$, with aqueous ammonia, in a solvent such as dioxane, in a sealed tube, at a temperature of between 70° C. and 90° C.

More particularly, the compounds of formula (E) where Ra represents an NHCOR7 radical can be obtained by reaction of a compound of general formula (E), with Ra=NH$_2$, with a compound of formula (P) as described for the compounds of general formulae (L3), (1e') and (1e").

More particularly, the compounds of formula (E) where Ra represents an aryl or heteroaryl radical can be obtained, for example:

Scheme 3: Other pathways for synthesizing the triazolopyridazine derivatives of formula (E)

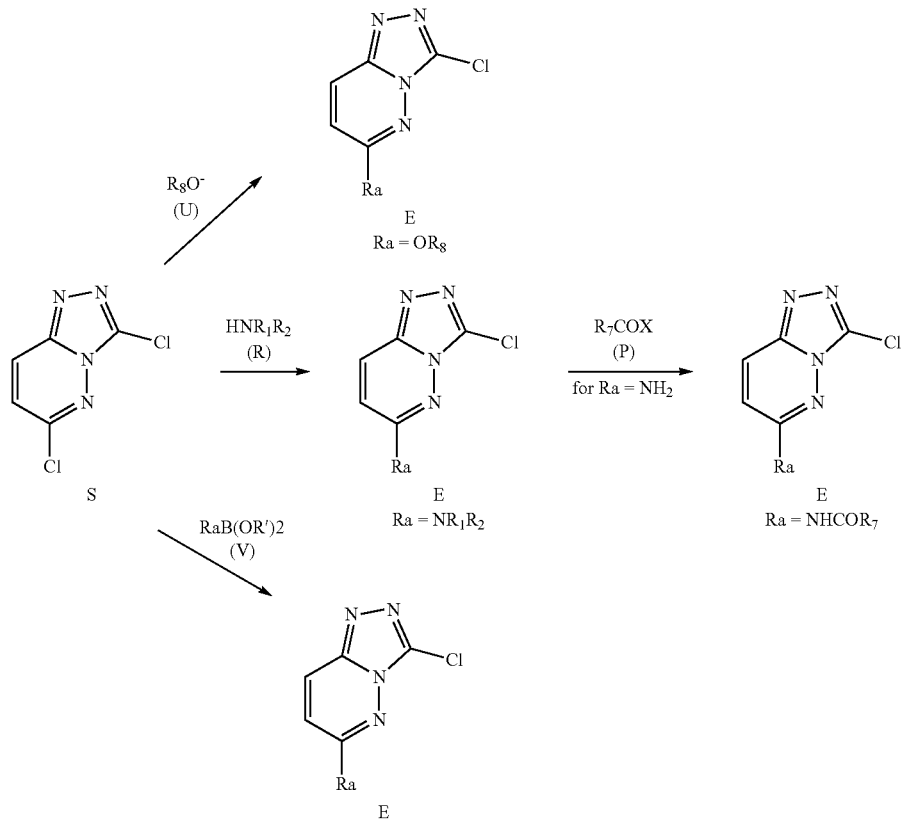

In scheme 3 above, the substituents Ra, R1 and R2 have the meanings indicated above for the products of formulae (1') and (1"). The substituent R7 represents an alkyl or cycloalkyl radical.

The substituent R8 represents:
either an alkyl radical optionally substituted with a chlorine atom, a hydroxyl radical or a heterocycloalkyl radical itself optionally substituted,
or a cycloalkyl radical.

from the boronic acids of formula (V) (R'=H), in the presence of barium hydroxide octahydrate and (1,1'-bis(diphenylphosphino)ferrocene)dichloropalladium(II) in a solvent such as, for example, N,N-dimethylformamide, at a temperature in the region of 80° C.;

or, alternatively, from the boronic esters of formula (V), in the presence of palladium dichlorobis(triphenylphosphine) in a solvent such as, for example, 1,2-dimethoxyethane, in the presence of a base such as 1N sodium hydroxide, at a temperature in the region of 80° C.

Scheme 4: Other pathway for synthesizing the 2-aminobenzothiazole derivatives of formula (2d")

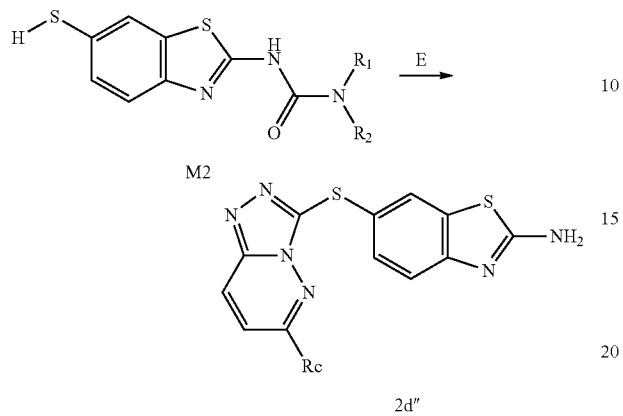

2d"

According to scheme 4 above, the 2-aminobenzothiazoles of general formula (2d") can also be prepared from the compounds of formula (M2) and a compound of formula (E), in the presence of potassium carbonate, in a solvent such as dimethyl sulphoxide. The reaction is carried out, for example, under microwaves, for approximately 10 min, at a temperature in the region of 190° C. In the compound obtained, of formula (2d"), the substituent Rc represents a hydrogen atom or else a heteroaryl radical not attached via a nitrogen atom or else a phenyl radical, these radicals being optionally substituted as indicated above for the substituent Ra.

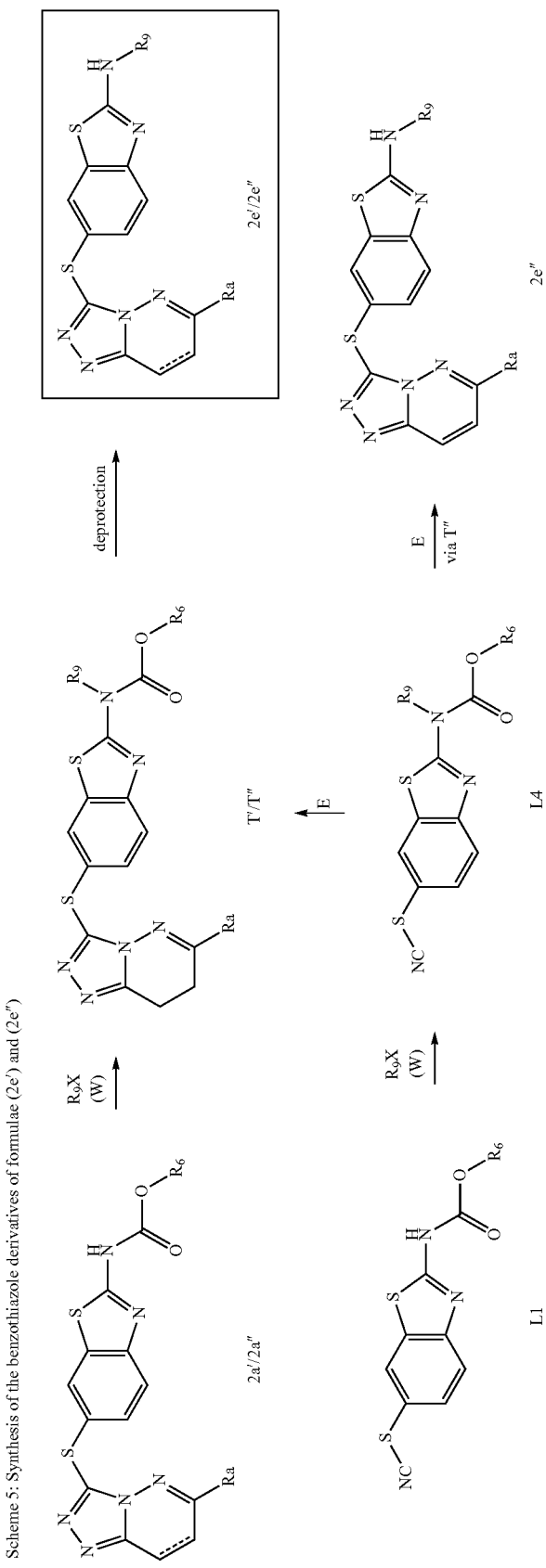
Scheme 5: Synthesis of the benzothiazole derivatives of formulae (2e') and (2e")

According to scheme 5 above, the benzothiazoles of general formulae (2e') and (2e") can be prepared respectively from the compounds of formulae (2a') and (2a").

In scheme 5 above, the substituent OR6 preferably represents O-t-butyl. The substituent R9 represents an alkyl or cycloalkyl radical optionally substituted with an alkoxy, heterocycloalkyl or NR3R4 radical (R3 and R4 as defined above).

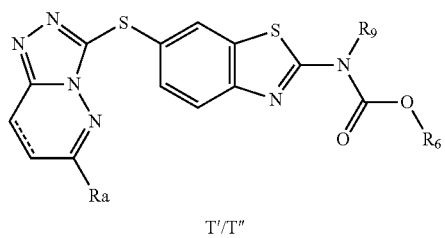

T'/T"

The carbamates of general formula (T') and (T") can be obtained respectively by reaction of carbamates of general formulae (2a') and (2a") with R6=tBu preferably, for example, with alkyl halides of formula (W), in a solvent such as N,N-dimethylformamide, in the presence of sodium hydride, at a temperature of between 20 and 90° C.

The benzothiazoles of general formula (2e') and (2e") can also be prepared from the compounds of formula (L1), preferably with R6=tBu, via the compounds of formulae (T') and (T").

More particularly, the compounds of general formulae (2e') and (2e") can be obtained respectively by treatment of the isolated compounds (T') and (T"), for example, with trifluoroacetic acid, in a solvent such as dichloromethane, at a temperature in the region of 20° C.

Alternatively, the compounds of general formula (2e") can be obtained directly by reaction of the compounds of formulae (L4) and (E), via the compound (T") formed in situ, for example, in the presence of DL-dithiothreitol and sodium dihydrogen carbonate, in a solvent such as ethanol and at a temperature in the region of 80° C., optionally followed by a treatment in situ with trifluoroacetic acid at 20° C. if necessary.

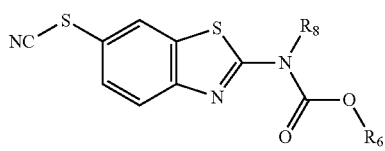

L4

The carbamates of general formula (L4) can be obtained by reaction of carbamates of general formula (L1), for example with alkyl halides of formula (W), in a solvent such as N,N-dimethylformamide, in the presence of sodium hydride, at a temperature of between 20 and 90° C.

Scheme 5a: Synthesis of the benzothiazole derivatives of formulae (2e') and (2e")

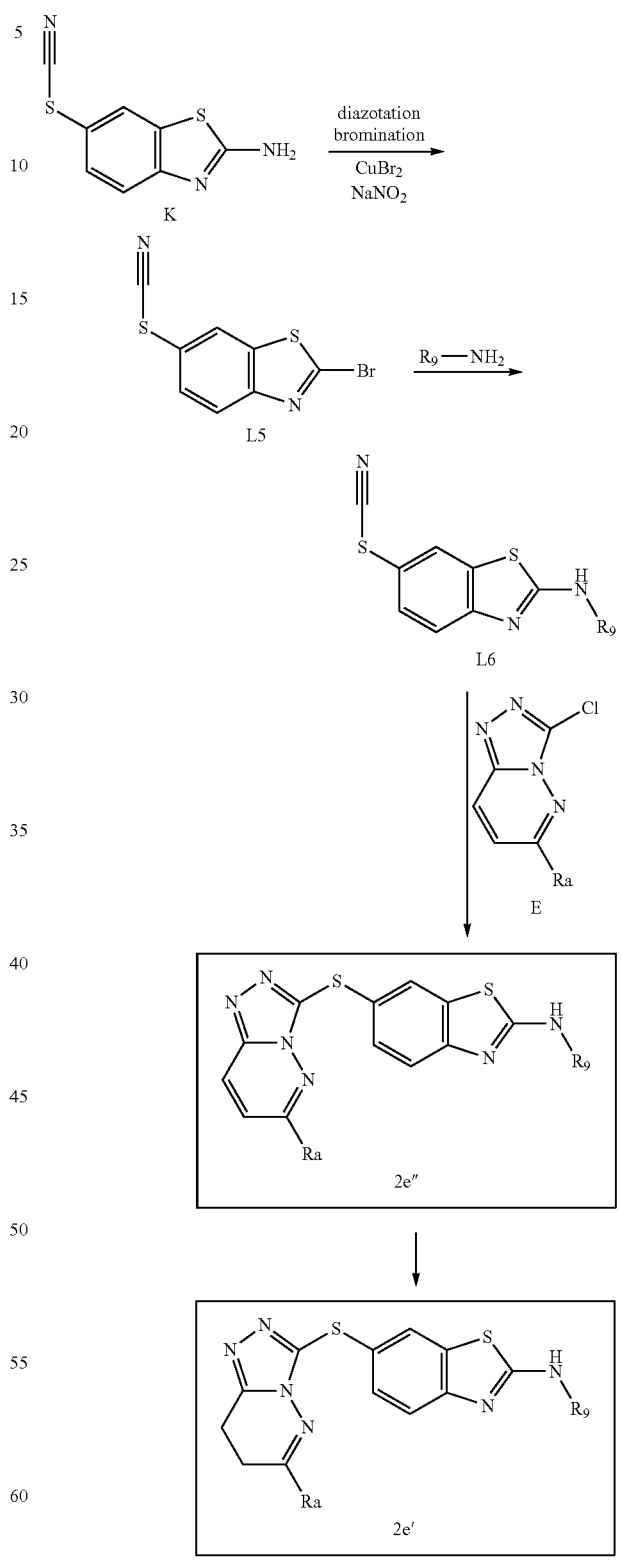

Alternatively, according to scheme 5a above, the benzothiazoles of general formula (2e") can be prepared from the compounds of formulae (L6) and (E), for example in the presence of DL-dithiothreitol and sodium dihydrogen carbonate, in a solvent such as ethanol and at a temperature in the region of 80° C.

The benzothiazoles of general formula (2e') can be prepared from the compounds of formula (2e"), according to the methods described below for preparing the compounds (I') from the compounds (I").

The compounds of formula (L6) can be prepared from the 2-bromobenzo-thiazole derivative (L5) by treatment with an NH2R9 derivative, for example, in a solvent such as tetrahydrofuran, at a temperature in the region of 20° C.

The substituent R9 represents an alkyl or cycloalkyl radical optionally substituted with an alkoxy, heterocycloalkyl or NR3R4 radical (R3 and R4 as defined above).

The compounds of formula (L5) can be prepared from 2-amino-1,3-benzothiazol-6-yl thiocyanate (K) (commercial compound), for example, by treatment with an alkyl nitrite and cuprous bromide in a solvent such as acetonitrile, at a temperature in the region of 0-20° C., according to the method described by Jagabandhu Das et. al., in J. Med. Chem. 2006, 49, 6819-6832.

According to scheme 6 above, the benzothiazoles of general formula (I') can also be prepared, from the compounds of formula (I"), by reduction, for example, with sodium borohydride, in a solvent such as ethanol, at a temperature in the region of 80° C., or else by reduction with zinc(0) in the presence of acetic acid, at a temperature in the region of 20° C.

Alternatively, the compounds (I') can also be prepared from the compounds of formula (E') by coupling with the compounds of type M1, M2, M3 or N, obtained as intermediates by reduction of the compounds L1, L2, L3 or K in situ, as described above in scheme 2. The compounds of type M1, M2 or M3 can also be isolated and used for the coupling with (E'). The compounds (E') can be obtained from the compounds of formula (E) by reduction, for example by reduction with zinc(0) in the presence of acetic acid, at a temperature in the region of 20° C.

Alternatively, the compounds (I') can also be prepared from other compounds (I') by conversion of the group W to a group W' of the same nature as defined above for W and according to reactions of the type defined in scheme 2: con-

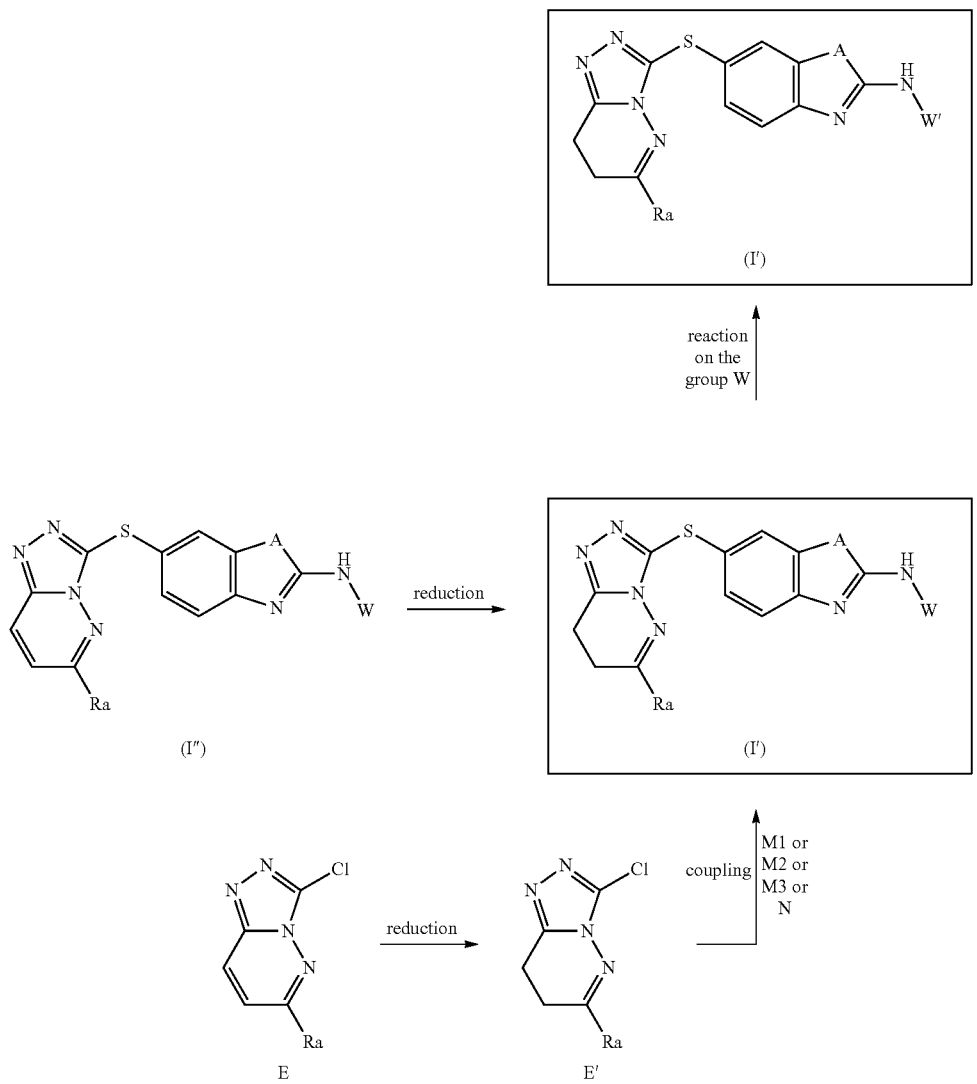

Scheme 6 Other pathways for synthesizing reduced derivatives of formula (I')

versions of 2d'/2d" to 2a'/2a" and to 2c'/2c", conversions of 2a'/2a" to 2d'/2d" and to 2b'/2b".

Scheme 7: Synthesis of benzothiazole N-oxide derivatives of formulae (2f') and (2f")

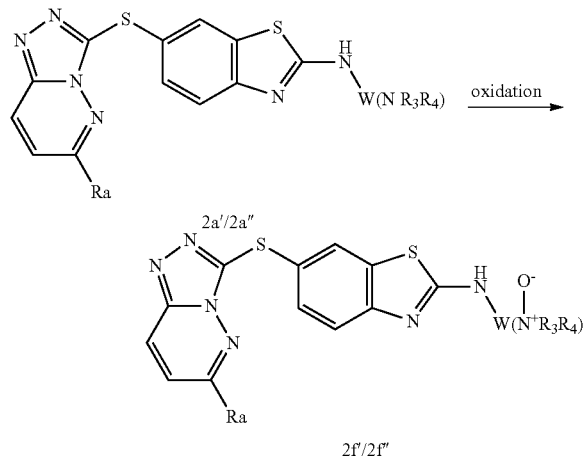

According to scheme 7 above, the benzothiazoles of general formula (2f') and (2f") can be prepared respectively from compounds of formulae (2a') and (2a") in which the substituent W contains a basic function of the NR3R4 type (R3 and R4 as defined above with R3 and R4 different from H), by oxidation, for example, with sodium periodate, in the presence of acetic acid, at a temperature in the region of 20° C.

In the compounds of general Formula (I) as defined above, the sulphur S can be oxidized to sulphoxide SO or sulphone $SO_2$ according to the methods known to those skilled in the art and while protecting, if necessary, the possibly reactive groups with appropriate protecting groups.

Among the starting products of formulae A, B, J, K, O, P, Q, R, S, U, V and W, some are known and can be obtained either commercially, or according to the usual methods known to those skilled in the art, for example starting from commercial products.

It is understood, for those skilled in the art, that, in order to carry out the processes according to the invention described above, it may be necessary to introduce protecting groups for amino, carboxyl and alcohol functions in order to avoid side reactions.

The following non-exhaustive list of examples of protection of reactive functions may be mentioned:
hydroxyl groups may be protected, for example, with alkyl radicals such as tert-butyl, trimethylsilyl, tert-butyldimethylsilyl, methoxymethyl, tetrahydro-pyranyl, benzyl or acetyl,
amino groups may be protected, for example, with acetyl, trityl, benzyl, tert-butoxycarbonyl, BOC, benzyloxycarbonyl or phthalimido radicals or other radicals known in peptide chemistry.

Acid functions may be protected, for example, in the form of esters formed with readily cleavable esters such as benzyl or tert-butyl esters or esters known in peptide chemistry.

A list of various protecting groups that may be used will be found in the textbooks known to those skilled in the art and, for example, in patent BF 2 499 995.

It may be noted that it is possible, if desired and if necessary, to subject intermediate products or products of formula (I) thus obtained by the processes indicated above, in order to obtain other intermediates or other products of formula (I), to one or more conversion reactions known to those skilled in the art, for instance:

a) a reaction for esterification of an acid function,
b) a reaction for saponification of an ester function to an acid function,
c) a reaction for reducing a free or esterified carboxyl function to an alcohol function,
d) a reaction for conversion of an alkoxy function to a hydroxyl function, or alternatively of a hydroxyl function to an alkoxy function,
e) a reaction for removal of the protecting groups that may be borne by the protected reactive functions,
f) a reaction for salification with a mineral or organic acid or with a base so as to obtain the corresponding salt,
g) a reaction for resolution of the racemic forms to resolved products, said products of formula (I) thus obtained being in any of the possible racemic, enantiomeric and diastereoisomeric isomer forms.

The reactions a) to g) can be carried out under the usual conditions known to those skilled in the art, for instance those indicated hereinafter.

a) The products described above may, if desired, undergo, on the possible carboxyl functions, esterification reactions that may be performed according to the usual methods known to those skilled in the art.
b) The possible conversions of ester functions to acid functions of the products described above may be performed, if desired, under the usual conditions known to those skilled in the art, in particular by acid or alkaline hydrolysis, for example with sodium hydroxide or potassium hydroxide in alcoholic medium, for instance in methanol, or alternatively with hydrochloric acid or sulphuric acid.

The saponification reaction may be performed according to the usual methods known to those skilled in the art, for instance in a solvent such as methanol or ethanol, dioxane or dimethoxyethane, in the presence of sodium hydroxide or potassium hydroxide.

c) The possible free or esterified carboxyl functions of the products described above may be reduced, if desired, to alcohol functions via the methods known to those skilled in the art: the possible esterified carboxyl functions may be reduced, if desired, to alcohol functions by the methods known to those skilled in the art, and in particular with lithium aluminium hydride in a solvent, for instance tetrahydrofuran, or dioxane or ethyl ether.

The possible free carboxyl functions of the products described above may be reduced, if desired, to alcohol functions, in particular with boron hydride.

d) The possible alkoxy functions, such as in particular methoxy, of the products described above may be converted, if desired, into hydroxyl functions under the usual conditions known to those skilled in the art, for example with boron tribromide in a solvent such as, for example, methylene chloride, with pyridine hydrochloride or hydrobromide, or alternatively with hydrobromic or hydrochloric acid in water or trifluoroacetic acid at reflux.

e) The removal of protecting groups, for instance those indicated above, may be performed under the usual conditions known to those skilled in the art, in particular via an acid hydrolysis performed with an acid such as hydrochloric acid, benzenesulphonic acid or para-toluenesulphonic acid, formic acid or trifluoroacetic acid, or alternatively via catalytic hydrogenation.

The phthalimido group may be removed with hydrazine.

f) The products described above may undergo, if desired, salification reactions, for example with a mineral or organic acid or with a mineral or organic base according to the usual methods known to those skilled in the art: such a salification reaction may be performed, for example, in the presence of hydrochloric acid, or alternatively of tartaric acid, citric acid or methanesulphonic acid, in an alcohol, for instance ethanol or methanol.

g) The possible optically active forms of the products described above may be prepared by resolution of the racemic mixtures according to the usual methods known to those skilled in the art.

The products of formula (I) as defined above and also the addition salts thereof with acids show advantageous pharmacological properties, in particular on account of their kinase-inhibiting properties as indicated above.

The products of the present invention can in particular be used for treating tumours.

The products of the invention may thus also increase the therapeutic effects of commonly used antitumour agents.

These properties justify their therapeutic use, and a subject of the invention is in particular, as medicaments, the products of formula (I) as defined above, said products of formula (I) being in any of the possible racemic, enantiomeric and diastereoisomeric isomer forms, and also the addition salts with pharmaceutically acceptable mineral and organic acids or with pharmaceutically acceptable mineral and organic bases of said products of formula (I).

A subject of the invention is most particularly, as medicaments, the products corresponding to the following formulae:

methyl (6-{[6-(4-fluorophenyl)[1,2,4]triazolo[4,3-b]pyridazin-3-yl]sulphanyl}-1,3-benzothiazol-2-yl)carbamate
6-{[6-(4-fluorophenyl)[1,2,4]triazolo[4,3-b]pyridazin-3-yl]sulphanyl}-1,3-benzothiazol-2-amine
methyl (6-{[6-(4-fluorophenyl)[1,2,4]triazolo[4,3-b]pyridazin-3-yl]sulphanyl}-1H-benzimidazol-2-yl)carbamate
1-(6-{[6-(4-fluorophenyl)[1,2,4]triazolo[4,3-b]pyridazin-3-yl]sulphanyl}-1H-benzimidazol-2-yl)-3-(2-morpholin-4-ylethyl)urea
6-{[6-(4-fluorophenyl)[1,2,4]triazolo[4,3-b]pyridazin-3-yl]sulphanyl}-1H-benzimidazol-2-amine
1-(2-morpholin-4-ylethyl)-3-[6-([1,2,4]triazolo[4,3-b]pyridazin-3-ylsulphanyl)-1,3-benzothiazol-2-yl]urea
1-(6-{[6-(4-fluorophenyl)[1,2,4]triazolo[4,3-b]pyridazin-3-yl]sulphanyl}-1,3-benzothiazol-2-yl)-3-(2-morpholin-4-ylethyl)urea
1-{2-[(2R,6S)-2,6-dimethylmorpholin-4-yl]ethyl}-3-(6-{[6-(4-fluorophenyl)-[1,2,4]triazolo[4,3-b]pyridazin-3-yl]sulphanyl}-1,3-benzothiazol-2-yl)urea
(6-{[6-(4-fluorophenyl)[1,2,4]triazolo[4,3-b]pyridazin-3-yl]sulphanyl}-1,3-benzothiazol-2-yl)carbamate of 2-morpholin-4-ylethyl
1-(6-{[6-(4-fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea
N-(6-{[6-(4-fluorophenyl)[1,2,4]triazolo[4,3-b]pyridazin-3-yl]sulphanyl}-1,3-benzothiazol-2-yl)-4-morpholin-4-ylbutanamide
1-[2-(diethylamino)ethyl]-3-(6-{[6-(4-fluorophenyl)[1,2,4]triazolo[4,3-b]pyridazin-3-yl]sulphanyl}-1,3-benzothiazol-2-yl)urea
1-{6-[(6-methoxy[1,2,4]triazolo[4,3-b]pyridazin-3-yl)sulphanyl]-1,3-benzothiazol-2-yl}-3-[2-(morpholin-4-yl)ethyl]urea
N-[6-({6-[(2-methoxyethyl)amino][1,2,4]triazolo[4,3-b]pyridazin-3-yl}sulphanyl)-1,3-benzothiazol-2-yl]acetamide
6-{[6-(4-fluorophenyl)[1,2,4]triazolo[4,3-b]pyridazin-3-yl]sulphanyl}-N-[2-(morpholin-4-yl)ethyl]-1,3-benzothiazol-2-amine
phenyl 6-{[6-(4-fluorophenyl)[1,2,4]triazolo[4,3-b]pyridazin-3-yl]sulphanyl}-1,3-benzothiazol-2-yl)carbamate
1-{6-[(6-ethoxy[1,2,4]triazolo[4,3-b]pyridazin-3-yl)sulphanyl]-1,3-benzothiazol-2-yl}-3-[2-(morpholin-4-yl)ethyl]urea
1-{6-[(6-ethoxy-7,8-dihydro[1,2,4]triazolo[4,3-b]pyridazin-3-yl)sulphanyl]-1,3-benzothiazol-2-yl}-3-[2-(morpholin-4-yl)ethyl]urea
N-[6-({6-[(2-methoxyethyl)amino][1,2,4]triazolo[4,3-b]pyridazin-3-yl}sulphanyl)-1,3-benzothiazol-2-yl]cyclopropanecarboxamide
1-(6-{[6-(4-fluorophenyl)[1,2,4]triazolo[4,3-b]pyridazin-3-yl]sulphanyl}-1,3-benzothiazol-2-yl)-3-[2-(4-oxidomorpholin-4-yl)ethyl]urea
6-{[6-(1H-pyrazol-4-yl)[1,2,4]triazolo[4,3-b]pyridazin-3-yl]sulphanyl}-1,3-benzothiazol-2-amine
1-(6-{[6-(4-fluorophenyl)-7,8-dihydro-[1,2,4]triazolo[4,3-b]pyridazin-3-yl]sulphanyl}-1,3-benzothiazol-2-yl)-3-[2-(morpholin-4-yl)ethyl]urea
oxetan-2-ylmethyl (6-{[6-(4-fluorophenyl)[1,2,4]triazolo[4,3-b]pyridazin-3-yl]sulphanyl}-1,3-benzothiazol-2-yl)carbamate
N-{6-[(6-methoxy[1,2,4]triazolo[4,3-b]pyridazin-3-yl)sulphanyl]-1,3-benzothiazol-2-yl}cyclopropanecarboxamide
N-(6-{[6-(4-fluorophenyl)[1,2,4]triazolo[4,3-b]pyridazin-3-yl]sulphanyl}-1,3-benzothiazol-2-yl)acetamide
1-{6-[(6-methoxy[1,2,4]triazolo[4,3-b]pyridazin-3-yl)sulphanyl]-1,3-benzothiazol-2-yl}-3-[2-(pyrrolidin-1-yl)ethyl]urea
6-[(6-ethoxy[1,2,4]triazolo[4,3-b]pyridazin-3-yl)sulphanyl]-1,3-benzothiazol-2-amine
6-{[6-(3-fluorophenyl)[1,2,4]triazolo[4,3-b]pyridazin-3-yl]sulphanyl}-1,3-benzothiazol-2-amine
1-cyclopropyl-3-{6-[(6-ethoxy[1,2,4]triazolo[4,3-b]pyridazin-3-yl)sulphanyl]-1,3-benzothiazol-2-yl}urea
N-(6-{[6-(4-fluorophenyl)[1,2,4]triazolo[4,3-b]pyridazin-3-yl]sulphanyl}-1,3-benzothiazol-2-yl)cyclopropanecarboxamide
N-(6-{[6-(4-fluorophenyl)-7,8-dihydro[1,2,4]triazolo[4,3-b]pyridazin-3-yl]sulphanyl}-1,3-benzothiazol-2-yl)cyclopropanecarboxamide
1-(6-{[6-(3-fluorophenyl)[1,2,4]triazolo[4,3-b]pyridazin-3-yl]sulphanyl}-1,3-benzothiazol-2-yl)-3-[2-(morpholin-4-yl)ethyl]urea and also the addition salts with pharmaceutically acceptable mineral and organic acids or with pharmaceutically acceptable mineral and organic bases of said products of formula (I).

The invention also relates to pharmaceutical compositions containing, as active ingredient, at least one of the products of formula (I) as defined above or a pharmaceutically acceptable salt of this product or a prodrug of this product and, where appropriate, a pharmaceutically acceptable carrier.

The invention thus covers the pharmaceutical compositions containing, as active ingredient, at least one of the medicaments as defined above.

Such pharmaceutical compositions of the present invention may also, where appropriate, contain active ingredients of other antimitotic medicaments, such as in particular those based on taxol, cisplatin, DNA intercalating agents, and the like.

These pharmaceutical compositions may be administered orally, parenterally or locally by topical application to the skin and the mucous membranes or by intravenous or intramuscular injection.

These compositions may be solid or liquid and may be in any pharmaceutical form commonly used in human medicine, for instance simple or sugar-coated tablets, pills, lozenges, gel capsules, drops, granules, injectable preparations, ointments, creams or gels; they are prepared according to the usual methods. The active ingredient may be incorporated therein into excipients normally used in these pharmaceutical compositions, such as talc, gum arabic, lactose, starch, magnesium stearate, cocoa butter, aqueous or nonaqueous carriers, fatty substances of animal or plant origin, paraffinic derivatives, glycols, various wetting agents, dispersants or emulsifiers, and preservatives.

The usual dosage, which is variable depending on the product used, the individual treated and the condition in question, may be, for example, from 0.05 to 5 g per day in adults, or preferably from 0.1 to 2 g per day.

A subject of the invention is also the use of the products of formula (I) as defined above or of pharmaceutically acceptable salts of these products for the preparation of a medicament for use in inhibiting the activity of a protein kinase.

A subject of the present invention is also the use of products of formula (I) as defined above for the preparation of a medicament for use in the treatment or prevention of a disease characterized by deregulation of the activity of a protein kinase.

Such a medicament may in particular be for use in the treatment or prevention of a disease in a mammal.

A subject of the present invention is also the use defined above, in which the protein kinase is a protein tyrosine kinase.

A subject of the present invention is also the use defined above, in which the protein tyrosine kinase is MET or mutant forms thereof.

A subject of the present invention is also the use defined above, in which the protein kinase is in a cell culture.

A subject of the present invention is also the use defined above, in which the protein kinase is in a mammal.

A subject of the present invention is in particular the use of a product of formula (I) as defined above for the preparation of a medicament for use in the prevention or treatment of diseases associated with an uncontrolled proliferation.

A subject of the present invention is in particular the use of a product of formula (I) as defined above for the preparation of a medicament for use in the treatment or prevention of a disease chosen from the following group: blood vessel proliferation disorders, fibrotic disorders, 'mesangial' cell proliferation disorders, metabolic disorders, allergies, asthma, thrombosis, nervous system diseases, retinopathy, psoriasis, rheumatoid arthritis, diabetes, muscle degeneration and cancers.

A subject of the present invention is thus most particularly the use of a product of formula (I) as defined above for the preparation of a medicament for use in the treatment or prevention of diseases in oncology and in particular for use in the treatment of cancers.

Among these cancers, the treatment of solid or liquid tumours and the treatment of cancers that are resistant to cytotoxic agents are of interest.

The cited products of the present invention may in particular be used for the treatment of primary tumours and/or metastases, in particular in gastric, hepatic, renal, ovarian, colon, prostate and lung (NSCLC and SCLC) cancers, glioblastomas, thyroid, bladder or breast cancers, in melanomas, in lymphoid or myeloid haematopoietic tumours, in sarcomas, in brain, larynx or lymphatic system cancers, bone cancers and pancreatic cancers.

A subject of the present invention is also the use of the products of formula (I) as defined above for the preparation of medicaments for use in cancer chemotherapy.

Such medicaments for use in cancer chemotherapy may be used alone or in combination.

The products of the present application may in particular be administered alone or in combination with chemotherapy or radiotherapy or alternatively in combination, for example, with other therapeutic agents.

Such therapeutic agents may be commonly used antitumour agents.

As kinase inhibitors, mention may be made of butyrolactone, flavopiridol and 2(2-hydroxyethylamino)-6-benzylamino-9-methylpurine, also known as olomucine.

A subject of the present invention is also, as new industrial products, the synthesis intermediates of formulae E', M1, M2, M3 and N as defined above and recalled hereinafter:

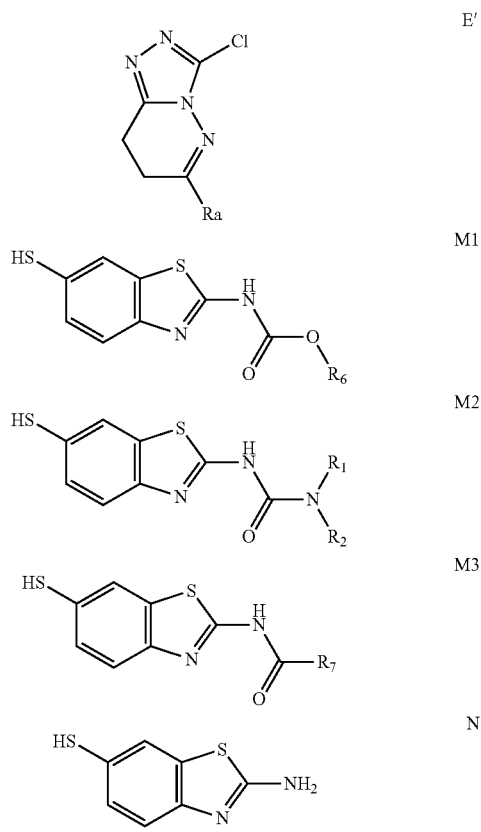

in which R6 represents an alkyl radical optionally substituted with an NR3R4 (a —(CH$_2$)$_n$—NR3R4 radical), alkoxy, hydroxyl, heterocycloalkyl, phenyl or —(CH$_2$)$_n$-phenyl group, with phenyl being optionally substituted and n representing an integer from 1 to 4, such that OR6 represents the corresponding values of R as defined above; R7 represents a cycloalkyl or alkyl radical optionally substituted with an NR3R4, alkoxy or hydroxyl radical or a phenyl, heteroaryl or heterocycloalkyl radical, themselves optionally substituted as indicated above; and Ra, R1, R2, R3 and R4 have the meanings indicated above.

The following examples, which are products of formula (I), illustrate the invention without, however, limiting it.

EXPERIMENTAL SECTION

The nomenclature of the compounds of the present invention was carried out with the ACDLABS software version 10.0.

Microwave oven used:
Biotage, Initiator EXP-EU, 300 W max, 2450 MHz

The $^1$H NMR spectrum at 400 MHz and $^1$H NMR spectrum at 300 MHz were acquired on a Bruker Avance DRX-400 or Bruker Avance DPX-300 spectrometer with the chemical shifts (δ in ppm) in the solvent d6-dimethyl sulphoxide (d6-DMSO) referenced to 2.5 ppm at a temperature of 303 K.

The mass spectra were acquired either by:
LC-MS-DAD-ELSD analysis (MS=Waters ZQ), or
LC-MS-DAD-ELSD analysis (MS=Platform II Waters Micromass) or
UPLC-MS-DAD-ELSD analysis (MS=Quattro Premier XE Waters).

DAD considered wavelength λ=210-400 nm
ELSD: Sedere SEDEX 85; nebulization temperature=35° C.; nebulization pressure=3.7 bar.

EXAMPLE 1

Methyl (6-{[6-(4-fluorophenyl)[1,2,4]triazolo[4,3-b]pyridazin-3-yl]sulphanyl}-1,3-benzothiazol-2-yl)carbamate a) The methyl (6-{[6-(4-fluorophenyl)[1,2,4]triazolo[4,3-b]pyridazin-3-yl]sulphanyl}-1,3-benzothiazol-2-yl)carbamate can be prepared in the following way:

0.14 cm$^3$ of triethylamine and 31 mg of sodium borohydride are added to a suspension of 242 mg of 3-chloro-6-(4-fluorophenyl)-1,2,4-triazolo[4,3-b]pyridazine and 100 mg of methyl (6-sulphanyl-1,3-benzothiazol-2-yl)carbamate in 3 cm$^3$ of N,N-dimethylformamide at 20° C. The partially soluble violet-brown suspension is stirred at 95° C. for 2 h. The solution is cooled to 20° C. and then taken up in a 50/50 mixture of water and ethyl acetate. The resulting suspension is spin-filter-dried so as to give 155 mg of a creamy-white insoluble material which contains expected product with 70% of methyl (6-sulphanyl-1,3-benzothiazol-2-yl)carbamate. Extraction of the mother liquors with ethyl acetate, followed by drying of the organic phases over magnesium sulphate, filtration and concentration to dryness in a rotary evaporator gives a semicrystalline oil which is subsequently filtered. 48 mg of a white powder containing >80% of methyl (6-{[6-(4-fluorophenyl)[1,2,4]triazolo[4,3-b]pyridazin-3-yl]sulphanyl}-1,3-benzothiazol-2-yl)carbamate are thus obtained.

The 155 mg of product containing 70% of methyl (6-sulphanyl-1,3-benzothiazol-2-yl)carbamate are reacted with 50 mg of 3-chloro-6-(4-fluorophenyl)-1,2,4-triazolo[4,3-b]pyridazine in N,N-dimethylformamide containing 0.07 cm$^3$ of triethylamine and 15 mg of sodium borohydride. The partially soluble violet-brown suspension is stirred at 95° C. for 2 h. The solution is cooled to 20° C. and then taken up in a 50/50 mixture of water and ethyl acetate. The resulting suspension is filtered so as to give 112 mg of a creamy-white insoluble material containing the methyl (6-{[6-(4-fluorophenyl)[1,2,4]triazolo[4,3-b]pyridazin-3-yl]sulphanyl}-1,3-benzothiazol-2-yl)carbamate.

The batches of 48 mg and of 112 mg are combined and purified by chromatography on a Biotage Si 12M+ column, elution being carried out with a 95/5 then 90/10 gradient of dichloromethane and of a 38/17/2 solution of dichloromethane/methanol/aqueous ammonia.

56 mg of methyl (6-{[6-(4-fluorophenyl)[1,2,4]triazolo[4,3-b]pyridazin-3-yl]sulphanyl}-1,3-benzothiazol-2-yl)carbamate are obtained in the form of a white powder, the characteristics of which are as follows:

MELTING POINT>270° C. (Köfler block)
$^1$H NMR SPECTRUM (400 MHz, δ ppm) (d6-DMSO): 3.78 (s, 3H); 7.40 (t, J=9.0 Hz, 2H); 7.54 (dd, J=2.0 and 8.0 Hz, 1H); 7.65 (d, J=8.0 Hz, 1H); 8.03 (d, J=9.5 Hz, 1H); 8.10 (dd, J=5.0 and 9.0 Hz, 2H); 8.21 (d, J=2.0 Hz, 1H); 8.51 (d, J=9.5 Hz, 1H); 12.15 (broad m, 1H).
MASS SPECTRUM: LC-MS-DAD-ELSD: 451(−)=(M−H)(−); 453(+)=(M+H)(+).

b) The methyl (6-sulphanyl-1,3-benzothiazol-2-yl)carbamate can be prepared in the following way:

a solution of 5 mg of potassium dihydrogen phosphate in 1.1 cm$^3$ of water at 20° C., followed by 480 mg of DL-dithiothreitol, are added to a white suspension of 280 mg of methyl (6-thiocyanato-1,3-benzothiazol-2-yl)-carbamate in 11 cm$^3$ of ethanol at 20° C. The white suspension is stirred for 18 h at reflux. The reaction mixture is cooled to 20° C., then 10 cm$^3$ of water are added and the mixture is stirred for 15 minutes. The precipitate is spin-filter-dried and then washed with large volumes of water. 231 mg of methyl (6-sulphanyl-1,3-benzothiazol-2-yl)carbamate are obtained in the form of a cream powder, the characteristics of which are as follows:

MASS SPECTRUM: LC-MS-DAD-ELSD: 239(−)=(M−H)(−); 241(+)=(M+H)(+).

c) The methyl (6-thiocyanato-1,3-benzothiazol-2-yl)carbamate can be prepared in the following way:

0.467 cm$^3$ of methyl chlorocarbonate is added, with a syringe, while maintaining the temperature at 0° C., to a green solution of 1 g of commercial 2-amino-1,3-benzothiazol-6-ylthiocyanate in 12 cm$^3$ of pyridine at 0° C. The suspension is stirred for 2 h at 20° C. before the addition of 6 cm$^3$ of a 50/50 mixture of water and ethyl acetate. The white powder obtained is filtered on a frit and then washed successively with water and with ethyl acetate.

816 mg of a white powder of methyl (6-thiocyanato-1,3-benzothiazol-2-yl)carbamate are obtained in the form of a white powder, the characteristics of which are as follows:

MASS SPECTRUM: LC-MS-DAD-ELSD: 264(−)=(M−H)(−); 266(+)=(M+H)(+).

d) The 3-chloro-6-(4-fluorophenyl)-1,2,4-triazolo[4,3-b]pyridazine can be prepared in the following way:

700 mg of 6-(4-fluorophenyl)-1,2,4-triazolo[4,3-b]pyridazin-3-ol and 3.5 cm$^3$ of phosphorus oxychloride are introduced, at 20° C., into a microwave tube equipped with a magnetic stirrer. The reaction mixture is then heated in the microwave for 1 h at 150° C. before the addition of 100 cm$^3$ of a saturated aqueous solution of sodium hydrogen carbonate and then the further addition of sodium hydrogen carbonate to neutralize the medium. The mixture obtained is extracted with 3×100 cm$^3$ of ethyl acetate. The organic phases are combined and then dried over magnesium sulphate and concentrated to dryness, to give 696 mg of an orange solid that is chromatographed on a 40 g Analogix cartridge of silica 50 µm (elution with pure dichloromethane then with an 80/20 mixture of dichloromethane/ethyl acetate). 597 mg of 3-chloro-6-(4-fluorophenyl)-1,2,4-triazolo[4,3-b]pyridazine are thus obtained in the form of a beige solid, the characteristics of which are as follows:

$^1$H NMR SPECTRUM (400 MHz; δ ppm) (d6-DMSO): 7.47 (t, J=9.0 Hz, 2H); 8.07 (d, J=9.5 Hz, 1H); 8.21 (dd, J=5.0 and 9.0 Hz, 2H); 8.51 (d, J=9.5 Hz, 1H).

MASS SPECTRUM: LC-MS-DAD-ELSD: 249(+)/=(M+H)(+)/(1Cl present).

e) The 6-(4-fluorophenyl)-1,2,4-triazolo[4,3-b]pyridazin-3-ol can be prepared in the following way:

4.6 g of hydrazinecarboxamide hydrochloride and 5.7 cm$^3$ of triethylamine are added to a mixture of 4.3 g of 3-chloro-6-(4-fluorophenyl)pyridazine in 70 cm$^3$ of butanol, at 20° C. The resulting mixture is heated at 140° C. for 65 h and then cooled to 20° C. before the addition of 300 cm$^3$ of dichloromethane. The reaction mixture is then washed with 150 cm$^3$ of demineralized water. The organic phases are subsequently combined and then dried over magnesium sulphate and concentrated to dryness, to give 4.93 g of an orange solid. This solid is then taken up in diethyl ether, and then spin-filter-dried, to give 2.5 g of 6-(4-fluorophenyl)-1,2,4-triazolo[4,3-b]pyridazin-3-ol in the form of a yellow solid, the characteristics of which are as follows:

MASS SPECTRUM: LC-MS-DAD-ELSD: 231(+)/=(M+H)(+)/(1Cl present).

f) The 3-chloro-6-(4-fluorophenyl)pyridazine can be prepared in the following way:

140 mg of 4-fluorobenzeneboronic acid and 231 mg of sodium hydrogen carbonate in 7 cm$^3$ of demineralized water are added to a solution of 300 mg of commercial 3,6-dichloropyrazine in 12=$^3$ of dioxane. The medium is degassed by sparging with argon for 5 minutes and then 115 mg of tetrakis(triphenylphosphine)palladium(0) are added. The mixture obtained is heated at 115° C. for 1 h 30 and then cooled to 20° C. before the addition of 20 cm$^3$ of demineralized water. The precipitate formed is spin-filter-dried and then washed with demineralized water. After drying, 213 mg of a pink solid are obtained. Extraction of the aqueous phases with 40 cm$^3$ of dichloromethane followed by drying of the organic phase over magnesium sulphate and concentration to dryness, gives 213 mg of a beige powder.

The 2 solids are combined and chromatographed on a 12 g Analogix cartridge of silica 50 μm—(elution: dichloromethane). 285 mg of expected product are thus obtained, and chromatographed again under the same conditions, to give 175 mg of 3-chloro-6-(4-fluorophenyl)pyridazine in the form of a white solid, the characteristics of which are as follows:

MASS SPECTRUM: LC-MS-DAD-ELSD: 209(+)/=(M+H)(+)/(1Cl present).

EXAMPLE 2

1,1-Dimethylethyl (6-{[6-(4-fluorophenyl)[1,2,4]triazolo[4,3-b]pyridazin-3-yl]sulphanyl}-1,3-benzothiazol-2-yl)carbamate a) The 1,1-dimethylethyl (6-{[6-(4-fluorophenyl)[1,2,4]triazolo[4,3-b]pyridazin-3-yl]sulphanyl}-1,3-benzothiazol-2-yl)carbamate can be prepared as in Example 1a, but using 56 mg of 1,1-dimethylethyl (6-sulphanyl-1,3-benzothiazol-2-yl)carbamate and 50 mg of 3-chloro-6-(4-fluorophenyl)-1,2,4-triazolo[4,3-b]pyridazine. Chromatography is carried out on Biotage Quad 12/25 (KP-SIL, 60 A; 32-63 μM), elution being carried out with 95/5 dichloromethane/solution B (solution B=38/17/2 dichloromethane/methanol-/aqueous ammonia). 27 mg of 1,1-dimethylethyl (6-{[6-(4-fluorophenyl)-[1,2,4]triazolo[4,3-b]pyridazin-3-yl]sulphanyl}-1,3-benzothiazol-2-yl)carbamate are obtained in the form of a yellow powder, the characteristics of which are as follows:

MASS SPECTRUM: LC-MS-DAD-ELSD: 495(+)=(M+H)(+).

$^1$H NMR SPECTRUM: (400 MHz, d6-DMSO) δppm 1.50 (s, 9 H) 7.40 (t, J=9 Hz, 2 H) 7.54 (dd, J=8.3, 2.0 Hz, 1H) 7.65 (d, J=8.3 Hz, 1 H) 8.02 (d, J=9.8 Hz, 1 H) 8.10 (dd, J=9.0, 5.6 Hz, 2 H) 8.19 (d, J=2.0 Hz, 1H) 8.51 (d, J=9.8 Hz, 1 H) 11.82 (br, s, 1 H)

b) The 1,1-dimethylethyl (6-sulphanyl-1,3-benzothiazol-2-yl)carbamate can be prepared as in Example 1b, but using 615 mg of 1,1-dimethylethyl (6-thiocyanatobenzothiazol-2-yl)carbamate, 10 mg of potassium dihydrogen phosphate and 926 mg of DL-dithiothreitol. 659 mg of 1,1-dimethylethyl (6-sulphanyl-1,3-benzothiazol-2-yl)carbamate are thus obtained in the form of a white powder, the characteristics of which are as follows:

MASS SPECTRUM: LC-MS-DAD-ELSD: 281(−)=(M−H)(−); 227(+)=(M+H)(−)-tBu.

c) The 1,1-dimethylethyl (6-thiocyanato-benzothiazol-2-yl) carbamate can be prepared in the following way:

2.1 g of di-tert-butyl dicarbonate are added to a mixture of 1 g of commercial 6-thiocyanatobenzothiazol-2-ylamine and 2 cm$^3$ of triethylamine in 20 cm$^3$ of dichloromethane at 0° C. under argon, and the mixture obtained is stirred for 1 hour at 0° C. 147 mg of N,N-dimethylpyridin-4-amine are then added and the resulting mixture is subsequently brought gradually to 20° C. over 2 hours, with stirring. The clear green solution is run into water and extracted with ethyl acetate. 1.765 g of a yellow powder are obtained, and purified by chromatography on Biotage Quad 12/25 (KP-SIL, 60 A; 32-63 μm), elution being carried out with a 95/5, 90/10, 85/15, 80/20, 70/30, 60/40 cyclohexane/ethyl acetate gradient. 1.058 g of 1,1-dimethylethyl (6-thiocyanatobenzothiazol-2-yl) carbamate are thus obtained in the form of a yellow powder, the characteristics of which are as follows:

MASS SPECTRUM: LC-MS-DAD-ELSD: 308(+)=(M+H)(+).

EXAMPLE 3

6-{[6-(4-Fluorophenyl)[1,2,4]triazolo[4,3-b]pyridazin-3-yl]sulphanyl}-1,3-benzothiazol-2-amine The 6-{[6-(4-fluorophenyl)[1,2,4]triazolo[4,3-b]pyridazin-3-yl]sulphanyl}-1,3-benzothiazol-2-amine can be prepared in the following way:

4×0.1 cm$^3$ of trifluoroacetic acid (containing 10% of anisole) are added to a mixture of 127 mg of 1,1-dimethylethyl (6-{[6-(4-fluorophenyl)-[1,2,4]triazolo[4,3-b]pyridazin-3-yl]sulphanyl}-1,3-benzothiazol-2-yl)carbamate in 5 cm$^3$ of dichloromethane stirred at 20° C., this addition taking place over 7 h, until the starting product has disappeared. The reaction mixture is then concentrated under reduced pressure, so as to recover 186.5 mg of yellow powder which is purified by chromatography on Biotage Quad 12/25 (KP-SIL, 60 A; 32-63 μm), elution being carried out with a gradient of dichloromethane then dichloromethane/methanol: 99.5/0.5, 99/1, 98.5/1.5, 98/2, 97.5/2.5, 97/3. 36.6 mg of 6-{[6-(4-fluorophenyl)[1,2,4]triazolo[4,3-b]pyridazin-3-yl]sulphanyl}-1,3-benzothiazol-2-amine are thus obtained in the form of a whitish powder, the characteristics of which are as follows:

MELTING POINT>260° C. (Köfler block)

NMR SPECTRUM 66292V $^1$H NMR (400 MHz, d6-DMSO) δppm 7.31 (d, J=8.3 Hz, 1 H) 7.35-7.48 (m, 3 H) 7.66 (s, 2 H) 7.98 (d, J=2.0 Hz, 1 H) 8.01 (d, J=9.8 Hz, 1 H) 8.12 (dd, J=8.8, 5.4 Hz, 1 H) 8.49 (d, J=9.8 Hz, 1 H)

MASS SPECTRUM: LC-MS-DAD-ELSD: 393(−)=(M−H)(−); 395(+)=(M+H)(+).

EXAMPLE 4

Methyl (6-{[6-(4-fluorophenyl)[1,2,4]triazolo[4,3-b]
pyridazin-3-yl]sulphanyl}-1H-benzimidazol-2-yl)
carbamate a) The methyl (6-{[6-(4-fluorophenyl)[1,2,4]triazolo[4,3-b]
pyridazin-3-yl]sulphanyl}-1H-benzimidazol-2-yl)carbamate can be prepared in the following way:

0.02 cm$^3$ of glacial acetic acid and 65 mg of dimethyl[(Z)-(methylthio)-methylydene]biscarbamate are added to a mixture of 110 mg of 4-{[6-(4-fluorophenyl)[1,2,4]triazolo[4,3-b]pyridazin-3-yl]sulphanyl}benzene-1,2-diamine in 4 cm$^3$ of methanol. The resulting mixture is heated at approximately 80° C. for 2 h 30 and then left over a weekend at 20° C. with stirring. The reaction mixture is subsequently brought to basic pH with a 28% aqueous ammonia solution. The precipitate obtained is filtered off and then washed with water and ethyl acetate and dried under vacuum. 53 mg of a beige solid of methyl (6-{[6-(4-fluorophenyl)[1,2,4]triazolo[4,3-b]pyridazin-3-yl]sulphanyl}-1H-benzimidazol-2-yl)carbamate are thus obtained, the characteristics of which are as follows:

MASS SPECTRUM: LC-MS-DAD-ELSD: 434(−)=(M−H)(−); 436(+)=(M+H)(+).

NMR SPECTRUM: $^1$H NMR (400 MHz, d6-DMSO) δ ppm 3.74 (s, 3 H) 7.33 (dd, J=8.5, 2.0 Hz, 1 H) 7.35-7.48 (m, masked, 1 H) 7.42 (t, J=9.0 Hz, 2 H) 7.67 (broad s, 1 H) 8.01 (d, J=10.0 Hz, 1 H) 8.11 (dd, J=9.0, 5.5 Hz, 2 H) 8.49 (d, J=10.0 Hz, 1 H) 10.92-12.44 (broad m, 2 H)

b) The 4-{[6-(4-fluorophenyl)[1,2,4]triazolo[4,3-b]pyridazin-3-yl]sulphanyl}-benzene-1,2-diamine can be prepared in the following way:

0.6 cm$^3$ of acetic acid and 145 mg of iron(0) are added to a mixture of 146 mg of 5-{[6-(4-fluorophenyl)[1,2,4]triazolo[4,3-b]pyridazin-3-yl]sulphanyl}-2-nitroaniline in 7 cm$^3$ of methanol. The reaction mixture is then stirred at reflux for 5 h 15 and then overnight at 20° C. before the addition of 10 cm$^3$ of a 5N aqueous solution of sodium hydroxide and 10 cm$^3$ of demineralized water. The mixture obtained is extracted with 2×30 cm$^3$ of ethyl acetate. The combined organic phases are washed with 20 cm$^3$ of water and then dried over magnesium sulphate and concentrated to dryness. The beige solid obtained is taken up in diethyl ether, spin-filter-dried, and then dried under vacuum. 71 mg of 4-{[6-(4-fluorophenyl)[1,2,4]triazolo[4,3-b]pyridazin-3-yl]sulphanyl}benzene-1,2-diamine are thus obtained, the characteristics of which are as follows:

MASS SPECTRUM: LC-MS-DAD-ELSD: 353(+)=(M+H)(+).

c) The 5-{[6-(4-fluorophenyl)[1,2,4]triazolo[4,3-b]pyridazin-3-yl]sulphanyl}-2-nitroaniline can be prepared in the following way:

342 mg of sodium borohydride are added to a mixture of 1.76 g of commercial 3-amino-4-nitrophenyl thiocyanate in 15 cm$^3$ of N,N-dimethylformamide. The reaction is stirred at ambient temperature for 2 h and then 746 mg of 3-chloro-6-(4-fluorophenyl)-1,2,4-triazolo[4,3-b]pyridazine and 1.25 cm$^3$ of triethylamine are added. The resulting mixture is then heated to 95° C. and then stirred for 1 h at 20° C. After the addition of demineralized water, the mixture obtained is extracted with 3×100 cm$^3$ of ethyl acetate (a small amount of methanol is added due to solubility problems). The organic phases are combined and then dried over magnesium sulphate and concentrated to dryness, so as to give a brown solid which is chromatographed on a 25 g Merck cartridge of silica 15-40 μm (elution with ethyl acetate). 360 mg of 5-{[6-(4-fluorophenyl)[1,2,4]triazolo[4,3-b]pyridazin-3-yl]sulphanyl}-2-nitroaniline are thus obtained in the form of a green solid, the characteristics of which are as follows:

MASS SPECTRUM: LC-MS-DAD-ELSD: 383(+)=(M+H)(+).

EXAMPLE 5

Methyl (6-{[6-(4-fluorophenyl)-7,8-dihydro[1,2,4]
triazolo[4,3-b]pyridazin-3-yl]sulphanyl}-1H-benzimidazol-2-yl)carbamate a) The methyl (6-{[6-(4-fluorophenyl)-7,8-dihydro[1,2,4]triazolo[4,3-b]pyridazin-3-yl]sulphanyl}-1H-benzimidazol-2-yl)carbamate can be prepared in the following way:

130 mg of commercial dimethyl[(Z)-(methylthio)methylidene]biscarbamate are added to a solution of 223 mg of 4-{[6-(4-fluorophenyl)-7,8-dihydro[1,2,4]triazolo[4,3-b]pyridazin-3-yl]sulphanyl}benzene-1,2-diamine in 9 cm$^3$ of methanol and 0.038 cm$^3$ of glacial acetic acid. The resulting mixture is heated at 80° C. for 5.5 h. 0.038 cm$^3$ of glacial acetic acid and 130 mg of dimethyl[(Z)-(methylthio)methylidene]biscarbamate are again added and the mixture is heated at 80° C. for 8 h. After an overnight period at 20° C., an aqueous solution of ammonia at 28% is added to the mixture obtained so as to obtain a basic pH. The precipitate formed is filtered off and then washed successively with water and with ethyl acetate. The resulting solid is dried under vacuum and then chromatographed on a Merck cartridge (25 g of silica 15-40 μm), elution being carried out with ethyl acetate. 105 mg of methyl (6-{[6-(4-fluorophenyl)-7,8-dihydro[1,2,4]triazolo[4,3-b]pyridazin-3-yl]sulphanyl}-1H-benzimidazol-2-yl)carbamate are thus recovered in the form of a brown solid, the characteristics of which are as follows:

MASS SPECTRUM: LC-MS-DAD-ELSD: 438(+)=(M+H)(+).

NMR SPECTRUM: $^1$H NMR (400 MHz, d6-DMSO) δ ppm 3.16 (s, 4 H) 3.76 (s, 3 H) 7.29 (dd, J=8.3, 2.0 Hz, 0 H) 7.35 (t, J=8.8 Hz, 2 H) 7.41 (d, J=8.3 Hz, 1 H) 7.64 (s, 1 H) 7.95 (dd, J=8.8, 5.4 Hz, 2 H) 11.33 (br, s, 1H) 11.94 (br, s, 1 H)

b) The 4-{[6-(4-fluorophenyl)-7,8-dihydro[1,2,4]triazolo[4,3-b]pyridazin-3-yl]sulphanyl}benzene-1,2-diamine can be prepared in the following way:

422 mg of zinc(0) are added to a solution of 240 mg of 5-{[6-(4-fluorophenyl)[1,2,4]triazolo[4,3-b]pyridazin-3-yl]sulphanyl}-2-nitroaniline in 13 cm$^3$ of acetic acid and the resulting mixture is stirred for 1 h at 20° C. 30 cm$^3$ of water are then added to the reaction mixture, which is changed to an alkaline medium by adding 16 cm$^3$ of an aqueous solution of ammonia at 28%. The mixture obtained is extracted with ethyl acetate. The resulting organic phase is washed successively with a saturated aqueous solution of sodium hydrogen carbonate and with a saturated aqueous solution of sodium chloride and is then dried over magnesium sulphate, filtered and evaporated to dryness. The residue is made into a paste in ether, filtered, and then dried under vacuum at 20° C. 479 mg of 4-{[6-(4-fluorophenyl)-7,8-dihydro[1,2,4]triazolo[4,3-b]pyridazin-3-yl]sulphanyl}benzene-1,2-diamine are thus obtained, the characteristics of which are as follows:

MASS SPECTRUM: LC-MS-DAD-ELSD: 355(+)=(M+H)(+).

EXAMPLE 6

1-(6-{[6-(4-Fluorophenyl)[1,2,4]triazolo[4,3-b]pyridazin-3-yl]sulphanyl}-1H-benzimidazol-2-yl)-3-(2-morpholin-4-ylethyl)urea The 1-(6-{[6-(4-fluorophenyl)[1,2,4]triazolo[4,3-b]pyridazin-3-yl]sulphanyl}-1H-benzimidazol-2-yl)-3-(2-morpholin-4-ylethyl)urea can be prepared in the following way:

A microwave tube is loaded with 200 mg of methyl (6-{[6-(4-fluorophenyl)[1,2,4]triazolo[4,3-b]pyridazin-3-yl]sulphanyl}-1H-benzimidazol-2-yl)carbamate, 60 mg of N-(2-aminoethyl)-morpholine and 2 cm³ of 1-methyl-2-pyrrolidinone. The resulting mixture is heated at 120° C. for 25 min. The solvent is then concentrated under reduced pressure (~7 mbar/80° C.) so as to recover 292.6 mg of brown powder. This solid is mixed with another batch of 50.4 mg obtained in a similar manner in another experiment. The crude batch of 343 mg is then purified by chromatography on Biotage Quad 12/25 (KP-SIL, 60 A; 32-63 µM), elution being carried out with a gradient of dichloromethane and then dichloromethane/eluent B: 99/1, 98/2, 95/5, 90/10, 85/15, 82.5/17.5 (eluent B=38/17/2 dichloromethane/methanol/aqueous ammonia). 190 mg of 11-(6-{[6-(4-fluorophenyl)[1,2,4]triazolo[4,3-b]pyridazin-3-yl]sulphanyl}-1H-benzimidazol-2-yl)-3-(2-morpholin-4-ylethyl)urea are thus obtained in the form of a beige powder, the characteristics of which are as follows:

NMR SPECTRUM: ¹H NMR (400 MHz, d6-DMSO) δ ppm 2.35-2.45 (m, 6 H) 3.21-3.29 (m, 2 H) 3.50-3.58 (m, 4 H) 7.29 (d, J=6.8 Hz, 2 H) 7.35 (d, J=6.8 Hz, 1 H) 7.42 (t, J=8.8 Hz, 2 H) 7.61 (br, s, 1 H) 8.00 (d, J=9.8 Hz, 1 H) 8.12 (dd, J=8.8, 5.4 Hz, 2 H) 8.48 (d, J=9.8 Hz, 1 H) 10.05 (br, s, 1 H) 11.70 (br, s, 1H)

MASS SPECTRUM: LC-MS-DAD-ELSD: 532(−)=(M−H)(−); 534(+)=(M+H)(+).

EXAMPLE 7

6-{[6-(4-Fluorophenyl)[1,2,4]triazolo[4,3-b]pyridazin-3-yl]sulphanyl}-1H-benzimidazol-2-amine The 6-{[6-(4-fluorophenyl)[1,2,4]triazolo[4,3-b]pyridazin-3-yl]sulphanyl}-1H-benzimidazol-2-amine can be prepared in the following way:

A mixture of 4-{[6-(4-fluorophenyl)[1,2,4]triazolo[4,3-b]pyridazin-3-yl]sulphanyl}benzene-1,2-diamine and of 42 mg of cyanogen bromide in 10 cm³ of ethanol is brought to reflux for 3 hours. The resulting reaction mixture is then run into a 2.5N aqueous solution of sodium hydroxide and the mixture obtained is subsequently extracted with a 90/10 mixture of ethyl acetate and methanol. The organic phases are combined then dried over magnesium sulphate and then evaporated. A yellow powder is recovered, and is chromatographed on Biotage Quad 12/25 (KP-SIL, 60 A; 32-63 µM), elution being carried out with a gradient of dichloromethane and then dichloromethane/eluent B: 95/5, 92.5/7.5, 90/10, 87.5/12.5, 85/15 (eluent B=dichloromethane/methanol/aqueous ammonia 38/17/2). 43.2 mg of 6-{[6-(4-fluorophenyl)[1,2,4]triazolo[4,3-b]pyridazin-3-yl]sulphanyl}-1H-benzimidazol-2-amine are thus obtained in the form of a whitish powder, the characteristics of which are as follows:

NMR SPECTRUM: ¹H NMR (400 MHz, d6-DMSO) δ ppm 6.33 (br, s, 2 H) 7.07-7.12 (m, 1 H) 7.19 (br, s, 2 H) 7.38 (br, s, 1 H) 7.43 (t, J=8.8 Hz, 2 H) 7.99 (d, J=9.8 Hz, 1 H) 8.13 (dd, J=8.8, 5.4 Hz, 2 H) 8.46 (d, J=9.8 Hz, 1 H) 10.85 (br, s, 1 H)

MASS SPECTRUM: LC-MS-DAD-ELSD: 376(−)=(M−H)(−); 378(+)=(M+H)(+).

EXAMPLE 8

6-[(4-{3-[(2-amino-1,3-benzothiazol-6-yl)sulphanyl]-7,8-dihydro[1,2,4]triazolo-[4,3-b]pyridazin-6-yl}phenyl)sulphanyl]-1,3-benzothiazol-2-amine The 6-[(4-{3-[(2-amino-1,3-benzothiazol-6-yl)sulphanyl]-7,8-dihydro[1,2,4]-triazolo[4,3-b]pyridazin-6-yl}phenyl)sulphanyl]-1,3-benzothiazol-2-amine can be prepared in the following way:

92 mg of sodium borohydride are added to a solution of 500 mg of 2-amino-1,3-benzothiazol-6-yl thiocyanate in 6 cm³ of N,N-dimethylformamide. The mixture obtained is stirred at 20° C. for 2 h. 200 mg of 3-chloro-6-(4-fluorophenyl)-1,2,4-triazolo[4,3-b]pyridazine and 0.34 cm³ of triethylamine are then added to the rust-coloured suspension obtained. The resulting mixture is stirred at 90-110° C. for 1 h and then cooled to 20° C. The reaction mixture is taken up in a mixture of water and ethyl acetate. After separation, the organic phase is dried over magnesium sulphate and then concentrated to dryness under vacuum. The residue is chromatographed on a Biotage Si 12M+ column, elution being carried out with dichloromethane and then with a 95/5 mixture of dichloromethane/eluent B (eluent B=38/17/2 dichloromethane/methanol/aqueous ammonia). 41 mg of 6-[(4-{3-[(2-amino-1,3-benzothiazol-6-yl)sulphanyl]-7,8-dihydro[1,2,4]triazolo[4,3-b]pyridazin-6-yl}phenyl)sulphanyl]-1,3-benzothiazol-2-amine are thus obtained in the form of a yellow powder, the characteristics of which are as follows:

MELTING POINT: 182° C. (Köfler block)

NMR: ¹H NMR (400 MHz, d6-DMSO) δppm 3.12 (dd, J=6.6, 4.6 Hz, 4 H) 7.19 (d, J=8.5 Hz, 2 H) 7.30 (d, J=8.3 Hz, 1 H) 7.34-7.46 (m, 3 H) 7.62 (s, 2 H) 7.69 (s, 2 H) 7.80 (d, J=8.5 Hz, 2 H) 7.90 (d, J=2.0 Hz, 1 H) 7.92 (d, J=2.0 Hz, 1 H)

MASS SPECTRUM: LC-MS-DAD-ELSD: 559(+)=(M+H)(+).

EXAMPLE 9

1-(6-{[6-(4-Fluorophenyl)[1,2,4]triazolo[4,3-b]pyridazin-3-yl]sulphanyl}-1,3-benzothiazol-2-yl)-3-(2-morpholin-4-ylethyl)urea a) The 1-(6-{[6-(4-fluorophenyl)[1,2,4]triazolo[4,3-b]pyridazin-3-yl]sulphanyl}-1,3-benzothiazol-2-yl)-3-(2-morpholin-4-ylethyl)urea was prepared according to the method described in Example 1a, but using 240 mg of 3-chloro-6-(4-fluorophenyl)-1,2,4-triazolo[4,3-b]pyridazine, 338 mg of 1-(2-morpholin-4-ylethyl)-3-(6-sulphanyl-1,3-benzothiazol-2-yl)urea, 0.14 cm³ of triethylamine and 38 mg of sodium borohydride. The crude obtained is chromatographed on a Merck cartridge (30 g of silica 15-40 µm), elution being carried out with dichloromethane. 117 mg of 1-(6-{[6-(4-fluorophenyl)[1,2,4]triazolo[4,3-b]pyridazin-3-yl]sulphanyl}-1,3-benzothiazol-2-yl)-3-(2-morpholin-4-ylethyl)urea are thus recovered in the form of a beige solid, the characteristics of which are as follows:

NMR SPECTRUM ¹H NMR (400 MHz, d6-DMSO) δ ppm: 2.34-2.46 (m, 6 H) 3.23-3.29 (m, 2 H) 3.59 (t, J=3.9 Hz, 4 H) 6.77 (br, s, 1 H) 7.41 (t, J=8.8 Hz, 2 H) 7.52 (dd, J=8.3, 2.0 Hz, 1 H) 7.59 (d, J=8.3 Hz, 1 H) 8.03 (d, J=9.8 Hz, 1 H) 8.11 (dd, J=8.8, 5.4 Hz, 2 H) 8.17 (d, J=2.0 Hz, 1 H) 8.51 (d, J=9.8 Hz, 1 H) 10.90 (br, s, 1 H)

MASS SPECTRUM: LC-MS-DAD-ELSD: 549(−)=(M−H)(−); 551(+)=(M+H)(+).

b) The 1-(2-morpholin-4-ylethyl)-3-(6-sulphanyl-1,3-benzothiazol-2-yl)urea was prepared according to the method described in Example 1b, but using 900 mg of 2-{[(2-morpholin-4-ylethyl)carbamoyl]amino}-1,3-benzothiazol-6-yl thiocyanate, 11 mg of potassium dihydrogen phosphate and 1.1 g of DL-dithiothreitol. 633 mg of 1-(2-morpholin-4-ylethyl)-3-(6-sulphanyl-1,3-benzothiazol-2-yl)urea are thus obtained in the form of a white solid, the characteristics of which are as follows:

MASS SPECTRUM: LC-MS-DAD-ELSD: 337(−)=(M−H)(−); 339(+)=(M+H)(+).

c) The 2-{[(2-morpholin-4-ylethyl)carbamoyl]amino}-1,3-benzothiazol-6-yl thiocyanate can be prepared in the following way:

0.44 cm³ of 2-morpholin-4-ylethanamine is added, at 20° C., to a solution of 1 g of phenyl (6-thiocyanato-1,3-benzothiazol-2-yl)carbamate ester in 30 cm³ of tetrahydrofuran. After 24 h, the reaction mixture is evaporated to dryness and the residue obtained is chromatographed on a 70 g Merck cartridge (solid deposit; elution with a gradient of dichloromethane then 90/10 dichloromethane/methanol). 902 mg of 2-{[(2-morpholin-4-ylethyl)carbamoyl]-amino}-1,3-benzothiazol-6-yl thiocyanate are thus recovered in the form of a colourless foam, the characteristics of which are as follows:
MASS SPECTRUM: UPLC-MS-DAD-ELSD: 364(+)=(M+H)(+).

d) The phenyl (6-thiocyanato-1,3-benzothiazol-2-yl)carbamate was prepared in the following way:

7.5 g of phenyl chlorocarbonate and then 4.05 g of sodium hydrogen carbonate and 9.4 cm³ of water are added, at 20° C., to a solution of 2.5 g of commercial 2-amino-1,3-benzothiazol-6-yl thiocyanate in 94 cm³ of tetrahydrofuran. The resulting mixture is subsequently stirred at 20° C. for 20 h and then extracted with 2×150 cm³ of ethyl acetate. The organic phases are combined and then washed with 3×50 cm³ of a saturated aqueous solution of sodium hydrogen carbonate. The organic phase obtained is dried over magnesium sulphate and then concentrated to dryness under reduced pressure. The residue is taken up in 50 cm³ of water and the product is spin-filter-dried and dried under vacuum at 20° C. 3.45 g of phenyl (6-thiocyanato-1,3-benzothiazol-2-yl)carbamate are thus obtained in the form of a pale yellow solid, the characteristics of which are as follows:
MASS SPECTRUM: LC-MS-DAD-ELSD: 326(−)=(M−H)(−); 328(+)=(M+H)(+).

EXAMPLE 10

1-(2-Morpholin-4-ylethyl)-3-[6-([1,2,4]triazolo[4,3-b]pyridazin-3-ylsulphanyl)-1,3-benzothiazol-2-yl]urea a) The 1-(2-morpholin-4-ylethyl)-3-[6-([1,2,4]triazolo[4,3-b]pyridazin-3-ylsulphanyl)-1,3-benzothiazol-2-yl]urea can be prepared in the following way:

277 mg of n-tributyl phosphine are added to a solution of 462 mg of 1-(2-morpholin-4-ylethyl)-3-(6-sulphanyl-1,3-benzothiazol-2-yl)urea in 5.5 cm³ of tetrahydrofuran. This mixture is stirred for 1 h at 20° C. with nitrogen sparging, before the addition of 176 mg of 3-chloro-1,2,4-triazolo[4,3-b]pyridazine, 166 mg of potassium tert-butoxide, 12 mg of tetraphenyldiphosphoxane and 11 cm³ of toluene and stirring for 30 min at 20° C. with nitrogen sparging. 10 mg of tris(1,5-diphenylpenta-1,4-dien-3-one)dipalladium(0) are then added to the resulting mixture and the subsequent mixture is brought to reflux for 17 h. The solvent is concentrated under reduced pressure and the residue is then taken up in water and 0.1N hydrochloric acid HCl. The mixture obtained is then extracted with a 90/10 mixture of ethyl acetate/methanol. 632 mg of a yellow oil are obtained, and chromatographed on Biotage Quad 12/25 (KP-SIL, 60 A; 32-63 µM), elution being carried out with a gradient of dichloromethane then dichloromethane/methanol:99/1, 98/2, 97/3, 96/4, 95/6, 92/8, 90/10, 80/20. 75 mg of 1-(2-morpholin-4-ylethyl)-3-[6-([1,2,4]triazolo[4,3-b]pyridazin-3-ylsulphanyl)-1,3-benzothiazol-2-yl]urea are thus obtained in the form of a beige powder, the characteristics of which are as follows:
MELTING POINT: 252° C. (Köfler block)
NMR SPECTRUM ¹H NMR (400 MHz, d6-DMSO) δppm: 2.36-2.45 (m, 6 H) 3.24-3.36 (m, 2 H) 3.55-3.63 (m, 1 H) 6.78 (br. s., 0 H) 7.38-7.48 (m, 0 H) 7.57 (d, J=8.5 Hz, 0 H) 8.04 (d, J=1.5 Hz, 0 H) 8.43 (dd, J=9.5, 1.5 Hz, 0 H) 8.70 (dd, J=4.5, 1.5 Hz, 0 H) 10.85-10.95 (m, 0 H)
MASS SPECTRUM: UPLC-MS-DAD-ELSD: 457(+)=(M+H)(+).

b) The 3-chloro-1,2,4-triazolo[4,3-b]pyridazine can be prepared in the following way:

A mixture of 436 mg of [1,2,4]triazolo[4,3-b]pyridazin-3-ol in 6 cm³ of phosphoric trichloride is stirred at reflux for 3 h 30. The reaction mixture is run into a 4N aqueous solution of sodium hydroxide and the mixture obtained is extracted with a 90/10 mixture of ethyl acetate/methanol. The aqueous phase, which is still acidic (pH 1), is brought to pH 11 by adding concentrated sodium hydroxide, and then extracted again with a 90/10 mixture of ethyl acetate/methanol. The organic phases are combined and then dried over magnesium sulphate, filtered, then evaporated under vacuum. 808 mg of a whitish gum are thus obtained. 640 mg of this gum are taken up in ethyl acetate and the resulting solution is washed with water. The organic phase is dried over magnesium sulphate, filtered and then evaporated under vacuum, to give 281 mg of 3-chloro-1,2,4-triazolo[4,3-b]pyridazine, in the form of a white powder, the characteristics of which are as follows:
MASS SPECTRUM: UPLC-MS-DAD-ELSD: 155(+)/=(M+H)(+)/(1Cl present).

c) The [1,2,4]triazolo[4,3-b]pyridazin-3-ol can be prepared in the following way:

A mixture of 1.71 g of commercial 6-chloro[1,2,4]triazolo[4,3-b]pyridazin-3-ol, 1.90 g of ammonium formate and of 2.13 g of Pd/C at 5% in 50 cm³ of methanol is stirred at reflux for 3 h. The reaction mixture is then filtered in order to remove the catalyst and the filtrate obtained is concentrated under reduced pressure, to give 2.74 g of a greenish powder which is chromatographed on Biotage Quad 12/25 (KP-SIL, 60 A; 32-63 mM), elution being carried out with a gradient of dichloromethane/eluent B: 95/5, 90/10, 85/15, 80/20 (eluent B=38/17/2 dichloromethane/methanol/aqueous ammonia). 440 mg of [1,2,4]triazolo[4,3-b]pyridazin-3-ol are thus obtained in the form of a whitish powder, the characteristics of which are as follows:
MASS SPECTRUM: LC-MS-DAD-ELSD: 135(−)=(M−H)(−); 137(+)=(M+H)(+).

EXAMPLE 11

1-{2-[(2R,6S)-2,6-dimethylmorpholin-4-yl]ethyl}-3-(6-{[6-(4-fluorophenyl)-[1,2,4]triazolo[4,3-b]pyridazin-3-yl]sulphanyl}-1,3-benzothiazol-2-yl)urea a) The 1-{2-[(2R,6S)-2,6-dimethylmorpholin-4-yl]ethyl}-3-(6-{[6-(4-fluorophenyl)[1,2,4]triazolo[4,3-b]pyridazin-3-yl]sulphanyl}-1,3-benzothiazol-2-yl)urea was prepared according to the method described in Example 1a, but using 186 mg of 3-chloro-6-(4-fluorophenyl)-1,2,4-triazolo[4,3-b]pyridazine, 366 mg of 1-{2-[(2R,6S)-2,6-dimethylmorpholin-4-yl]ethyl}-3-(6-sulphanyl-1,3-benzothiazol-2-yl)urea, 0.14 cm³ of triethylamine and 38 mg of sodium borohydride. 73 mg of 1-{2-[(2R,6S)-2,6-dimethylmorpholin-4-yl]ethyl}-3-(6-{[6-(4-fluorophenyl)[1,2,4]triazolo[4,3-b]pyridazin-3-yl]sulphanyl}-1,3-benzothiazol-2-yl)urea are thus obtained in the form of a beige powder, the characteristics of which are as follows:
MELTING POINT: 150° C. (Köfler block)
NMR SPECTRUM 1H NMR (400 MHz, d6-DMSO) δ ppm: 1.04 (d, J=6.4 Hz, 6 H) 1.63 (t, J=10.5 Hz, 2 H) 2.39 (t, J=6.1 Hz, 2 H) 2.73-2.80 (m, 2 H) 3.24-3.29 (m, 2 H) 3.56 (br, s, 2 H) 6.76 (br, s, 1 H) 7.41 (t, J=9.0 Hz, 2 H) 7.51 (dd, J=8.5 2.0 Hz 1 H) 7.6 (d, J=8.5 Hz 1 H) 8.03 (d, J=9.8 Hz, 1 H) 8.11 (dd, J=8.8, 5.4 Hz, 2 H) 8.16 (d, J=1.5 Hz, 1 H) 8.51 (d, J=9.8 Hz, 1 H) 10.90 (br, s, 1 H)

MASS SPECTRUM: LC-MS-DAD-ELSD: 579(+)=(M+H)(+).

b) The 1-{2-[(2R,6S)-2,6-dimethylmorpholin-4-yl]ethyl}-3-(6-sulphanyl-1,3-benzothiazol-2-yl)urea was prepared according to the method described in Example 1b, but using 640 mg of 2-[({2-[(2R,6S)-2,6-dimethylmorpholin-4-yl]ethyl}carbamoyl)amino]-1,3-benzothiazol-6-yl thiocyanate, 7 mg of potassium dihydrogen phosphate and 729 mg of DL-dithiothreitol. 597 mg of 1-{2-[(2R,6S)-2,6-dimethylmorpholin-4-yl]ethyl}-3-(6-sulphanyl-1,3-benzothiazol-2-yl)urea are thus obtained in the form of a white solid, the characteristics of which are as follows:

MASS SPECTRUM: LC-MS-DAD-ELSD: 365(−)=(M−H)(−); 367(+)=(M+H)(+).

c) The 2-[({2-[(2R,6S)-2,6-dimethylmorpholin-4-yl]ethyl}carbamoyl)amino]-1,3-benzothiazol-6-yl thiocyanate was prepared according to the method described in Example 9c, but using 654 mg of phenyl (6-thiocyanato-1,3-benzothiazol-2-yl)carbamate and 0.35 cm$^3$ of 2-[(2R,6S)-2,6-dimethylmorpholin-4-yl]ethanamine. 783 mg of 2-[({2-[(2R,6S)-2,6-dimethylmorpholin-4-yl]ethyl}carbamoyl)amino]-1,3-benzothiazol-6-yl thiocyanate are thus obtained in the form of a white solid, the characteristics of which are as follows:

MASS SPECTRUM: LC-MS-DAD-ELSD: 392(+)=(M+H)(+).

EXAMPLE 12

2-Morpholin-4-ylethyl (6-{[6-(4-fluorophenyl)[1,2,4]triazolo[4,3-b]pyridazin-3-yl]sulphanyl}-1,3-benzothiazol-2-yl)carbamate a) The 2-morpholin-4-ylethyl (6-{[6-(4-fluorophenyl)[1,2,4]triazolo[4,3-b]pyridazin-3-yl]sulphanyl}-1,3-benzothiazol-2-yl)carbamate can be prepared according to the method described in Example 1a, but using 240 mg of 3-chloro-6-(4-fluorophenyl)-1,2,4-triazolo[4,3-b]pyridazine, 339 mg of 2-morpholin-4-ylethyl (6-sulphanyl-1,3-benzothiazol-2-yl)carbamate, 0.14 cm$^3$ of triethylamine and of 38 mg of sodium borohydride. The residue is chromatographed on an Analogix cartridge of 40 g of silica 15-40 µm, elution being carried out with a gradient of dichloromethane to 95/5 dichloromethane/methanol. 160 mg of 2-morpholin-4-ylethyl (6-{[6-(4-fluorophenyl)[1,2,4]triazolo[4,3-b]pyridazin-3-yl]sulphanyl}-1,3-benzothiazol-2-yl)carbamate are thus recovered in the form of a yellow solid, the characteristics of which are as follows:
MELTING POINT: 202° C. (Köfler block)
NMR SPECTRUM $^1$H NMR (400 MHz, d6-DMSO) δppm: 2.44 (t, J=4.5 Hz 4 H) 2.59 (t, J=5.5 Hz, 2 H) 3.55 (t, J=4.5 Hz 4 H) 4.29 (bt, J=5.5 Hz, 2 H) 7.40 (t, J=8.8 Hz, 2 H) 7.54 (bd, J=8.3 Hz, 1 H) 7.60-7.71 (m, 1 H) 8.03 (d, J=9.8 Hz, 1 H) 8.10 (dd, J=8.8, 5.4 Hz, 2 H) 8.20 (br, s, 1 H) 8.52 (d, J=9.8 Hz, 1 H) 12.18 (br, s, 1 H)

MASS SPECTRUM: LC-MS-DAD-ELSD: 550(−)=(M−H)(−); 552(+)=(M+H)(+).

b) The 2-morpholin-4-ylethyl (6-sulphanyl-1,3-benzothiazol-2-yl)carbamate was prepared according to the method described in Example 1b, but using 547 mg of 2-morpholin-4-ylethyl (6-thiocyanato-1,3-benzothiazol-2-yl)carbamate, 12 mg of potassium dihydrogen phosphate and 1.16 g of DL-dithiothreitol. 885 mg of 2-morpholin-4-ylethyl (6-sulphanyl-1,3-benzothiazol-2-yl)carbamate are thus obtained in the form of a white solid, the characteristics of which are as follows:

MASS SPECTRUM: LC-MS-DAD-ELSD: 338(−)=(M−H)(−); 340(+)=(M+H)(+).

c) The 2-morpholin-4-ylethyl (6-thiocyanato-1,3-benzothiazol-2-yl)carbamate was prepared according to the method described in Example 9c, but using 654 mg of phenyl (6-thiocyanato-1,3-benzothiazol-2-yl)carbamate and 0.27 cm$^3$ of 2-morpholin-4-ylethanamine. The residue obtained is chromatographed on an Analogix cartridge of 40 g of silica 15-40 µm, elution being carried out with a gradient of dichloromethane then 95/5 dichloromethane/methanol. 729 mg of 2-morpholin-4-ylethyl (6-thiocyanato-1,3-benzothiazol-2-yl)carbamate are thus obtained in the form of a white solid, the characteristics of which are as follows:

MASS SPECTRUM: LC-MS-DAD-ELSD: 365(+)=(M+H)(+).

EXAMPLE 13

1-(6-{[6-(4-Fluorophenyl)-7,8-dihydro[1,2,4]triazolo[4,3-b]pyridazin-3-yl]sulphanyl}-1,3-benzothiazol-2-yl)-3-[2-(4-methylpiperazin-1-yl)ethyl]urea a) The 1-(6-{[6-(4-fluorophenyl)-7,8-dihydro[1,2,4]triazolo[4,3-b]pyridazin-3-yl]sulphanyl}-1,3-benzothiazol-2-yl)-3-[2-(4-methylpiperazin-1-yl)ethyl]urea can be prepared according to the method described in Example 1a, but using 380 mg of 1-[2-(4-methylpiperazin-1-yl)ethyl]-3-(6-sulphanyl-1,3-benzothiazol-2-yl)urea, 185 mg of 3-chloro-6-(4-fluorophenyl)-1,2,4-triazolo[4,3-b]pyridazine, 0.125 cm$^3$ of triethylamine and 17 mg of sodium borohydride. The crude obtained is chromatographed on a Merck cartridge (25 g of silica 15-40 µm), elution being carried out with dichloromethane then a 38/17/3 mixture of dichloromethane/methanol/aqueous ammonia. 423 mg of 1-(6-{[6-(4-fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea are thus recovered (see Example 14) and 423 mg of 1-(6-{[6-(4-fluorophenyl)-7,8-dihydro[1,2,4]triazolo[4,3-b]pyridazin-3-yl]sulphanyl}-1,3-benzothiazol-2-yl)-3-[2-(4-methylpiperazin-1-yl)ethyl]urea are thus recovered, in the form of a beige powder, the characteristics of which are as follows:
MELTING POINT: 161° C. (Köfler block)
NMR SPECTRUM $^1$H NMR (400 MHz, d6-DMSO) δppm: 2.15 (s, 3 H) 2.22-2.48 (m, 10 H) 3.18 (s, 4 H) 3.22-3.28 (m, 4 H) 6.75 (br, s, 1 H) 7.34 (t, J=9.0 Hz, 2 H) 7.51 (dd, J=8.3, 2.0 Hz, 1 H) 7.61 (d, J=8.3 Hz, 1 H) 7.95 (dd, J=9.0, 5.6 Hz, 2 H) 8.13 (d, J=2.0 Hz, 1 H) 10.91 (br, s, 1 H)

MASS SPECTRUM: LC-MS-DAD-ELSD: 564(−)=(M−H)(−); 566(+)=(M+H)(+).

b) The 1-[2-(4-methylpiperazin-1-yl)ethyl]-3-(6-sulphanyl-1,3-benzothiazol-2-yl)urea was prepared according to the method described in Example 1b, but using 1 g of 1-(6-thiocyanato-1,3-benzothiazol-2-yl)-3-[2-(4-methylpiperazin-1-yl)ethyl]urea, 14 mg of potassium dihydrogen phosphate and 1.16 g of DL-dithiothreitol. 380 mg of 1-[2-(4-methylpiperazin-1-yl)ethyl]-3-(6-sulphanyl-1,3-benzothiazol-2-yl)urea are thus obtained in the form of a white solid, the characteristics of which are as follows:

MASS SPECTRUM: LC-MS-DAD-ELSD: 350(−)=(M−H)(−); 352(+)=(M+H)(+).

c) The 1-(6-thiocyanato-1,3-benzothiazol-2-yl)-3-[2-(4-methylpiperazin-1-yl)ethyl]urea was prepared according to the method described in Example 9c, but using 982 mg of phenyl (6-thiocyanato-1,3-benzothiazol-2-yl)carbamate and 473 mg of 2-(4-methylpiperazin-1-yl)ethylamine. The residue obtained is chromatographed on a Merck cartridge (25 g of silica 15-40 μm), elution being carried out with a 90/10 mixture of dichloromethane/methanol. 1.13 g of 1-(6-thiocyanato-1,3-benzothiazol-2-yl)-3-[2-(4-methylpiperazin-1-yl)ethyl]urea are thus recovered in the form of a white solid, the characteristics of which are as follows:
MASS SPECTRUM: LC-MS-DAD-ELSD: 375(−)=(M_H)(−); 377(+)=(M+H)(+).

EXAMPLE 14

1-(6-{[6-(4-Fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea The 1-(6-{[6-(4-fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea was obtained in Example 13 and has the following characteristics
MELTING POINT: 176° C. (Köfler block)
$^1$H NMR SPECTRUM NMR (400 MHz, d6-DMSO) δppm: 2.15 (s, 3 H) 2.23-2.46 (m, 10 H) 3.20-3.28 (m, 2 H) 6.74 (br, s, 1 H) 7.40 (t, J=9.0 Hz, 2 H) 7.52 (dd, J=8.7, 2 Hz 1 H) 7.59 (d, J=8.7 Hz 1 H) 8.02 (d, J=9.8 Hz, 1 H) 8.11 (dd, J=8.8, 5.4 Hz, 2 H) 8.16 (d, J=2.0 Hz, 1 H) 8.51 (d, J=9.8 Hz, 1 H) 10.91 (br, s, 1 H)
MASS SPECTRUM: LC-MS-DAD-ELSD: 562(−)=(M−H)(−); 564(+)=(M+H)(+)

EXAMPLE 15

N-(6-{[6-(4-Fluorophenyl)[1,2,4]triazolo[4,3-b]pyridazin-3-yl]sulphanyl}-1,3-benzothiazol-2-yl)-4-morpholin-4-ylbutanamide a) The N-(6-{[6-(4-fluorophenyl)[1,2,4]triazolo[4,3-b]pyridazin-3-yl]sulphanyl}-1,3-benzothiazol-2-yl)-4-morpholin-4-ylbutanamide can be prepared according to the method described in Example 1a, using 202 mg of 4-morpholin-4-yl-N-(6-sulphanyl-1,3-benzothiazol-2-yl)butanamide, 150 mg of 3-chloro-6-(4-fluorophenyl)-1,2,4-triazolo[4,3-b]pyridazine, 0.125 cm³ of triethylamine and 14 mg sodium borohydride. The crude obtained is chromatographed on a Merck cartridge (25 g of silica 15-40 μm), elution being carried out with dichloromethane then a 38/17/3 mixture of dichloromethane/methanol/aqueous ammonia. 71 mg of N-(6-{[6-(4-fluorophenyl)[1,2,4]triazolo[4,3-b]pyridazin-3-yl]sulphanyl}-1,3-benzothiazol-2-yl)-4-morpholin-4-ylbutanamide are thus recovered in the form of a beige powder, the characteristics of which are as follows:
MELTING POINT: 220° C. (Köfler block)
MASS SPECTRUM: LC-MS-DAD-ELSD: 548(−)=(M−H)(−); 550(+)=(M+H)(+).
$^1$H NMR SPECTRUM NMR (400 MHz, d6-DMSO) δ ppm: 1.78 (quin, J=7.1 Hz, 2 H) 2.23-2.36 (m, 6 H) 2.5 (2H) 3.47 (t, J=4.6 Hz, 3 H) 7.40 (t, J=8.8 Hz, 2 H) 7.57 (dd, J=8.5, 2.0 Hz, 1 H) 7.71 (d, J=8.5 Hz, 1 H) 8.03 (d, J=9.8 Hz, 1 H) 8.10 (dd, J=8.8, 5.4 Hz, 2 H) 8.24 (d, J=2 Hz, 1 H) 8.52 (d, J=9.8 Hz, 1 H) 12.41 (br, s, 1 H)
b) The 4-morpholin-4-yl-N-(6-sulphanyl-1,3-benzothiazol-2-yl)butanamide was prepared according to the method described in Example 1b, but using 906 mg of 4-morpholin-4-yl-N-(6-thiocyanato-1,3-benzothiazol-2-yl)butanamide, 14 mg of potassium dihydrogen phosphate and 1.12 g of DL-dithiothreitol. 71 mg of 4-morpholin-4-yl-N-(6-sulphanyl-1,3-benzothiazol-2-yl)butanamide are thus obtained in the form of a white solid, the characteristics of which are as follows:
MASS SPECTRUM: LC-MS-DAD-ELSD: 336(−)=(M−H)(−); 338(+)=(M+H)(+).
c) The 4-morpholin-4-yl-N-(6-thiocyanato-1,3-benzothiazol-2-yl)butanamide can be prepared in the following way:
4.86 g of 1-hydroxybenzotriazole and 1.72 g of N,N-dimethylpyridin-4-amine are added to a mixture of 3.77 g of 4-morpholin-4-ylbutanoic acid, 7.5 cm³ of triethylamine and 6.90 g of N-[3-(dimethylamino)propyl]-N'-ethylcarbodiimide hydrochloride in 72 cm³ of dichloromethane. After stirring for 5 min at 20° C., 3.73 g of commercial 2-amino-1,3-benzothiazol-6-yle thiocyanate are added to the mixture obtained and this reaction mixture is refluxed for 23 h before a return to 20° C. and concentration to dryness. The residue obtained is chromatographed on a 400 g Analogix cartridge, elution being carried out with dichloromethane then a 95/5 mixture of dichloromethane/methanol. A mixture is recovered and is purified again on a 90 g Merck cartridge under the same elution conditions. 1.76 g of 4-morpholin-4-yl-N-(6-thiocyanato-1,3-benzothiazol-2-yl)butanamide are thus recovered in the form of an amorphous yellow solid, the characteristics of which are as follows:
MASS SPECTRUM: LC-MS-DAD-ELSD: 363(+)=(M+H)(+).

EXAMPLE 16

1,1-Dimethylethyl (6-{[6-(morpholin-4-yl)[1,2,4]triazolo[4,3-b]pyridazin-3-yl]sulphanyl}-1,3-benzothiazol-2-yl)carbamate a) The 1,1-dimethylethyl (6-{[6-(morpholin-4-yl)[1,2,4]triazolo[4,3-b]pyridazin-3-yl]sulphanyl}-1,3-benzothiazol-2-yl)carbamate can be prepared in the following way:
68 mg of sodium borohydride are added to a mixture of 430 mg of 3-chloro-6-(morpholin-4-yl)[1,2,4]triazolo[4,3-b]pyridazine and 510 mg of 1,1-dimethylethyl (6-sulphanyl-1,3-benzothiazol-2-yl)carbamate in 9 cm³ of degassed ethanol and then the reaction is refluxed for 23 h. The suspension is left at 20° C. overnight and is then concentrated to dryness under vacuum. The product is chromatographed by solid deposit on a Merck cartridge of 70 g of silica 15-40 μm, elution being carried out with a gradient of 100% dichloromethane to 95/5 dichloromethane/methanol. 370 mg of 1,1-dimethylethyl (6-{[6-(morpholin-4-yl)[1,2,4]triazolo[4,3-b]pyridazin-3-yl]sulphanyl}-1,3-benzothiazol-2-yl)carbamate are thus obtained in the form of a white solid, characteristics of which are as follows:
MELTING POINT: 195° C. (Köfler block)
MASS SPECTRUM: LC/MS electrospray on WATERS UPLC-SQD: MH+=486+; MH−=484−
NMR SPECTRUM 1H (400 MHz, d6-DMSO) δ ppm: 1.51 (s, 9 H) 3.46 (m, 4 H) 3.65 (m, 4 H) 7.39 (d, J=10.3 Hz, 1H) 7.46 (dd, J=8.5, 2.0 Hz, 1 H) 7.62 (d, J=8.5 Hz, 1 H) 8.13 (d, J=10.3 Hz, 1 H) 8.15 (d, J=2.0 Hz, 1 H) 11.84 (broad s, 1 H)
b) The 3-chloro-6-(morpholin-4-yl)[1,2,4]triazolo[4,3-b]pyridazine can be prepared in the following way:
0.9 cm³ of morpholine and 1.4 cm³ of triethylamine are added to a solution of 1.89 g of commercial 3,6-dichloro[1,2,4]triazolo[4,3-b]pyridazine in 20 cm³ of N,N-dimethylformamide. The reaction is stirred at 20° C. for 19 h. 60 cm³ of water are added and the mixture is extracted with ethyl acetate. The organic phase is washed with water and with brine and then dried over magnesium sulphate and concentrated to dryness, to give a beige solid. The latter is chromatographed by solid deposit on a Merck cartridge of 70 g of silica 15-40 μm, elution being carried out with a gradient of 100% dichloromethane to 95/5 dichloromethane/methanol. 1.97 g of 3-chloro-6-(morpholin-4-yl)[1,2,4]triazolo[4,3-b]pyridazine are obtained in the form of a very pale yellow solid, the characteristics of which are as follows:
MASS SPECTRUM: UPLC-MS-DAD-ELSD: 240=MH+.

EXAMPLE 17

1-[2-(Diethylamino)ethyl]-3-(6-{[6-(4-fluorophenyl)[1,2,4]triazolo[4,3-b]pyridazin-3-yl]sulphanyl}-1,3-benzothiazol-2-yl)urea a) The 1-[2-(diethylamino)ethyl]-3-(6-{[6-(4-fluorophenyl)[1,2,4]triazolo-[4,3-b]pyridazin-3-yl]sulphanyl}-1,3-benzothiazol-2-yl)urea can be prepared in the following way:
A stream of argon is sparged, for 5 minutes, into a solution of 300 mg of 2-({[2-(diethylamino)ethyl]carbamoyl}amino)-1,3-benzothiazol-6-ylthiocyanate in 6 cm³ of ethanol. 6 mg of potassium dihydrogen phosphate in 0.6 cm³ of water, 396 mg of DL-dithiothreitol and 204 mg of 3-chloro-6-(4-fluorophenyl)-1,2,4-triazolo[4,3-b]pyridazine are then added. The reaction is refluxed for 19 h, and the solution is then evaporated to dryness under vacuum. The residue is purified on a 25 g Merck silica cartridge by solid deposit, elution being carried out with a gradient of 100% dichloromethane to 8/2 dichloromethane/(38 dichloromethane/17 methanol/2 aqueous ammonia). 225 mg of 1-[2-(diethylamino)ethyl]-3-(6-{[6-(4-fluorophenyl)[1,2,4]triazolo[4,3-b]pyridazin-3-yl]sulphanyl}-1,3-benzothiazol-2-yl)urea are thus obtained in the form of a yellow powder, the characteristics of which are as follows:
MELTING POINT: 176° C. (Köfler block)
MASS SPECTRUM: MASS SPECTRUM: LC/MS electrospray on WATERS UPLC–SQD: MH+=537+; MH–=535–.
¹H NMR SPECTRUM (400 MHz, d6-DMSO) δ ppm: 0.97 (t, J=7.3 Hz, 6 H) 2.50 (m partially masked, 6 H) 3.20 (q, J=6.0 Hz, 2 H) 6.73 (m large, 1 H) 7.40 (t, J=8.8 Hz, 2 H) 7.52 (dd, J=8.5, 2.4 Hz, 1 H) 7.59 (d, J=8.5 Hz, 1 H) 8.02 (d, J=9.8 Hz, 1 H) 8.11 (dd, J=8.8, 5.4 Hz, 2 H) 8.16 (d, J=2.4 Hz, 1 H) 8.51 (d, J=9.8 Hz, 1 H) 10.91 (broad m, 1 H)

b) The 2-({[2-(diethylamino)ethyl]carbamoyl}amino)-1,3-benzothiazol-6-yl thiocyanate can be prepared according to the method described in Example 9c, but using 982 mg of phenyl (6-thiocyanato-1,3-benzothiazol-2-yl)carbamate ester, 30 cm³ of THF and 0.465 cm³ of N,N-diethylethylene-diamine. After purification on a Merck 30 g silica cartridge, elution being carried out with a gradient of 100% dichloromethane to 8/2 dichloromethane/(38 dichloromethane/17 methanol/2 aqueous ammonia), 896 mg of 2-({[2-(diethylamino)ethyl]carbamoyl}amino)-1,3-benzothiazol-6-yl thiocyanate are obtained in the form of a white solid, the characteristics are as follows:
MASS SPECTRUM: UPLC-MS-DAD-ELSD: 348=MH–; 350=MH+.

c) The 3-chloro-6-(4-fluorophenyl)-1,2,4-triazolo[4,3-b]pyridazine can be prepared in the following way:
a mixture of 4.16 g of 4-fluorophenylboronic acid, 9.37 g of barium hydroxide octahydrate, 2.20 g of [1,1'-bis(diphenylphosphino)ferrocene]dichloro-palladium(II) in a complex with dichloromethane (1:1) and 5.1 g of commercial 3,6-dichloro[1,2,4]triazolo[4,3-b]pyridazine in 40 cm³ of N,N-dimethylformamide containing 10 cm³ of water is heated in a bath at 80° C. for 1.5 h. The beigey-brown suspension obtained is cooled to 20° C. and then poured into approximately 200 cm³ of water. The insoluble material is spin-filter-dried and washed successively with water and with ether, and then dried under vacuum at 20° C. The resulting beige solid is made into a paste in dichloromethane, spin-filter-dried, and dried under vacuum at 20° C. 1.24 g of 3-chloro-6-(4-fluorophenyl)-1,2,4-triazolo[4,3-b]pyridazine are thus obtained. 30 g of silica are added to the combined mother liquors and the mixture is evaporated to dryness under vacuum. This residue is deposited onto a bed of 10 g of silica in a sintered glass filter and elution is carried out with dichloromethane. An additional 1.60 g of 3-chloro-6-(4-fluorophenyl)-1,2,4-triazolo[4,3-b]pyridazine are thus recovered.

EXAMPLE 18

N-(6-{[6-(Morpholin-4-yl)[1,2,4]triazolo[4,3-b]pyridazin-3-yl]sulphanyl}-1,3-benzothiazol-2-yl)acetamide a) The N-(6-{[6-(morpholin-4-yl)[1,2,4]triazolo[4,3-b]pyridazin-3-yl]sulphanyl}-1,3-benzothiazol-2-yl)acetamide can be prepared according to the method described in Example 17a, but using 249 mg of 2-(acetylamino)-1,3-benzothiazol-6-ylthiocyanate, 8 cm³ of ethanol, 8 mg of potassium dihydrogen phosphate in 0.8 cm³ of water, 462 mg of DL-dithiothreitol and 240 mg of 3-chloro-6-(morpholin-4-yl)[1,2,4]triazolo[4,3-b]pyridazine prepared according to Example 16a. 109 mg of N-(6-{[6-(morpholin-4-yl)[1,2,4]triazolo[4,3-b]pyridazin-3-yl]sulphanyl}-1,3-benzothiazol-2-yl)acetamide are thus obtained in the form of a white powder, the characteristics of which are as follows:
MELTING POINT: 225° C. (Köfler block)
MASS SPECTRUM: LC/MS electrospray on WATERS UPLC-SQD: MH+=428+; MH–=426–.
¹H NMR SPECTRUM (400 MHz, d6-DMSO) δ ppm: 2.19 (s, 3 H) 3.46 (m, 4 H) 3.63 (m, 4 H) 7.39 (d, J=10.3 Hz, 1 H) 7.48 (dd, J=8.5, 2.0 Hz, 1 H) 7.67 (d, J=8.5 Hz, 1 H) 8.13 (d, J=10.3 Hz, 1 H) 8.18 (d, J=2.0 Hz, 1 H) 12.41 (broad m, 1 H)

b) The 2-(acetylamino)-1,3-benzothiazol-6-ylthiocyanate can be prepared in the following way:
5 cm³ of acetic anhydride are added dropwise to 7 cm³ of pyridine at 20° C. After 5 min, 1 g of 2-amino-6-thiocyanatobenzothiazole (commercial) is added. The yellow suspension is stirred for 4 h and then concentrated to dryness under vacuum. The residue is made into a paste in ethyl ether. The insoluble material is isolated by filtration, to give 1.1 g of 2-(acetylamino)-1,3-benzothiazol-6-ylthiocyanate in the form of a yellow solid, the characteristics of which are as follows:
MASS SPECTRUM: UPLC-MS-DAD-ELSD: 248=MH–; 250=MH+

EXAMPLE 19

1,1-Dimethylethyl (6-{[6-(4-methylpiperazin-1-yl)[1,2,4]triazolo[4,3-b]pyridazin-3-yl]sulphanyl}-1,3-benzothiazol-2-yl)carbamate hydrochloride a) The 1,1-dimethylethyl (6-{[6-(4-methylpiperazin-1-yl)[1,2,4]triazolo[4,3-b]pyridazin-3-yl]sulphanyl}-1,3-benzothiazol-2-yl)carbamate can be prepared according to the method described in Example 17a, but using 565 mg of 1,1-dimethylethyl (6-thiocyanato-1,3-benzothiazol-2-yl)

carbamate (prepared according to Example 2c), 16 cm³ of ethanol, 16 mg of potassium dihydrogen phosphate in 1.6 cm³ of water, 924 mg of DL-dithiothreitol and 505 mg of 3-chloro-6-(4-methylpiperazin-1-yl)[1,2,4]triazolo[4,3-b] pyridazine. 246 mg of 1,1-dimethylethyl (6-{[6-(4-methylpiperazin-1-yl)[1,2,4]triazolo[4,3-b]pyridazin-3-yl]sulphanyl}-1,3-benzothiazol-2-yl)carbamate hydrochloride are thus obtained in the form of a white solid, the characteristics of which are as follows:
MELTING POINT: 241° C. (Köfler block)
MASS SPECTRUM: LC/MS electrospray on WATERS UPLC-SQD: MH+=499+; MH−=497−
¹H NMR SPECTRUM (400 MHz, d6-DMSO) δ ppm: 1.51 (s, 9 H) 2.70 (broad s, 3 H) 2.80-4.40 (broad m partially masked, 8 H) 7.44 (d, J=9.8 Hz, 1 H) 7.49 (dd, J=8.5, 2.0 Hz, 1 H) 7.64 (d, J=8.5 Hz, 1 H) 8.15 (d, J=2.0 Hz, 1 H) 8.22 (d, J=9.8 Hz, 1 H) 10.50 (broad m, 1 H) 11.84 (broad s, 1 H)
b) The 3-chloro-6-(4-methylpiperazin-1-yl)[1,2,4]triazolo[4,3-b]pyridazine can be prepared according to the method described in Example 16b, but using 945 mg of commercial 3,6-dichloro[1,2,4]triazolo[4,3-b]pyridazine, 10 cm³ of DMF, 0.56 cm³ of 1-methylpiperazine and 0.695 cm³ of triethylamine. 555 mg of 3-chloro-6-(4-methylpiperazin-1-yl)[1,2,4]triazolo[4,3-b]pyridazine are thus obtained in the form of a beige solid, the characteristics of which are as follows:
MASS SPECTRUM: UPLC-MS-DAD-ELSD: 253=MH+

EXAMPLE 20

1-(6-{[6-(1H-Imidazol-1-yl)[1,2,4]triazolo[4,3-b]pyridazin-3-yl]sulphanyl}-1,3-benzothiazol-2-yl)-3-[2-(morpholin-4-yl)ethyl]urea a) The 1-(6-{[6-(1H-imidazol-1-yl)[1,2,4]triazolo[4,3-b]pyridazin-3-yl]sulphanyl}-1,3-benzothiazol-2-yl)-3-[2-(morpholin-4-yl)ethyl]urea can be prepared according to the method described in Example 10a, but using 384 mg of 1-(2-morpholin-4-yl)ethyl-3-(6-sulphanyl-1,3-benzothiazol-2-yl)urea, 6 cm³ of tetrahydrofuran, 230 mg of n-tributylphosphine, 250 mg of 3-chloro-6-(1H-imidazol-1-yl)[1,2,4]triazolo[4,3-b]pyridazine, 140 mg of potassium tert-butoxide, 12.5 mg of tetraphenyldiphosphoxane, 11 cm³ of toluene and 11 mg of tris(1,5-diphenylpenta-1,4-dien-3-one)dipalladium(0). 33 mg of 1-(6-{[6-(1H-imidazol-1-yl)[1,2,4]triazolo[4,3-b]pyridazin-3-yl]sulphanyl}-1,3-benzothiazol-2-yl)-3-[2-(morpholin-4-yl)ethyl]urea are thus obtained in the form of a white solid, the characteristics of which are as follows:
MELTING POINT: 160° C. (Köfler block)
MASS SPECTRUM: LC/MS electrospray on WATERS ZQ: MH+=523+; MH−=521−
¹H NMR SPECTRUM (400 MHz, d6-DMSO) δ ppm: 2.41 (m, 6 H) 3.27 (q, J=5.9 Hz, 2 H) 3.59 (m, 4 H) 6.78 (broad m, 1 H) 7.21 (t, J=1.5 Hz, 1 H) 7.54 (dd, d, J=8.5, 2.0 Hz, 1 H) 7.58 (d, J=8.5 Hz, 1 H) 7.91 (t, J=1.5 Hz, 1 H) 8.02 (d, J=10.3 Hz, 1 H) 8.19 (d, J=2.0 Hz, 1 H) 8.58 (t, J=1.5 Hz, 1 H) 8.67 (d, J=10.3 Hz, 1 H) 10.89 (broad m, 1 H)
b) The 3-chloro-6-(1H-imidazol-1-yl)[1,2,4]triazolo[4,3-b]pyridazine can be prepared according to the method described in Example 16b, but using 5 g of commercial 3,6-dichloro[1,2,4]triazolo[4,3-b]pyridazine, 50 cm³ of N,N-dimethylformamide, 1.9 g of imidazole and 3.8 cm³ of triethylamine. 3.21 g of 3-chloro-6-(1H-imidazol-1-yl)[1,2,4]triazolo[4,3-b]pyridazine are thus obtained in the form of a greyish-brown powder, the characteristics of which are as follows:
MASS SPECTRUM: UPLC-MS-DAD-ELSD: 221=MH+.

EXAMPLE 21

1,1-Dimethylethyl {6-[(6-methoxy[1,2,4]triazolo[4,3-b]pyridazin-3-yl)sulphanyl]-1,3-benzothiazol-2-yl}carbamate a) The 1,1-dimethylethyl {6-[(6-methoxy[1,2,4]triazolo[4,3-b]pyridazin-3-yl)sulphanyl]-1,3-benzothiazol-2-yl}carbamate can be prepared according to the method described in Example 17a, but using 167 mg of 1,1-dimethylethyl (6-thiocyanato-1,3-benzothiazol-2-yl)carbamate, 5 cm³ of ethanol, 2.5 mg of potassium dihydrogen phosphate in 0.25 cm³ of water, 83 mg of DL-dithiothreitol and 100 mg of 3-chloro-6-methoxy[1,2,4]triazolo[4,3-b]pyridazine. 24 mg of 1,1-dimethylethyl {6-[(6-methoxy[1,2,4]triazolo[4,3-b]pyridazin-3-yl)sulphanyl]-1,3-benzothiazol-2-yl}carbamate are thus obtained in the form of a white powder, the characteristics of which are as follows:
MELTING POINT: 226° C. (Köfler block)
MASS SPECTRUM: LC/MS electrospray on WATERS UPLC-SQD: MH+=431+; MH−=429−
¹H NMR SPECTRUM (400 MHz, d6-DMSO) δ ppm: 1.51 (s, 9 H) 3.89 (s, 3 H) 7.10 (d, J=9.8 Hz, 1 H) 7.52 (dd, J=8.3, 2.0 Hz, 1 H) 7.64 (d, J=8.3 Hz, 1 H) 8.19 (d, J=2.0 Hz, 1 H) 8.29 (d, J=9.8 Hz, 1 H) 11.85 (broad m, 1 H).
b) The 3-chloro-6-methoxy[1,2,4]triazolo[4,3-b]pyridazine can be prepared according to the method described in Example 16b but using 1 g of commercial 3,6-dichloro[1,2,4]triazolo[4,3-b]pyridazine, 10.6 cm³ of a 0.5M solution of sodium methoxide in methanol and 30 cm³ of dioxane, after stirring at reflux for 3 h. 871 mg of 3-chloro-6-methoxy[1,2,4]triazolo[4,3-b]pyridazine are thus obtained in the form of a white powder, the characteristics of which are as follows:
MASS SPECTRUM: UPLC-MS-DAD-ELSD: 185=MH+.

EXAMPLE 22

1,1-Dimethylethyl (6-{[6-(1H-imidazol-1-yl)[1,2,4]triazolo[4,3-b]pyridazin-3-yl]sulphanyl}-1,3-benzothiazol-2-yl)carbamate a) The 1,1-dimethylethyl (6-{[6-(1H-imidazol-1-yl)[1,2,4]triazolo[4,3-b]pyridazin-3-yl]sulphanyl}-1,3-benzothiazol-2-yl)carbamate can be prepared according to the method described in Example 17a, but using 300 mg of 1,1-dimethylethyl (6-thiocyanato-1,3-benzothiazol-2-yl)carbamate, 6 cm³ of degassed ethanol, 6 mg of potassium dihydrogen phosphate in 0.6 cm³ of water, 452 mg of DL-dithiothreitol and 215 mg of 3-chloro-6-(1H-imidazol-1-yl)[1,2,4]triazolo[4,3-b]pyridazine. 117 mg of 1,1-dimethylethyl (6-{[6-(1H-imidazol-1-yl)[1,2,4]triazolo[4,3-b]pyridazin-3-yl]sulphanyl}-1,3-benzothiazol-2-yl)carbamate are thus obtained in the form of a yellow powder, the characteristics of which are as follows:
MELTING POINT: 172° C. (Köfler block)
MASS SPECTRUM: LC/MS electrospray on WATERS ZQ: MH+=467+; MH−=465−
¹H NMR SPECTRUM (400 MHz, d6-DMSO) δ ppm: 1.50 (s, 9 H) 7.20 (broad s, 1 H) 7.57 (dd, J=8.3, 2.0 Hz, 1 H) 7.65 (d, J=8.3 Hz, 1 H) 7.90 (t, J=1.5 Hz, 1 H) 8.02 (d, J=9.8 Hz, 1

H) 8.23 (d, J=2.0 Hz, 1 H) 8.57 (broad s, 1 H) 8.67 (d, J=9.8 Hz, 1 H) 11.83 (broad m, 1 H).

EXAMPLE 23

1-{6-[(6-Methoxy[1,2,4]triazolo[4,3-b]pyridazin-3-yl)sulphanyl]-1,3-benzothiazol-2-yl}-3-[2-(morpholin-4-yl)ethyl]urea a) The 1-{6-[(6-methoxy[1,2,4]triazolo[4,3-b]pyridazin-3-yl)sulphanyl]-1,3-benzothiazol-2-yl}-3-[2-(morpholin-4-yl)ethyl]urea can be prepared according to the method described in Example 17a, but using 505 mg of 1-[2-(morpholin-4-yl)ethyl]-3-(6-sulphanyl-1,3-benzothiazol-2-yl) urea, 20 cm$^3$ of degassed ethanol, 6.25 mg of potassium dihydrogen phosphate in 0.25 cm$^3$ of water, 625 mg of DL-dithiothreitol and 251 mg of 3-chloro-6-methoxy-[1,2,4]triazolo[4,3-b]pyridazine. 297 mg of 1-{6-[(6-methoxy[1,2,4]triazolo[4,3-b]pyridazin-3-yl)sulphanyl]-1,3-benzothiazol-2-yl}-3-[2-(morpholin-4-yl)ethyl]urea are thus obtained in the form of a white powder, the characteristics of which are as follows:
MELTING POINT: 230° C. (Köfler block)
MASS SPECTRUM: LC/MS electrospray on WATERS ZQ: MH+=487+; MH−=485−
NMR SPECTRUM 1H (400 MHz, d6-DMSO) δ ppm: 2.41 (m, 6 H) 3.28 (q, J=5.9 Hz, 2 H) 3.59 (m, 4H) 3.90 (s, 3 H) 6.77 (broad m, 1 H) 7.09 (d, J=9.9 Hz, 1 H) 7.50 (dd, J=8.4, 1.9 Hz, 1 H) 7.58 (d, J=8.4 Hz, 1 H) 8.14 (d, J=1.9 Hz, 1 H) 8.28 (d, J=9.9 Hz, 1 H) 10.91 (broad m, 1 H).

EXAMPLE 24

1,1-Dimethylethyl[6-({6-[(2-methoxyethyl)amino][1,2,4]triazolo[4,3-b]pyridazin-3-yl}sulphanyl)-1,3-benzothiazol-2-yl]carbamate a) The 1,1-dimethylethyl[6-({6-[(2-methoxyethyl)amino][1,2,4]triazolo[4,3-b]pyridazin-3-yl}sulphanyl)-1,3-benzothiazol-2-yl]carbamate can be prepared according to the method described in Example 17a, but using 614 mg of 1,1-dimethylethyl (6-thiocyanato-1,3-benzothiazol-2-yl) carbamate, 16 cm$^3$ of ethanol, 16 mg of potassium dihydrogen phosphate in 1.6 cm$^3$ of water, 924 mg of DL-dithiothreitol and 455 mg of 3-chloro-N-(2-methoxyethyl)[1,2,4]triazolo[4,3-b]pyridazin-6-amine. 301 mg of 1,1-dimethylethyl[6-({6-[(2-methoxyethyl)amino][1,2,4]triazolo[4,3-b]pyridazin-3-yl}sulphanyl)-1,3-benzothiazol-2-yl]carbamate are thus obtained in the form of a white solid, the characteristics of which are as follows:
MELTING POINT: 179° C. (Köfler block)
MASS SPECTRUM: LC/MS electrospray on WATERS UPLC-SQD: MH+=474+; MH−=472−
$^1$H NMR SPECTRUM (400 MHz, d6-DMSO) δ ppm: 1.50 (s, 9 H) 3.17 (s, 3 H) 3.27-3.37 (m partially masked, 4 H) 6.87 (d, J=9.8 Hz, 1 H) 7.41 (dd, J=8.4, 2.2 Hz, 1 H) 7.53 (broad t, J=5.1 Hz, 1 H) 7.61 (d, J=8.4 Hz, 1 H) 8.08 (d, J=2.2 Hz, 1 H) 11.80 (broad m, 1 H).
b) The 3-chloro-N-(2-methoxyethyl)[1,2,4]triazolo[4,3-b]pyridazin-6-amine can be prepared according to the method described in Example 16b but using 945 mg of 3,6-dichloro[1,2,4]triazolo[4,3-b]pyridazine, 10 cm$^3$ of N,N-dimethylformamide, 0.436 cm$^3$ of 2-methoxyethylamine and 0.695 cm$^3$ of triethylamine. 1.17 g of 3-chloro-N-(2-methoxyethyl)[1,2,4]triazolo[4,3-b]-pyridazin-6-amine are thus obtained in the form of a white solid, the characteristics of which are as follows:
MASS SPECTRUM: UPLC-MS-DAD-ELSD: 226=MH−; 228=MH+.

EXAMPLE 25

N-(6-{[6-(4-Methylpiperazin-1-yl)[1,2,4]triazolo[4,3-b]pyridazin-3-yl]sulphanyl}-1,3-benzothiazol-2-yl)acetamide a) The N-(6-{[6-(4-methylpiperazin-1-yl)[1,2,4]triazolo[4,3-b]pyridazin-3-yl]sulphanyl}-1,3-benzothiazol-2-yl)acetamide can be prepared according to the method described in Example 17a, but using 498 mg of 2-(acetylamino)-1,3-benzothiazol-6-yl thiocyanate, 16 cm$^3$ of ethanol, 16 mg of potassium dihydrogen phosphate in 1.6 cm$^3$ of water, 924 mg of DL-dithiothreitol and 505 mg of 3-chloro-6-(4-methylpiperazin-1-yl)[1,2,4]triazolo[4,3-b]pyridazine. 132 mg of N-(6-{[6-(4-methylpiperazin-1-yl)[1,2,4]triazolo[4,3-b]pyridazin-3-yl]sulphanyl}-1,3-benzothiazol-2-yl) acetamide are thus obtained in the form of a white solid, the characteristics of which are as follows:
MELTING POINT: 225° C. (Köfler block)
MASS SPECTRUM: LC/MS electrospray on WATERS UPLC-SQD: MH+=441+; MH−=439−
$^1$H NMR SPECTRUM (400 MHz, d6-DMSO) δ ppm: 2.15 (s, 3 H) 2.19 (s, 3 H) 2.30 (m, 4 H) 3.46 (m, 4 H) 7.40 (d, J=10.3 Hz, 1 H) 7.47 (dd, J=8.3, 2.0 Hz, 1 H) 7.67 (d, J=8.3 Hz, 1 H) 8.10 (d, J=10.3 Hz, 1 H) 8.16 (d, J=2.0 Hz, 1 H) 12.40 (broad m, 1 H).

EXAMPLE 26

6-{[6-(4-Fluorophenyl)[1,2,4]triazolo[4,3-b]pyridazin-3-yl]sulphanyl}-N-(2-methoxyethyl)-1,3-benzothiazol-2-amine a) The 6-{[6-(4-fluorophenyl)[1,2,4]triazolo[4,3-b]pyridazin-3-yl]sulphanyl}-N-(2-methoxyethyl)-1,3-benzothiazol-2-amine can be prepared in the following way:
45 mg of sodium hydride at 60% in oil are added to a mixture of 263 mg of 1,1-dimethylethyl (6-{[6-(4-fluorophenyl)[1,2,4]triazolo[4,3-b]pyridazin-3-yl]sulphanyl}-1,3-benzothiazol-2-yl)carbamate and 0.10 cm$^3$ of 2-chloroethyl methyl ether in 3 cm$^3$ of N,N-dimethylformamide at 20° C. The suspension is heated in a bath at 90° C. overnight. The cooled reaction mixture is coevaporated to dryness several times with toluene. The residue obtained is taken up in methanol. After paste formation for 15 min, the brownish-yellow suspension is spin-filter-dried. The insoluble material is washed several times with methanol. This solid is treated with 0.4 cm$^3$ of trifluoroacetic acid in 3 cm$^3$ of dichloromethane at 20° C. for 2 h. The resulting reaction mixture is concentrated to dryness under vacuum, to give 116 mg of 6-{[6-(4-fluorophenyl)[1,2,4]triazolo[4,3-b]pyridazin-3-yl]sulphanyl}-N-(2-methoxyethyl)-1,3-benzothiazol-2-amine in the form of a yellowy-beige powder, the characteristics of which are as follows:
MELTING POINT: 212° C. (Köfler block)
MASS SPECTRUM: LC/MS electrospray on WATERS UPLC-SQD: MH+=453+; MH−=451−
$^1$H NMR SPECTRUM (400 MHz, d6-DMSO) δ ppm: For this batch, all the signals are broad with: 3.27 (s, 3 H) 3.51 (m, 4 H) 7.27-7.48 (m, 4 H) 7.95-8.03 (m, 2 H) 8.11 (m, 2 H) 8.28 (m, 1 H) 8.48 (d, J=9.8 Hz, 1 H).

EXAMPLE 27

N-[6-({6-[(2-Methoxyethyl)amino][1,2,4]triazolo[4,3-b]pyridazin-3-yl}sulphanyl)-1,3-benzothiazol-2-yl]acetamide a) The N-[6-({6-[(2-methoxyethyl)amino][1,2,4]triazolo[4,3-b]pyridazin-3-yl}sulphanyl)-1,3-benzothiazol-2-yl]acetamide can be prepared according to the method described in Example 17a, but using 374 mg of 2-(acetylamino)-1,3-benzothiazol-6-yl thiocyanate, 12 cm³ of degassed ethanol, 12 mg of potassium dihydrogen phosphate in 1.2 cm³ of water, 694 mg of DL-dithiothreitol and 341 mg of 3-chloro-N-(2-methoxyethyl)[1,2,4]triazolo[4,3-b]pyridazin-6-amine. 104 mg of N-[6-({6-[(2-methoxyethyl)amino]-[1,2,4]triazolo[4,3-b]pyridazin-3-yl}sulphanyl)-1,3-benzothiazol-2-yl]acetamide are thus obtained in the form of a beige powder, the characteristics of which are as follows:

MELTING POINT>260° C. (Köfler block)
MASS SPECTRUM: LC/MS electrospray on WATERS UPLC-SQD: MH+=416+; MH−=414−
¹H NMR SPECTRUM (400 MHz, d6-DMSO) δ ppm: 2.19 (s, 3 H) 3.15 (s, 3 H) 3.25-3.35 (m partially masked, 4 H) 6.87 (d, J=9.8 Hz, 1 H) 7.43 (dd, J=8.5, 2.0 Hz, 1 H) 7.54 (broad t, J=5.6 Hz, 1 H) 7.66 (d, J=8.5 Hz, 1 H) 7.94 (d, J=9.8 Hz, 1 H) 8.10 (d, J=2.0 Hz, 1 H) 12.30 (broad m, 1 H)

EXAMPLE 28

1-[2-(Morpholin-4-yl)ethyl]-3-(6-{[6-(morpholin-4-yl)[1,2,4]triazolo[4,3-b]-pyridazin-3-yl]sulphanyl}-1,3-benzothiazol-2-yl)urea a) The 1-[2-(morpholin-4-yl)ethyl]-3-(6-{[6-(morpholin-4-yl)[1,2,4]triazolo-[4,3-b]pyridazin-3-yl]sulphanyl}-1,3-benzothiazol-2-yl)urea can be prepared according to method described in Example 16a, but using 240 mg of 3-chloro-6-(morpholin-4-yl)[1,2,4]triazolo[4,3-b]pyridazine, 5 cm³ of degassed ethanol, 38 mg of sodium borohydride and 338 mg of 1-[2-(morpholin-4-yl)ethyl]-3-(6-sulphanyl-1,3-benzothiazol-2-yl)urea. 134 mg of 1-[2-(morpholin-4-yl)ethyl]-3-(6-{[6-(morpholin-4-yl)[1,2,4]triazolo[4,3-b]pyridazin-3-yl]sulphanyl}-1,3-benzothiazol-2-yl)urea are thus obtained in the form of a white solid, the characteristics of which are as follows:

MELTING POINT: 208° C. (Büchi B-545)
MASS SPECTRUM: LC/MS electrospray on WATERS UPLC-SQD: MH+=542+; MH−=540−
¹H NMR SPECTRUM (400 MHz, d6-DMSO) δ ppm: 2.42 (m, 6 H) 3.25-3.37 (m partially, 2H) 3.46 (m, 4 H) 3.59 (m, 4 H) 3.64 (m, 4 H) 6.78 (broad m, 1 H) 7.38 (d, J=10.0 Hz, 1 H) 7.43 (dd, J=8.3, 2.0 Hz, 1 H) 7.55 (d, J=8.3 Hz, 1 H) 8.09-8.14 (m, 2 H) 10.89 (broad m, 1 H)

EXAMPLE 29

1-{6-[(6-Amino[1,2,4]triazolo[4,3-b]pyridazin-3-yl)sulphanyl]-1,3-benzothiazol-2-yl}-3-[2-(morpholin-4-yl)ethyl]urea a) The 1-{6-[(6-amino[1,2,4]triazolo[4,3-b]pyridazin-3-yl)sulphanyl]-1,3-benzothiazol-2-yl}-3-[2-(morpholin-4-yl)ethyl]urea can be prepared according to the method described in Example 17a, but using 399 mg of 1-[2-(morpholin-4-yl)ethyl]-3-(6-sulphanyl-1,3-benzothiazol-2-yl)urea, 20 cm³ of degassed ethanol, 6 mg of potassium dihydrogen phosphate in 0.25 cm³ of water, 546 mg of DL-dithiothreitol and 200 mg of 3-chloro[1,2,4]triazolo[4,3-b]pyridazin-6-amine. 129 mg of 1-{6-[(6-amino[1,2,4]triazolo[4,3-b]pyridazin-3-yl)sulphanyl]-1,3-benzothiazol-2-yl}-3-[2-(morpholin-4-yl)ethyl]urea are thus obtained in the form of a white powder, the characteristics of which are as follows:

MELTING POINT: 250° C. (Köfler block)
MASS SPECTRUM: LC/MS electrospray on WATERS ZQ: MH+=472+; MH−=470−
¹H NMR SPECTRUM (400 MHz, d6-DMSO) δ ppm: 2.41 (m, 6 H) 3.28 (q, J=6.1 Hz, 2 H) 3.59 (m, 4 H) 6.79 (broad m, 1 H) 6.83 (d, J=9.8 Hz, 1 H) 6.99 (broad s, 2 H) 7.31 (dd, J=8.3, 2.2 Hz, 1 H) 7.55 (d, J=8.3 Hz, 1 H) 7.95 (d, J=2.2 Hz, 1 H) 8.01 (d, J=9.8 Hz, 1 H) 10.88 (broad m, 1 H)

b) The 3-chloro[1,2,4]triazolo[4,3-b]pyridazin-6-amine can be prepared in the following way:

A mixture of 190 mg of commercial 3,6-dichloro[1,2,4]triazolo[4,3-b]pyridazine and 1 cm³ of aqueous ammonia at 35% in 1 cm³ of dioxane, in a sealed tube, is heated at between 70° C. and 90° C. for 3 h. The precipitate formed is filtered off, to give 156.4 mg of 3-chloro[1,2,4]triazolo[4,3-b]pyridazin-6-amine in the form of a beige powder, the characteristics of which are as follows:

MASS SPECTRUM: UPLC-MS-DAD-ELSD: 168=MH−; 170=MH+.

EXAMPLE 30

6-{[6-(4-Fluorophenyl)[1,2,4]triazolo[4,3-b]pyridazin-3-yl]sulphanyl}-N-[2-(morpholin-4-yl)ethyl]-1,3-benzothiazol-2-amine a) The 6-{[6-(4-fluorophenyl)[1,2,4]triazolo[4,3-b]pyridazin-3-yl]sulphanyl}-N-[2-(morpholin-4-yl)ethyl]-1,3-benzothiazol-2-amine can be prepared in the following way:

8 mg of dihydrogen phosphate in 1 cm³ of water, 680 mg of DL-dithiothreitol and 336 mg of 3-chloro-6-(4-fluorophenyl)[1,2,4]triazolo[4,3-b]pyridazine are added, at 20° C., to a solution of 636 mg of 1,1-dimethylethyl[2-(morpholin-4-yl)ethyl](6-thiocyanato-1,3-benzothiazol-2-yl)carbamate in 10 cm³ of ethanol degassed with argon for 5 min. The suspension is stirred at reflux for 18 h. The reaction is placed in a refrigerator overnight and then the greyish-white solid is spin-filter-dried. This solid is washed with diethyl ether and then made into a paste in dichloromethane and spin-filter-dried. 222 mg of 6-{[6-(4-fluorophenyl)[1,2,4]triazolo[4,3-b]pyridazin-3-yl]sulphanyl}-N-[2-(morpholin-4-yl)ethyl]-1,3-benzothiazol-2-amine are thus obtained in the form of a greyish-white powder, the characteristics of which are as follows:

MELTING POINT: 280° C. (Köfler block)
MASS SPECTRUM: LC/MS electrospray on WATERS UPLC-SQD: MH+=508+; MH−=506−
¹H NMR SPECTRUM (400 MHz, d6-DMSO) δ ppm: For this batch, all the signals are broad with: 2.40 (m, 4 H) 2.50 (m masked, 2 H) 3.48 (m, 2 H) 3.55 (m, 4 H) 7.28-7.52 (m, 4 H) 7.96-8.03 (m, 2 H) 8.06-8.22 (m, 3 H) 8.49 (d, J=10.0 Hz, 1 H).

b) The 1,1-dimethylethyl[2-(morpholin-4-yl)ethyl](6-thiocyanato-1,3-benzothiazol-2-yl)carbamate can be prepared in the following way:

195 mg of sodium hydride at 60% in oil are added to a mixture of 500 mg of 1,1-dimethylethyl (6-thiocyanato-1,3-benzothiazol-2-yl)carbamate in 7 cm³ of N,N-dimethylformamide at 20° C. After 5 min, 606 mg of 4-(2-chloroethyl)morpholine hydrochloride are added. The reaction medium is stirred over a weekend then concentrated to dryness under vacuum. The residue is purified on a Biotage Si-25 M column by dry deposit, elution being carried out with a dichloromethane/solution B gradient of 95/5 to 90/10 [solution B: dichloromethane/methanol/aqueous ammonia (38/17/2)]. 647 mg of 1,1-dimethylethyl[2-(morpholin-4-yl)ethyl](6-thiocyanato-1,3-benzothiazol-2-yl)carbamate are obtained, which compound is used as it is in the subsequent syntheses.

MASS SPECTRUM: UPLC-MS-DAD-ELSD: 421=MH+; 321=(MH+)-TBoc+H.

EXAMPLE 31

N-(3-{[2-({[2-(Morpholin-4-yl)ethyl]carbamoyl}amino)-1,3-benzothiazol-6-yl]sulphanyl}[1,2,4]triazolo[4,3-b]pyridazin-6-yl)acetamide a) The N-(3-{[2-({[2-(morpholin-4-yl)ethyl]carbamoyl}amino)-1,3-benzothiazol-6-yl]sulphanyl}[1,2,4]triazolo[4,3-b]pyridazin-6-yl)acetamide can be prepared according to the method described in Example 17a, but using 107 mg of 1-[2-(morpholin-4-yl)ethyl]-3-(6-sulphanyl-1,3-benzothiazol-2-yl)urea, 10 cm³ of ethanol, 2 mg of potassium dihydrogen phosphate in 0.2 cm³ of water, 148 mg of DL-dithiothreitol and 67 mg of N-(3-chloro[1,2,4]triazolo[4,3-b]pyridazin-6-yl)acetamide. 68 mg of N-(3-{[2-({[2-(morpholin-4-yl)ethyl]carbamoyl}amino)-1,3-benzothiazol-6-yl]sulphanyl}-[1,2,4]triazolo[4,3-b]pyridazin-6-yl)acetamide are thus obtained in the form of a white powder, the characteristics of which are as follows:

MELTING POINT: 190° C. (Köfler block)

MASS SPECTRUM: LC/MS electrospray on WATERS UPLC-SQD: MH+=514+; MH-=512-

¹H NMR SPECTRUM (400 MHz, d6-DMSO) δ ppm: 2.16 (s, 3 H) 2.40 (m, 6 H) 3.29 (m partially masked, 2 H) 3.59 (m, 4 H) 6.78 (broad m, 1 H) 7.40 (dd, J=8.5, 2.0 Hz, 1 H) 7.57 (d, J=8.5 Hz, 1 H) 8.01 (d, J=2.0 Hz, 1 H) 8.10 (d, J=10.1 Hz, 1 H) 8.38 (d, J=10.1 Hz, 1 H) 10.87 (broad m, 1 H) 11.17 (broad s, 1 H).

b) The N-(3-chloro[1,2,4]triazolo[4,3-b]pyridazin-6-yl)acetamide can be prepared in the following way:

0.11 cm³ of acetic anhyhdride is added to a mixture of 202 mg of 3-chloro[1,2,4]triazolo[4,3-b]pyridazin-6-amine in 5 cm³ of pyridine at 0° C. The temperature is allowed to rise to 20° C. over 6 h, then 0.05 cm³ of acetic anhydride is again added and stirring is maintained for 24 h. The precipitate formed is spin-filter-dried and then washed with ethyl ether and pentane. This solid is purified by chromatography on Biotage Quad 12/25 (KP-SIL, 60 A; 32-63 µM), elution being carried out with a gradient of dichloromethane/methanol of 100/0 to 90/10. 41 mg of N-(3-chloro[1,2,4]triazolo[4,3-b]pyridazin-6-yl)acetamide are thus obtained in the form of a white powder, the characteristics of which are as follows:

MASS SPECTRUM: LC-MS-DAD-ELSD: 210=MH-; 212=MH+

EXAMPLE 32

2,2-Dimethyl-N-(3-{[2-({[2-(morpholin-4-yl)ethyl]carbamoyl}amino)-1,3-benzothiazol-6-yl]sulphanyl}[1,2,4]triazolo[4,3-b]pyridazin-6-yl)propanamide a) The 2,2-dimethyl-N-(3-{[2-({[2-(morpholin-4-yl)ethyl]carbamoyl}amino)-1,3-benzothiazol-6-yl]sulphanyl}[1,2,4]triazolo[4,3-b]pyridazin-6-yl)propanamide can be prepared according to the method described in Example 17a but using 230 mg of 1-[2-(morpholin-4-yl)ethyl]-3-(6-sulphanyl-1,3-benzothiazol-2-yl)urea, 10 cm³ of ethanol, 4 mg of potassium dihydrogen phosphate in 0.2 cm³ of water, 315 mg of DL-dithiothreitol and 174 mg of N-(3-chloro[1,2,4]triazolo[4,3-b]pyridazin-6-yl)-2,2-dimethylpropanamide. 128 mg of 2,2-dimethyl-N-(3-{[2-({[2-(morpholin-4-yl)ethyl]carbamoyl}amino)-1,3-benzothiazol-6-yl]sulphanyl}[1,2,4]triazolo[4,3-b]pyridazin-6-yl)propanamide are thus obtained in the form of a white powder, the characteristics of which are as follows:

MELTING POINT: 195° C. (Köfler block)

MASS SPECTRUM: LC/MS electrospray on WATERS UPLC-SQD: MH+=556+; MH-=554-

¹H NMR SPECTRUM (400 MHz, d6-DMSO) δ ppm: 1.27 (s, 9 H) 2.42 (m, 6 H) 3.28 (m partially masked, 2 H) 3.60 (m, 4 H) 6.79 (broad m, 1 H) 7.45 (dd, J=8.5, 2.0 Hz, 1 H) 7.58 (d, J=8.5 Hz, 1 H) 7.90 (d, J=10.0 Hz, 1 H) 8.08 (d, J=2.0 Hz, 1 H) 8.35 (d, J=10.0 Hz, 1 H) 10.57 (broad s, 1 H) 10.80 (broad m, 1 H)

b) The N-(3-chloro[1,2,4]triazolo[4,3-b]pyridazin-6-yl)-2,2-dimethylpropan-amide can be prepared in the following way:

A mixture of 193 mg of 3-chloro[1,2,4]triazolo[4,3-b]pyridazin-6-amine and 0.14 cm³ of pivaloyl chloride in 5 cm³ of pyridine is stirred for 5 h at 20° C. 0.14 cm³ of pivaloyl chloride is again added and the mixture is left to stir overnight. The reaction medium obtained is concentrated to dryness under vacuum. The residue is washed with ethyl ether and pentane. The precipitate is taken up in a solution of ammonium chloride and then extracted with a 90/10 ethyl acetate/methanol mixture. The organic phase is evaporated to dryness. 157 mg of N-(3-chloro[1,2,4]triazolo[4,3-b]pyridazin-6-yl)-2,2-dimethylpropanamide are thus obtained in the form of a brown powder, the characteristics of which are as follows:

MASS SPECTRUM: UPLC-MS-DAD-ELSD: 252-=MH-; 254=MH+.

EXAMPLE 33

Phenyl (6-{[6-(4-fluorophenyl)[1,2,4]triazolo[4,3-b]pyridazin-3-yl]sulphanyl}-1,3-benzothiazol-2-yl)carbamate a) The phenyl (6-{[6-(4-fluorophenyl)[1,2,4]triazolo[4,3-b]pyridazin-3-yl]sulphanyl}-1,3-benzothiazol-2-yl)carbamate can be prepared according to the method described in Example 9d, but using 630 mg of 6-{[6-(4-fluorophenyl)[1,2,4]triazolo[4,3-b]pyridazin-3-yl]sulphanyl}-1,3-benzothiazol-2-amine and 0.9 cm³ of phenyl chloroformate in 6 cm³ of pyridine after 4 h of contact at 20° C. 823 mg of phenyl (6-{[6-(4-fluorophenyl)[1,2,4]triazolo[4,3-b]pyridazin-3-yl]sulphanyl}-1,3-benzothiazol-2-yl)carbamate are thus obtained in the form of a beige solid, the characteristics of which are as follows:

MELTING POINT>265° C. (Köfler block)

MASS SPECTRUM: LC/MS electrospray on WATERS UPLC-SQD: MH+=515+

¹H NMR SPECTRUM (400 MHz, d6-DMSO) δ ppm: 7.24-7.33 (m, 3 H) 7.36-7.48 (m, 4 H) 7.56 (dd, J=8.5, 2.0 Hz, 1 H) 7.70 (broad d, J=8.5 Hz, 1 H) 8.03 (d, J=9.8 Hz, 1 H) 8.10 (dd, J=9.0, 5.4 Hz, 2 H) 8.20 (broad s, 1 H) 8.52 (d, J=9.8 Hz, 1 H) 12.68 (broad m, 1 H).

b) The 6-{[6-(4-fluorophenyl)[1,2,4]triazolo[4,3-b]pyridazin-3-yl]sulphanyl}-1,3-benzothiazol-2-amine can also be prepared according to the method described in Example 17a, but using 829 mg of commercial 2-amino-6-thiocyanatobenzothiazole, 40 cm³ of ethanol, 20 mg of potassium dihydrogen phosphate in 1 cm³ of water, 1.85 g of DL-dithiothreitol and 995 mg of 3-chloro-6-(4-fluorophenyl)[1,2,4]triazolo[4,3-b]pyridazine. 1.58 g of 6-{[6-(4-fluorophenyl)[1,2,4]triazolo[4,3-b]pyridazin-3-yl]sulphanyl}-1,3-benzothiazol-2-amine are thus obtained in the form of a light brown solid, the characteristics of which are as follows:
MELTING POINT>265° C. (Köfler block).

EXAMPLE 34

1-[2-(Morpholin-4-yl)ethyl]-3-(6-{[6-(oxetan-2-ylmethoxy)[1,2,4]triazolo[4,3-b]pyridazin-3-yl]sulphanyl}-1,3-benzothiazol-2-yl)urea a) The 1-[2-(morpholin-4-yl)ethyl]-3-(6-{[6-(oxetan-2-ylmethoxy)[1,2,4]-triazolo[4,3-b]pyridazin-3-yl]sulphanyl}-1,3-benzothiazol-2-yl)urea can be prepared according to the method described in Example 16a, but using 240 mg of 3-chloro-6-(oxetan-2-ylmethoxy)[1,2,4]triazolo[4,3-b]pyridazine, 5 cm³ of degassed ethanol, 38 mg of sodium borohydride and 338 mg of 1-[2-(morpholin-4-yl)ethyl]-3-(6-sulphanyl-1,3-benzothiazol-2-yl)urea. 128 mg of 1-[2-(morpholin-4-yl)ethyl]-3-(6-{[6-(oxetan-2-ylmethoxy)[1,2,4]triazolo[4,3-b]-pyridazin-3-yl]sulphanyl}-1,3-benzothiazol-2-yl)urea are thus obtained in the form of a white solid, the characteristics of which are as follows:
MELTING POINT: 222° C. (Köfler block)
MASS SPECTRUM: LC/MS electrospray on WATERS UPLC-SQD: MH+=543+; MH−=541−
$^1$H NMR SPECTRUM (400 MHz, d6-DMSO) δ ppm: 2.40 (m, 6 H) 2.50 (m masked, 1 H) 2.65 (m, 1 H) 3.38 (m partially masked, 2 H) 3.59 (m, 4 H) 4.30 (dd, J=12.1, 3.0 Hz, 1 H) 4.37 (dd, J=12.1, 6.0 Hz, 1 H) 4.42-4.56 (m, 2 H) 4.98 (m, 1 H) 6.79 (broad t, J=5.6 Hz, 1 H) 7.14 (d, J=9.8 Hz, 1 H) 7.46 (dd, J=8.5, 2.1 Hz, 1 H) 7.57 (d, J=8.5 Hz, 1 H) 8.13 (d, J=2.1 Hz, 1 H) 8.30 (d, J=9.8 Hz, 1 H) 10.91 (broad m, 1 H)
b) The 3-chloro-6-(oxetan-2-ylmethoxy)[1,2,4]triazolo[4,3-b]pyridazine can be prepared in the following way:
a mixture of 756 mg of commercial 3,6-dichloro[1,2,4]triazolo[4,3-b]pyridazine, 0.352 cm³ of 2-hydroxymethyloxetane and 552 mg of potassium carbonate in 8 cm³ of N,N-dimethylformamide is heated at 100° C. for 6 h and then stirred at 20° C. overnight. The reaction medium is concentrated to dryness under vacuum. The residue obtained is purified by chromatography on a Merck cartridge of 25 g of silica 15-40 µm by solid deposit, elution being carried out with a dichloromethane/methanol gradient of 100/0 to 97/03. 701 mg of 3-chloro-6-(oxetan-2-ylmethoxy)[1,2,4]triazolo[4,3-b]pyridazine are thus obtained in the form of a beige solid, the characteristics of which are as follows:
MASS SPECTRUM: UPLC-MS-DAD-ELSD: 241=MH+.

EXAMPLE 35

Oxetan-2-ylmethyl (6-{[6-(4-fluorophenyl)[1,2,4]triazolo[4,3-b]pyridazin-3-yl]sulphanyl}-1,3-benzothiazol-2-yl)carbamate d) The oxetan-2-ylmethyl (6-{[6-(4-fluorophenyl)[1,2,4]triazolo[4,3-b]pyridazin-3-yl]sulphanyl}-1,3-benzothiazol-2-yl)carbamate can be prepared in the following way:
a mixture of 171 mg of phenyl (6-{[6-(4-fluorophenyl)[1,2,4]triazolo[4,3-b]pyridazin-3-yl]sulphanyl}-1,3-benzothiazol-2-yl)carbamate, 0.04 cm³ of 2-hydroxymethyloxetane and 0.06 cm³ of triethylamine in 3 cm³ of tetrahydrofuran is heated for 7.5 h in a bath at 80° C. The reaction is left to stand overnight at 20° C. and then the mixture is evaporated to dryness under vacuum. The residue is purified by chromatography on a Merck cartridge of 25 g of silica 15-40 µm by solid deposit, elution being carried out with a dichloromethane/methanol gradient of 100/0 to 96/04. 52 mg of oxetan-2-ylmethyl (6-{[6-(4-fluorophenyl)[1,2,4]triazolo[4,3-b]pyridazin-3-yl]sulphanyl}-1,3-benzothiazol-2-yl)carbamate are thus obtained in the form of a white solid, the characteristics of which are as follows:
MELTING POINT: 216.7° C. (Büchi B-545)
MASS SPECTRUM: LC/MS electrospray on WATERS UPLC-SQD: MH+=509+; MH−=507−
$^1$H NMR SPECTRUM (400 MHz, d6-DMSO) δ ppm: 2.36-2.72 (m partially masked, 2 H) 4.33 (m, 2 H) 4.41-4.59 (m, 2 H) 4.93 (m, 1 H) 7.40 (t, J=8.8 Hz, 2 H) 7.55 (dd, J=8.4, 2.1 Hz, 1 H) 7.67 (broad d, J=8.4 Hz, 1 H) 8.04 (d, J=9.8 Hz, 1 H) 8.10 (dd, J=9.0, 5.4 Hz, 2 H) 8.21 (broad s, 1 H) 8.51 (d, J=9.8 Hz, 1 H) 12.26 (broad m, 1 H).

EXAMPLE 36

N-{6-[(6-Methoxy[1,2,4]triazolo[4,3-b]pyridazin-3-yl)sulphanyl]-1,3-benzothiazol-2-yl}cyclopropanecarboxamide a) The N-{6-[(6-methoxy[1,2,4]triazolo[4,3-b]pyridazin-3-yl)sulphanyl]-1,3-benzothiazol-2-yl}cyclopropanecarboxamide can be prepared according to the method described in Example 17a, but using 537 mg of 2-[(cyclopropylcarbonyl)amino]-1,3-benzothiazol-6-ylthiocyanate, 20 cm³ of degassed ethanol, 8 mg of potassium dihydrogen phosphate in 0.20 cm³ of water, 754 mg of DL-dithiothreitol and 300 mg of 3-chloro-6-methoxy[1,2,4]triazolo[4,3-b]pyridazine. 86 mg of N-{6-[(6-methoxy[1,2,4]-triazolo[4,3-b]pyridazin-3-yl)sulphanyl]-1,3-benzothiazol-2-yl}cyclopropanecarboxamide are thus obtained in the form of a white powder, the characteristics of which are as follows:
MELTING POINT>260° C. (Köfler block)
MASS SPECTRUM: LC/MS electrospray on WATERS UPLC-SQD: MH+=399+; MH−=397−
$^1$H NMR SPECTRUM (400 MHz, d6-DMSO) δ ppm: 0.96 (m, 4 H) 1.99 (m, 1 H) 3.89 (s, 3 H) 7.09 (d, J=9.8 Hz, 1 H) 7.54 (broad d, J=8.3 Hz, 1 H) 7.69 (broad d, J=8.3 Hz, 1 H) 8.19 (broad s, 1 H) 8.29 (d, J=9.8 Hz, 1 H) 12.69 (broad m, 1 H)
b) The 2-[(cyclopropylcarbonyl)amino]-1,3-benzothiazol-6-yl thiocyanate was prepared in a manner similar to the method described in Example 18b, but using 2 g of commercial 2-amino-6-thiocyanatobenzothiazole and 1.21 g of cyclopropanecarboxylic acid chloride in 20 cm³ of pyridine after reaction for 5 h at 20° C. 2.65 g of 2-[(cyclopropylcarbonyl)amino]-1,3-benzothiazol-6-yl thiocycanate are thus obtained in the form of a yellow powder, the characteristics of which are as follows:
MASS SPECTRUM: UPLC-MS-DAD-ELSD: 274=MH−; 276=MH+

EXAMPLE 37

1-{6-[(6-Ethoxy[1,2,4]triazolo[4,3-b]pyridazin-3-yl)sulphanyl]-1,3-benzothiazol-2-yl}-3-[2-(morpholin-4-yl)ethyl]urea a) The 1-{6-[(6-ethoxy[1,2,4]triazolo[4,3-b]pyridazin-3-yl)sulphanyl]-1,3-benzothiazol-2-yl}-3-[2-(morpholin-4-yl)

ethyl]urea was prepared according to the method described in Example 17a, but using 613 mg of 1-[2-(morpholin-4-yl)ethyl]-3-(6-sulphanyl-1,3-benzothiazol-2-yl)urea, 20 cm$^3$ of degassed ethanol, 7 mg of potassium dihydrogen phosphate in 0.2 cm$^3$ of water, 699 mg of DL-dithiothreitol and 300 mg of 3-chloro-6-ethoxy[1,2,4]triazolo[4,3-b]pyridazine. 354 mg of 1-{6-[(6-ethoxy[1,2,4]triazolo[4,3-b]pyridazin-3-yl)sulphanyl]-1,3-benzothiazol-2-yl}-3-[2-(morpholin-4-yl)ethyl]urea are thus obtained in the form of a white powder, the characteristics of which are as follows:

MELTING POINT: 216° C. (Köfler block)

MASS SPECTRUM: LC/MS electrospray on WATERS UPLC-SQD: MH+=501+; MH−=499−

$^1$H NMR SPECTRUM (400 MHz, d6-DMSO) δ ppm: 1.29 (t, J=6.8 Hz, 3 H) 2.41 (m, 6 H) 3.28 (m partially masked, 2 H) 3.59 (m, 4 H) 4.29 (q, J=6.8 Hz, 2 H) 6.78 (broad m, 1 H) 7.06 (d, J=9.8 Hz, 1 H) 7.47 (dd, J=8.6, 2.1 Hz, 1 H) 7.57 (d, J=8.6 Hz, 1 H) 8.11 (d, J=2.1 Hz, 1 H) 8.27 (d, J=9.8 Hz, 1 H) 10.90 (broad m, 1 H).

b) The 3-chloro-6-ethoxy[1,2,4]triazolo[4,3-b]pyridazine was prepared according to the method described in Example 16b, but using 1 g of commercial 3,6-dichloro[1,2,4]triazolo[4,3-b]pyridazine, 1.71 g of a solution at 21% of sodium ethoxide in ethanol and 30 cm$^3$ of dioxane, after reaction at reflux for 5.5 h. 874 mg of 3-chloro-6-ethoxy[1,2,4]triazolo[4,3-b]pyridazine are thus obtained in the form of a whitish powder, the characteristics are as follows:

MASS SPECTRUM: UPLC-MS-DAD-ELSD: 199=MH+.

EXAMPLE 38

1-{6-[(6-Ethoxy-7,8-dihydro[1,2,4]triazolo[4,3-b]pyridazin-3-yl)sulphanyl]-1,3-benzothiazol-2-yl}-3-[2-(morpholin-4-yl)ethyl]urea a) The 1-{6-[(6-ethoxy-7,8-dihydro[1,2,4]triazolo[4,3-b]pyridazin-3-yl)sulphanyl]-1,3-benzothiazol-2-yl}-3-[2-(morpholin-4-yl)ethyl]urea can be prepared in the following way:

27 mg of sodium borohydride are added to a mixture of 179 mg of 1-{6-[(6-ethoxy[1,2,4]triazolo[4,3-b]pyridazin-3-yl)sulphanyl]-1,3-benzothiazol-2-yl}-3-[2-(morpholin-4-yl)ethyl]urea in 10 cm$^3$ of ethanol. The reaction is refluxed for 3.5 h, and then 108 mg of sodium borohydride are added gradually and the reflux is maintained for 48 h. The reaction mixture is concentrated to dryness under reduced pressure. The residue is purified by chromatography on Biotage Quad 12/25 (KP-SIL, 60 A; 32-63 mM), elution being carried out with a dichloromethane/methanol gradient of 99/1 to 93/7. 72 mg of 1-{6-[(6-ethoxy-7,8-dihydro[1,2,4]triazolo[4,3-b]pyridazin-3-yl)sulphanyl]-1,3-benzothiazol-2-yl}-3-[2-(morpholin-4-yl)ethyl]urea are thus obtained in the form of a white powder, the characteristics of which are as follows:

MELTING POINT: 230° C. (Köfler block)

MASS SPECTRUM: LC/MS electrospray on WATERS UPLC-SQD: MH+=503+; MH−=501−

$^1$H NMR SPECTRUM (400 MHz, d6-DMSO) δ ppm: 1.24 (d, J=7.1 Hz, 3 H) 2.41 (m, 6 H) 2.73 (t, J=8.1 Hz, 2 H) 3.10 (t, J=8.1 Hz, 2 H) 3.20-3.36 (m partially masked, 2 H) 3.58 (m, 4 H) 4.17 (q, J=7.1 Hz, 2 H) 6.99 (broad m, 1 H) 7.42 (dd, J=8.3, 2.0 Hz, 1 H) 7.54 (d, J=8.3 Hz, 1 H) 8.02 (d, J=2.0 Hz, 1 H) 11.14 (broad m, 1 H)

EXAMPLE 39

N-[6-({6-[(2-Methoxyethyl)amino][1,2,4]triazolo[4,3-b]pyridazin-3-yl}sulphanyl)-1,3-benzothiazol-2-yl]-4-(morpholin-4-yl)butanamide a) The N-[6-({6-[(2-methoxyethyl)amino][1,2,4]triazolo[4,3-b]pyridazin-3-yl}sulphanyl)-1,3-benzothiazol-2-yl]-4-(morpholin-4-yl)butanamide can be prepared according to the method described in Example 17a, but using 446 mg of 4-(morpholin-4-yl)-N-[6-thiocyanato-1,3-benzothiazol-2-yl]butanamide, 8 cm$^3$ of ethanol, 6 mg of potassium dihydrogen phosphate in 0.8 cm$^3$ of water, 570 mg of DL-dithiothreitol and 280 mg of 3-chloro-N-(2-methoxyethyl)[1,2,4]triazolo[4,3-b]pyridazin-6-amine. 160 mg of N-[6-({6-[(2-methoxyethyl)amino][1,2,4]triazolo[4,3-b]pyridazin-3-yl}sulphanyl)-1,3-benzothiazol-2-yl]-4-(morpholin-4-yl)butanamide are thus obtained in the form of a white powder, the characteristics of which are as follows:

MELTING POINT: 177° C. (Köfler block)

MASS SPECTRUM: LC/MS electrospray on WATERS UPLC-SQD: MH+=529+; MH−=527

$^1$H NMR SPECTRUM (400 MHz, d6-DMSO) δ ppm: 1.79 (broad m, 2 H) 2.22-2.58 (broad m partially masked, 8 H) 3.18 (s, 3 H) 3.23-3.58 (broad m partially masked, 8 H) 6.87 (d, J=10.0 Hz, 1 H) 7.43 (dd, J=8.5, 2.1 Hz, 1 H) 7.54 (broad t, J=5.6 Hz, 1 H) 7.67 (d, J=8.5 Hz, 1 H) 7.94 (d, J=10.0 Hz, 1 H) 8.11 (d, J=2.1 Hz, 1 H) 12.39 (broad m, 1 H).

EXAMPLE 40

N-[6-({6-[(2-Methoxyethyl)amino][1,2,4]triazolo[4,3-b]pyridazin-3-yl}sulphanyl)-1,3-benzothiazol-2-yl]cyclopropanecarboxamide a) The N-[6-({6-[(2-methoxyethyl)amino][1,2,4]triazolo[4,3-b]pyridazin-3-yl}sulphanyl)-1,3-benzothiazol-2-yl]cyclopropanecarboxamide can be prepared according to the method described in Example 17a, but using 605 mg of 2-[(cyclopropylcarbonyl)amino]-1,3-benzothiazol-6-ylthiocyanate, 13.5 cm$^3$ of degassed ethanol, 11 mg of potassium dihydrogen phosphate in 1.3 cm$^3$ of water, 1.02 g of DL-dithiothreitol and 500 mg of 3-chloro-N-(2-methoxyethyl)[1,2,4]triazolo[4,3-b]pyridazin-6-amine. 392 mg of N-[6-({6-[(2-methoxyethyl)amino][1,2,4]triazolo[4,3-b]pyridazin-3-yl}sulphanyl)-1,3-benzothiazol-2-yl]cyclopropanecarboxamide are thus obtained in the form of a white powder, the characteristics of which are as follows:

MELTING POINT: 212° C. (Köfler block)

MASS SPECTRUM: LC/MS electrospray on WATERS UPLC-SQD: MH+=442+; MH−=440

$^1$H NMR SPECTRUM (400 MHz, d6-DMSO) δ ppm: 0.95 (m, 4 H) 1.99 (m, 1 H) 3.15 (s, 3 H) 3.24-3.38 (m partially masked, 4 H) 6.86 (d, J=10.0 Hz, 1 H) 7.43 (dd, J=8.5, 2.0 Hz, 1 H) 7.53 (broad t, J=5.4 Hz, 1 H) 7.67 (d, J=8.5 Hz, 1 H) 7.94 (d, J=10.0 Hz, 1 H) 8.09 (d, J=2.0 Hz, 1 H) 12.67 (broad s, 1 H).

EXAMPLE 41

N-(6-{[6-(4-Fluorophenyl)[1,2,4]triazolo[4,3-b]pyridazin-3-yl]sulphanyl}-1,3-benzothiazol-2-yl)acetamide The N-(6-{[6-(4-fluorophenyl)[1,2,4]triazolo[4,3-b]pyridazin-3-yl]sulphanyl}-1,3-benzothiazol-2-yl)acetamide can be prepared according to the method described in Example 18b, but using 273 mg of 6-{[6-(4-fluorophenyl)[1,2,4]triazolo[4,3-b]pyridazin-3-yl]sulphanyl}-1,3-benzothiazol-2-amine in 2 cm³ of pyridine and 1 cm³ of acetic anhydride at 60° C. for 4 h. 207 mg of N-(6-{[6-(4-fluorophenyl)[1,2,4]triazolo[4,3-b]pyridazin-3-yl]sulphanyl}-1,3-benzothiazol-2-yl)acetamide are thus obtained in the form of a beige solid, the characteristics of which are as follows:

MELTING POINT>255° C. (Büchi B-545)

MASS SPECTRUM: LC/MS electrospray on WATERS UPLC-SQD:MH+=437+; MH−=435

¹H NMR SPECTRUM (400 MHz, d6-DMSO) δ ppm: 2.19 (s, 3 H) 7.40 (t, J=9.0 Hz, 2 H) 7.57 (dd, J=8.5, 2.1 Hz, 1 H) 7.72 (d, J=8.5 Hz, 1 H) 8.03 (d, J=9.8 Hz, 1 H) 8.06-8.15 (dd, J=9.0, 5.5 Hz, 2 H) 8.23 (d, J=2.1 Hz, 1 H) 8.52 (d, J=9.8 Hz, 1 H) 12.39 (broad s, 1 H).

EXAMPLE 42

1-(6-{[6-(4-Fluorophenyl)[1,2,4]triazolo[4,3-b]pyridazin-3-yl]sulphanyl}-1,3-benzothiazol-2-yl)-3-[2-(4-oxidomorpholin-4-yl)ethyl]urea a) The 1-(6-{[6-(4-fluorophenyl)[1,2,4]triazolo[4,3-b]pyridazin-3-yl]sulphanyl}-1,3-benzothiazol-2-yl)-3-[2-(4-oxidomorpholin-4-yl)ethyl]urea can be prepared in the following way:

116 mg of periodate of sodium in 0.5 cm³ of water are added to a mixture of 200 mg of 1-(6-{[6-(4-fluorophenyl)[1,2,4]triazolo[4,3-b]pyridazin-3-yl]sulphanyl}-1,3-benzothiazol-2-yl)-3-[2-(morpholin-4-yl)ethyl]urea in 5 cm³ of acetic acid at 20° C. After an overnight period, the precipitate is filtered off. The white powder obtained is a mixture containing oxidized product and starting product. This mixture is taken up in 10 cm³ of acetic acid with 155 mg of sodium periodate dissolved in 1 cm³ of water. The mixture is left to stir overnight at 20° C. The precipitate is then filtered off and then washed successively with diisopropyl ether and with diethyl ether. 155 mg of white powder of 1-(6-{[6-(4-fluorophenyl)[1,2,4]triazolo[4,3-b]pyridazin-3-yl]sulphanyl}-1,3-benzothiazol-2-yl)-3-[2-(4-oxidomorpholin-4-yl)ethyl]urea are obtained, the characteristics of which are as follows:

MELTING POINT: 190° C. (Köfler block)

MASS SPECTRUM: LC/MS electrospray on WATERS UPLC-SQD: MH+=567+; MH−=565−

¹H NMR SPECTRUM (400 MHz, d6-DMSO) δ ppm: 3.49-4.07 (m, 12 H) 7.41 (t, J=8.8 Hz, 2 H) 7.53 (d, J=8.5, 2.0 Hz, 1 H) 7.55 (m masked, 1 H) 7.61 (d, J=8.5 Hz, 1 H) 8.03 (d, J=9.8 Hz, 1 H) 8.12 (dd, J=8.8, 5.4 Hz, 2 H) 8.16 (d, J=2.0 Hz, 1 H) 8.51 (d, J=9.8 Hz, 1 H) 11.29 (broad m, 1 H).

EXAMPLE 43

6-{[6-(1-Methyl-1H-pyrazol-4-yl)[1,2,4]triazolo[4,3-b]pyridazin-3-yl]sulphanyl}-1,3-benzothiazol-2-amine a) The 6-{[6-(1-methyl-1H-pyrazol-4-yl)[1,2,4]triazolo[4,3-b]pyridazin-3-yl]sulphanyl}-1,3-benzothiazol-2-amine can be prepared in the following way:

280 mg of 1-(6-sulphanyl-benzothiazol-2-yl)-3-(2-morpholin-4-yl-ethyl)urea, 2 cm³ of dimethyl sulphoxide and 240 mg of potassium carbonate are introduced, at 20° C., in a microwave tube equipped with a magnetic stirrer. The suspension thus obtained is stirred for 5 minutes before the addition of 200 mg of 3-chloro-6-(1-methyl-1H-pyrazol-4-yl)-1,2,4-triazolo[4,3-b]pyridazine. The reaction mixture is then heated in a microwave oven for 10 minutes at 190° C., and then poured into 100 cm³ of water. The resulting mixture is stirred for 30 minutes under cold conditions. The solid is filtered off, washed with 3×100 cm³ of water and then spin-filter-dried. The brown powder thus obtained is purified by chromatography on silica gel (eluent: 95/5/0.5 dichloromethane/methanol/aqueous ammonia). A small amount of methanol and of hydrochloric acid in solution in dioxane is added to the fractions containing the expected product (to improve solubility). The fractions are combined and concentrated under reduced pressure. The oil thus obtained is taken up with 20 cm³ of a saturated aqueous solution of hydrogen carbonate (pH 8-9). The precipitate formed is filtered off and then washed with 3×20 cm³ of water and dried under vacuum. 120 mg of 6-{[6-(1-methyl-1H-pyrazol-4-yl)[1,2,4]triazolo[4,3-b]pyridazin-3-yl]sulphanyl}-1,3-benzothiazol-2-amine are thus obtained in the form of a light brown solid.

MELTING POINT>264° C. (Köfler block)

MASS SPECTRUM: LC/MS electrospray on WATERS ZQ: MH+=381+; MH−=379−

¹H NMR SPECTRUM (400 MHz, d6-DMSO) δ ppm: 3.94 (s, 3 H) 7.30 (d, J=8.3 Hz, 1 H) 7.44 (dd, J=8.3, 2.0 Hz, 1 H) 7.63 (broad s, 2 H) 7.73 (d, J=9.8 Hz, 1 H) 8.01 (d, J=2.0 Hz, 1 H) 8.11 (s, 1 H) 8.37 (d, J=9.8 Hz, 1 H) 8.49 (s, 1 H).

b) The 3-chloro-6-(1-methyl-1H-pyrazol-4-yl)-1,2,4-triazolo[4,3-b]pyridazine can be prepared in the following way:

0.61 g of 1-methyl-4-(4,4,5,5-tetramethyl-1,3,2-dioxaborolan-2-yl)-1H-pyrazole and 5.3 cm³ of a 1N aqueous solution of sodium hydroxide are added to a mixture of 0.5 g of commercial 3,6-dichloro-1,2,4-triazolo[4,3-b]pyridazine in 15 cm³ of 1,2-dimethoxyethane. The reaction mixture is stirred at a temperature in the region of 20° C. for 30 minutes before the addition of 92 mg of palladium dichlorobis(triphenylphosphine). The reaction mixture is then stirred at 65° C. for 30 minutes, and then brought back to a temperature in the region of 20° C. and poured into 20 cm³ of water. The mixture obtained is extracted with 3×100 cm³ of dichloromethane and the combined organic phases are washed with 2×100 cm³ of a saturated aqueous solution of sodium chloride. The resulting organic phase is dried over sodium sulphate, filtered and concentrated by evaporation under reduced pressure. The yellow powder thus obtained is purified by chromatography on silica gel (eluent: 98/2 CH₂Cl₂/MeOH). 0.2 g of 3-chloro-6-(1-methyl-1H-pyrazol-4-yl)-1,2,4-triazolo-[4,3-b]pyridazine is thus obtained in the form of a beige powder, the characteristics of which are as follows:

MASS SPECTRUM: LC/MS electrospray on WATERS ZQ: MH+=235+

¹H NMR SPECTRUM (400 MHz, d6-DMSO) δ ppm: 3.94 (s, 3 H) 7.79 (d, J=9.8 Hz, 1 H) 8.17 (s, 1 H) 8.40 (d, J=9.8 Hz, 1 H) 8.57 (s, 1 H)

EXAMPLE 44

1-(6-{[6-(4-Fluorophenyl)-7,8-dihydro-[1,2,4]triazolo[4,3-b]pyridazin-3-yl]sulphanyl}-1,3-benzothiazol-2-yl)-3-[2-(morpholin-4-yl)ethyl]urea a) The 1-(6-{[6-(4-fluorophenyl)-7,8-dihydro-[1,2,4]triazolo[4,3-b]pyridazin-3-yl]sulphanyl}-1,3-benzothiazol-2-yl)-3-[2-(morpholin-4-yl)ethyl]urea can be prepared in the following way:

A mixture of 209 mg of 1-(6-{[6-(4-fluorophenyl)[1,2,4]triazolo[4,3-b]pyridazin-3-yl]sulphanyl}-1,3-benzothiazol-2-yl)-3-(2-morpholin-4-ylethyl)urea and 241 mg of zinc in 7 cm³ of acetic acid is stirred at 20° C. for 1.5 h and then heated at 50° C. for 3.5 h. 241 mg of zinc are again added and the mixture is again left for 1 h at 50° C. After stirring overnight at 20° C., aqueous ammonia is added so that the reaction mixture changes to an alkaline pH. This mixture is extracted with ethyl acetate. The organic phase is washed with a saturated solution of sodium bicarbonate and then with brine and is then dried with magnesium sulphate and evaporated to dryness under vacuum. The residue is purified by chromatography on a Merck cartridge of 25 g of silica 15-40 μm by solid deposit, elution being carried out with a 9/1 mixture of dichloromethane/(dichloromethane:38/methanol:17/aqueous ammonia:2). 48 mg of 1-(6-{[6-(4-fluorophenyl)-7,8-dihydro-[1,2,4]triazolo[4,3-b]pyridazin-3-yl]sulphanyl}-1,3-benzothiazol-2-yl)-3-[2-(morpholin-4-yl)ethyl]urea are thus obtained in the form of a white solid, the characteristics of which are as follows:

MELTING POINT: 249.4° C. (Büchi B-545)

MASS SPECTRUM: LC/MS electrospray on WATERS UPLC-SQD: MH+=553+; MH−=551−

$^1$H NMR SPECTRUM (400 MHz, d6-DMSO) δ ppm: 2.41 (m, 6 H) 3.18 (s, 4 H) 3.29 (m partially masked, 2 H) 3.59 (m, 4 H) 6.79 (broad m, 1 H) 7.34 (t, J=8.8 Hz, 2 H) 7.49 (dd, J=8.4, 2.1 Hz, 1 H) 7.58 (d, J=8.4 Hz, 1 H) 7.95 (dd, J=8.8, 5.4 Hz, 2 H) 8.11 (broad s, 1 H) 10.99 (broad m, 1 H)

EXAMPLE 45

Ethyl {6-[(6-methoxy[1,2,4]triazolo[4,3-b]pyridazin-3-yl)sulphanyl]-1,3-benzothiazol-2-yl}carbamate a) The ethyl {6-[(6-methoxy[1,2,4]triazolo[4,3-b]pyridazin-3-yl)sulphanyl]-1,3-benzothiazol-2-yl}carbamate can be prepared according to the method described in Example 33, but using 150 mg of 6-[(6-methoxy[1,2,4]triazolo[4,3-b]pyridazin-3-yl)sulphanyl]-1,3-benzothiazol-2-amine and 0.42 cm$^3$ of ethyl chlorocarbonate, in a mixture of 1.5 cm$^3$ of pyridine and 3 cm$^3$ of dichloromethane, after 6 h at 20° C. 62 mg of ethyl {6-[(6-methoxy[1,2,4]triazolo[4,3-b]pyridazin-3-yl)sulphanyl]-1,3-benzothiazol-2-yl}carbamate are thus obtained in the form of a white solid, the characteristics of which are as follows:
MELTING POINT: >260° C.
MASS SPECTRUM: LC/MS electrospray on WATERS UPLC-SQD: MH+=403+; MH−=401−
$^1$H NMR SPECTRUM (400 MHz, d6-DMSO) δ ppm: 1.27 (t, J=7.1 Hz, 3 H) 3.89 (s, 3 H) 4.24 (q, J=7.1 Hz, 2 H) 7.09 (d, J=9.8 Hz, 1 H) 7.53 (dd, J=8.6, 2.0 Hz, 1 H) 7.65 (d, J=8.6 Hz, 1 H) 8.19 (d, J=2.0 Hz, 1 H) 8.29 (d, J=9.8 Hz, 1 H) 12.09 (broad m, 1 H)

b) The 6-[(6-methoxy[1,2,4]triazolo[4,3-b]pyridazin-3-yl)sulphanyl]-1,3-benzothiazol-2-amine can be prepared according to the method described in Example 17a, but using 2.25 g of 2-amino-1,3-benzothiazol-6-yl thiocyanate (commercial), 100 cm$^3$ of degassed ethanol, 50 mg of potassium dihydrogen phosphate in 0.5 cm$^3$ of water, 5.1 g of DL-dithiothreitol and 2 g of 3-chloro-6-methoxy[1,2,4]triazolo[4,3-b]pyridazine. 1.59 g of 6-[(6-methoxy[1,2,4]triazolo-[4,3-b]pyridazin-3-yl)sulphanyl]-1,3-benzothiazol-2-amine are thus obtained in the form of a white powder, the characteristics of which are as follows:
MASS SPECTRUM: LC/MS electrospray on WATERS UPLC-SQD: MH+=331+; MH−=329−

EXAMPLE 46

3-Methoxypropyl {6-[(6-methoxy[1,2,4]triazolo[4,3-b]pyridazin-3-yl)sulphanyl]-1,3-benzothiazol-2-yl}carbamate a) The 3-methoxypropyl {6-[(6-methoxy[1,2,4]triazolo[4,3-b]pyridazin-3-yl)sulphanyl]-1,3-benzothiazol-2-yl}carbamate can be prepared according to the method described in Example 17a, but using 489 mg of 3-methoxypropyl (6-thiocyanato-1,3-benzothiazol-2-yl)carbamate, 15 cm$^3$ of degassed ethanol, 20 mg of potassium dihydrogen phosphate in 0.5 cm$^3$ of water, 926 mg of DL-dithiothreitol and 185 mg of 3-chloro-6-methoxy[1,2,4]triazolo[4,3-b]pyridazine, after reflux for 40 h. 54 mg of 3-methoxy propyl {6-[(6-methoxy[1,2,4]triazolo[4,3-b]pyridazin-3-yl)sulphanyl]-1,3-benzothiazol-2-yl}carbamate are thus obtained in the form of a white powder, the characteristics of which are as follows:
MELTING POINT: 145° C. (Köfler block)
MASS SPECTRUM: LC/MS electrospray on WATERS UPLC-SQD: MH+=447+; MH−=445−
$^1$H NMR SPECTRUM (400 MHz, d6-DMSO) δ ppm: 1.88 (m, 2 H) 3.24 (s, 3 H) 3.42 (t, J=6.5 Hz, 2 H) 3.89 (s, 3 H) 4.24 (t, J=6.5 Hz, 2 H) 7.09 (d, J=9.8 Hz, 1 H) 7.53 (dd, J=8.6, 2.0 Hz, 1 H) 7.65 (d, J=8.6 Hz, 1 H) 8.19 (d, J=2.0 Hz, 1 H) 8.29 (d, J=9.8 Hz, 1 H) 12.10 (broad m, 1 H)

b) 3-Methoxypropyl (6-thiocyanato-1,3-benzothiazol-2-yl) carbamate can be prepared according to the method described in Example 35, but using 2 g of phenyl (6-thiocyanato-1,3-benzothiazol-2-yl)carbamate, 0.64 cm$^3$ of 3-methoxy-1-propanol and 0.47 cm$^3$ of triethylamine in 20 cm$^3$ of tetrahydrofuran. 1.02 g of 3-methoxypropyl (6-thiocyanato-1,3-benzothiazol-2-yl)carbamate are thus obtained in the form of a white solid, the characteristics of which are as follows:
MASS SPECTRUM: LC/MS electrospray on WATERS UPLC-SQD:
Retention time Tr (min)=0.86;
MH$^+$=324+; [MH—O$_2$C$_4$H$_8$]$^+$=234+(base peak)
MH$^-$=322−

EXAMPLE 47

3-Methoxypropyl[6-({6-[(2-methoxyethyl)amino][1,2,4]triazolo[4,3-b]pyridazin-3-yl}sulphanyl)-1,3-benzothiazol-2-yl]carbamate a) The 3-methoxypropyl[6-({6-[(2-methoxyethyl)amino][1,2,4]triazolo[4,3-b]pyridazin-3-yl}sulphanyl)-1,3-benzothiazol-2-yl]carbamate can be prepared according to the method described in Example 17a, but using 500 mg of 3-methoxypropyl (6-thiocyanato-1,3-benzothiazol-2-yl) carbamate, 9.6 cm$^3$ of degassed ethanol, 8 mg of potassium dihydrogen phosphate in 0.95 cm$^3$ of water, 715 mg of DL-dithiothreitol and 387 mg of 3-chloro-N-(2-methoxyethyl)[1,2,4]triazolo[4,3-b]pyridazin-6-amine, after 18 h at reflux. 128 mg of 3-methoxypropyl[6-({6-[(2-methoxyethyl)amino][1,2,4]triazolo[4,3-b]pyridazin-3-yl}sulphanyl)-1,3-benzothiazol-2-yl]carbamate are thus obtained in the form of a white solid, the characteristics of which are as follows:
MELTING POINT: 219° C. (Köfler block)
MASS SPECTRUM: LC/MS electrospray on WATERS UPLC-SQD: MH+=490+; MH−=488−
$^1$H NMR SPECTRUM (400 MHz, d6-DMSO) δ ppm: 1.88 (m, 2 H) 3.16 (s, 3 H) 3.24 (s, 3 H) 3.27-3.36 (m partially masked, 4 H) 3.42 (t, J=6.2 Hz, 2 H) 4.24 (t, J=6.6 Hz, 2 H) 6.87 (d, J=9.9 Hz, 1 H) 7.41 (dd, J=8.3, 2.0 Hz, 1 H) 7.54 (broad t, J=5.0 Hz, 1 H) 7.63 (d, J=8.3 Hz, 1 H) 7.94 (d, J=9.8 Hz, 1 H) 8.09 (d, J=2.0 Hz, 1 H) 12.08 (broad m, 1 H)

EXAMPLE 48

1-[6-({6-[(2-Methoxyethyl)amino][1,2,4]triazolo[4,3-b]pyridazin-3-yl}sulphanyl)-1,3-benzothiazol-2-yl]-3-[2-(pyrrolidin-1-yl)ethyl]urea a) The 1-[6-({6-[(2-methoxyethyl)amino][1,2,4]triazolo[4,3-b]pyridazin-3-yl}sulphanyl)-1,3-benzothiazol-2-yl]-3-[2-(pyrrolidin-1-yl)ethyl]urea can be prepared according to the method described in Example 17a, but using 500 mg of 1-[2-(pyrrolidin-1-yl)ethyl]-3-(6-sulphanyl-1,3-benzothiazol-2-yl)urea, 9.6 cm³ of degassed ethanol, 8 mg of potassium dihydrogen phosphate in 0.95 cm³ of water, 718 mg of DL-dithiothreitol and 389 mg of 3-chloro-N-(2-methoxyethyl)[1,2,4]triazolo[4,3-b]pyridazin-6-amine. 294 mg of 1-[6-({6-[(2-methoxyethyl)amino][1,2,4]triazolo[4,3-b]pyridazin-3-yl}sulphanyl)-1,3-benzothiazol-2-yl]-3-[2-(pyrrolidin-1-yl)ethyl]urea are thus obtained in the form of a white powder, the characteristics of which are as follows:

MELTING POINT: 138° C. (Köfler block)

MASS SPECTRUM: LC/MS electrospray on WATERS UPLC-SQD: MH+=514+; [MH—$C_7H_{12}N_2O$]+=374+ (base peak); MH−=512−

¹H NMR SPECTRUM (400 MHz, d6-DMSO) δ ppm: 1.70 (m, 4 H) 2.44-2.56 (m partially masked, 6 H) 3.18 (s, 3 H) 3.23-3.38 (m partially masked, 6 H) 6.81 (broad t, J=5.4 Hz, 1 H) 6.86 (d, J=9.8 Hz, 1 H) 7.38 (dd, J=8.6, 2.0 Hz, 1 H) 7.53 (m partially masked, 1 H) 7.54 (d, J=8.6 Hz, 1 H) 7.93 (d, J=9.8 Hz, 1 H) 8.03 (d, J=2.0 Hz, 1 H) 10.77 (broad m, 1 H).

b) The 1-[2-(pyrrolidin-1-yl)ethyl]-3-(6-sulphanyl-1,3-benzothiazol-2-yl)urea can be prepared according to the method described in Example 1b, but using 1.7 g of 2-({[2-(pyrrolidin-1-yl)ethyl]carbamoyl}amino)-1,3-benzothiazol-6-yl thiocyanate, 62 cm³ of degassed ethanol, 25 mg of potassium dihydrogen phosphate in 6.5 cm³ of water and 2.35 g of DL-dithiothreitol. 1.04 g of 1-[2-(pyrrolidin-1-yl)ethyl]-3-(6-sulphanyl-1,3-benzothiazol-2-yl)urea are thus obtained in the form of a cream powder, the characteristics of which are as follows:

MASS SPECTRUM: LC/MS electrospray on WATERS UPLC-SQD:

Retention time Tr (min)=0.52;

MH⁺=323+; MH⁻=321−.

c) The 2-({[2-(pyrrolidin-1-yl)ethyl]carbamoyl}amino)-1,3-benzothiazol-6-yl thiocyanate can be prepared according to the method described in Example 9c, but using 2 g of phenyl (6-thiocyanato-1,3-benzothiazol-2-yl)carbamate ester, 60 cm³ of tetrahydrofuran and 0.852 cm³ of N-(2-aminoethyl)pyrrolidine. 1.7 g of a yellow powder of 2-({[2-(pyrrolidin-1-yl)ethyl]carbamoyl}amino)-1,3-benzothiazol-6-yl thiocyanate as a mixture with 1-[2-(pyrrolidin-1-yl)ethyl]-3-(6-sulphanyl-1,3-benzothiazol-2-yl)urea and its corresponding disulphide are thus obtained. This mixture is used as it is.

EXAMPLE 49

1-{6-[(6-Methoxy[1,2,4]triazolo[4,3-b]pyridazin-3-yl)sulphanyl]-1,3-benzothiazol-2-yl}-3-[2-(pyrrolidin-1-yl)ethyl]urea a) The 1-{6-[(6-methoxy[1,2,4]triazolo[4,3-b]pyridazin-3-yl)sulphanyl]-1,3-benzothiazol-2-yl}-3-[2-(pyrrolidin-1-yl)ethyl]urea was prepared according to the method described in Example 17a, but using 547 mg of 1-[2-(pyrrolidin-1-yl)ethyl]-3-(6-sulphanyl-1,3-benzothiazol-2-yl)urea, 25 cm³ of degassed ethanol, 8 mg of potassium dihydrogen phosphate in 0.2 cm³ of water, 787 mg of DL-dithiothreitol and 313 mg of 3-chloro-6-methoxy[1,2,4]-triazolo[4,3-b]pyridazine. 189 mg of 1-{6-[(6-methoxy[1,2,4]triazolo[4,3-b]pyridazin-3-yl)sulphanyl]-1,3-benzothiazol-2-yl}-3-[2-(pyrrolidin-1-yl)ethyl]urea are thus obtained in the form of a white powder, the characteristics of which are as follows:

MELTING POINT: 224° C. (Köfler block)

MASS SPECTRUM: LC/MS electrospray on WATERS UPLC-SQD: MH+=471; MH−=469−

¹H NMR SPECTRUM (400 MHz, d6-DMSO) δ ppm: 1.70 (m, 4 H) 2.44-2.57 (m partially masked, 6 H) 3.27 (m partially masked, 2 H) 3.90 (s, 3 H) 6.81 (broad m, 1 H) 7.09 (d, J=9.8 Hz, 1 H) 7.50 (dd, J=8.6, 2.0 Hz, 1 H) 7.57 (d, J=8.6 Hz, 1 H) 8.14 (d, J=2.0 Hz, 1 H) 8.28 (d, J=9.8 Hz, 1 H) 10.79 (broad m, 1 H)

EXAMPLE 50

6-[(6-Ethoxy[1,2,4]triazolo[4,3-b]pyridazin-3-yl)sulphanyl]-1,3-benzothiazol-2-amine a) The 6-[(6-ethoxy[1,2,4]triazolo[4,3-b]pyridazin-3-yl)sulphanyl]-1,3-benzothiazol-2-amine was prepared according to the method described in Example 17a, but using 587 mg of 2-amino-1,3-benzothiazol-6-yl thiocyanate (commercial), 20 cm³ of degassed ethanol, 13 mg of potassium dihydrogen phosphate in 0.2 cm³ of water, 1.31 g of DL-dithiothreitol and 562 mg of 3-chloro-6-ethoxy[1,2,4]triazolo[4,3-b]pyridazine. 783 mg of 6-[(6-ethoxy[1,2,4]triazolo[4,3-b]pyridazin-3-yl)sulphanyl]-1,3-benzothiazol-2-amine are thus obtained in the form of a whitish powder, the characteristics of which are as follows:

MELTING POINT: 240° C. (Köfler block)

MASS SPECTRUM: LC/MS electrospray on WATERS UPLC-SQD: MH+=345+; MH−=343−

¹H NMR SPECTRUM (400 MHz, d6-DMSO) δ ppm: 1.33 (t, J=7.0 Hz, 3 H) 4.31 (q, J=7.0 Hz, 2 H) 7.05 (d, J=9.8 Hz, 1 H) 7.29 (d, J=8.3 Hz, 1 H) 7.38 (dd, J=8.3, 2.0 Hz, 1 H) 7.63 (broad s, 2 H) 7.92 (d, J=2.0 Hz, 1 H) 8.25 (d, J=9.8 Hz, 1 H).

EXAMPLE 51

2-Methylpropan-2-yl(6-{[6-(4-chloro-2-hydroxybutoxy)[1,2,4]triazolo[4,3-b]pyridazin-3-yl]sulphanyl}-1,3-benzothiazol-2-yl)carbamate a) The 2-methylpropan-2-yl (6-{[6-(4-chloro-2-hydroxybutoxy)-[1,2,4]triazolo[4,3-b]pyridazin-3-yl]sulphanyl}-1,3-benzothiazol-2-yl)carbamate can be prepared according to the method described in Example 17a, but using 307 mg of 1,1-dimethylethyl (6-thiocyanato-1,3-benzothiazol-2-yl)carbamate, 8 cm³ of degassed ethanol, 8 mg of potassium dihydrogen phosphate in 0.8 cm³ of water, 462 mg of DL-dithiothreitol and 241 mg of 3-chloro-6-(oxetan-2-ylmethoxy)[1,2,4]triazolo[4,3-b]pyridazine. 116 mg of 2-methylpropan-2-yl(6-{[6-(4-chloro-2-hydroxybutoxy)[1,2,4]triazolo[4,3-b]pyridazin-3-yl]sulphanyl}-1,3-benzothiazol-2-yl)carbamate are thus obtained in the form of a white solid, the characteristics of which are as follows:

MELTING POINT: 206° C. (Köfler block)

MASS SPECTRUM: LC/MS electrospray on WATERS UPLC-SQD: MH+=523+; MH−=521−

¹H NMR SPECTRUM (500 MHz, d6-DMSO) δ ppm: 1.50 (s, 9 H) 1.85 (m, 2 H) 3.71 (m, 2 H) 3.98 (m, 1 H) 4.12 (m, 2 H) 5.20 (d, J=5.5 Hz, 1 H) 7.09 (d, J=9.9 Hz, 1 H) 7.49 (dd, J=8.5, 1.9 Hz, 1 H) 7.63 (d, J=8.5 Hz, 1 H) 8.15 (d, J=1.9 Hz, 1 H) 8.29 (d, J=9.9 Hz, 1 H) 11.83 (broad m, 1 H)

EXAMPLE 52

2-Methylpropan-2-yl[6-({6-[3-chloro-2-(hydroxymethyl)-2-methylpropoxy]-[1,2,4]triazolo[4,3-b]pyridazin-3-yl}sulphanyl)-1,3-benzothiazol-2-yl]carbamate a) The 2-methylpropan-2-yl[6-({6-[3-chloro-2-(hydroxymethyl)-2-methylpropoxy][1,2,4]triazolo[4,3-b]pyridazin-3-yl}sulphanyl)-1,3-benzothiazol-2-yl]carbamate can be prepared according to the method described in Example 17a, but using 307 mg of 1,1-dimethylethyl (6-thiocyanato-1,3-benzothiazol-2-yl)carbamate, 8 cm$^3$ of degassed ethanol, 8 mg of potassium dihydrogen phosphate in 0.8 cm$^3$ of water, 462 mg of DL-dithiothreitol and 254 mg of 3-chloro-6-[(1-methyloxetan-3-yl)methoxy][1,2,4]triazolo[4,3-b]pyridazine. 98 mg of 2-methylpropan-2-yl[6-({6-[3-chloro-2-(hydroxymethyl)-2-methylpropoxy][1,2,4]triazolo[4,3-b]pyridazin-3-yl}sulphanyl)-1,3-benzothiazol-2-yl]carbamate are thus obtained in the form of a white solid, the characteristics of which are as follows:
MELTING POINT: 180.6° C. (Büchi B-545)
MASS SPECTRUM: LC/MS electrospray on WATERS UPLC-SQD: MH+=537+; MH−=535−
$^1$H NMR SPECTRUM (400 MHz, d6-DMSO) δ ppm: 0.98 (s, 3 H) 1.51 (s, 9 H) 3.39 (m, 2 H) 3.63 (m, 2 H) 4.06 (m, 2 H) 4.87 (t, J=5.5 Hz, 1 H) 7.10 (d, J=9.9 Hz, 1 H) 7.52 (dd, J=8.4, 2.1 Hz, 1 H) 7.63 (d, J=8.4 Hz, 1 H) 8.14 (d, J=2.1 Hz, 1 H) 8.29 (d, J=9.9 Hz, 1 H) 11.82 (broad m, 1 H)

b) The 3-chloro-6-[(3-methyloxetan-3-yl)methoxy][1,2,4]triazolo[4,3-b]pyridazine can be prepared according to the method described in Example 34b, but using 1.51 g of 3,6-dichloro[1,2,4]triazolo[4,3-b]pyridazine (commercial), 0.90 cm$^3$ of (3-methyloxetan-3-yl)methanol and 1.1 g of potassium carbonate in 16 cm$^3$ of N,N-dimethylformamide, after heating at 100° C. for 6 h, and then overnight at 20° C. 1.42 g of 3-chloro-6-[(3-methyloxetan-3-yl)methoxy][1,2,4]triazolo[4,3-b]pyridazine are thus obtained in the form of a white solid, the characteristics of which are as follows:
MASS SPECTRUM: LC/MS electrospray on WATERS UPLC-SQD:
Retention time Tr (min)=2.7;
MH+=255+.

EXAMPLE 53

6-{[6-(3-Fluorophenyl)[1,2,4]triazolo[4,3-b]pyridazin-3-yl]sulphanyl}-1,3-benzothiazol-2-amine a) The 6-{[6-(3-fluorophenyl)[1,2,4]triazolo[4,3-b]pyridazin-3-yl]sulphanyl}-1,3-benzothiazol-2-amine can be prepared according to the method described in Example 17a, but using 416 mg of 2-amino-1,3-benzothiazol-6-yl thiocyanate (commercial), 23 cm$^3$ of degassed ethanol, 9.3 mg of potassium dihydrogen phosphate in 0.22 cm$^3$ of water, 930 mg of DL-dithiothreitol and 413 mg of 3-chloro-6-(3-fluorophenyl)[1,2,4]triazolo[4,3-b]pyridazine. 242 mg of 6-{[6-(3-fluorophenyl)[1,2,4]triazolo[4,3-b]pyridazin-3-yl]sulphanyl}-1,3-benzothiazol-2-amine are thus obtained in the form of a white powder, the characteristics of which are as follows:
MELTING POINT: >255° C. (Büchi B-545)
MASS SPECTRUM: LC/MS electrospray on WATERS UPLC-SQD: MH+=395+; MH−=393−
$^1$H NMR SPECTRUM (300 MHz, d6-DMSO) δ ppm: 7.31 (d, J=8.5 Hz, 1 H) 7.43 (dd, J=8.5, 2.0 Hz, 1 H) 7.46 (m partially masked, 1 H) 7.57-7.67 (m, 3 H) 7.84 (ddd, J=10.5, 2.6, 1.7 Hz, 1 H) 7.91 (broad d, J=8.1 Hz, 1 H) 7.98 (d, J=2.0 Hz, 1 H) 8.04 (d, J=9.8 Hz, 1 H) 8.52 (d, J=9.8 Hz, 1 H).

b) The 3-chloro-6-(3-fluorophenyl)[1,2,4]triazolo[4,3-b]pyridazine can be prepared according to the method described in Example 17c, but using 820 mg of 3-fluorophenylboronic acid, 1.84 g of barium hydroxide octahydrate, 0.43 g of [1,1'-bis(diphenylphosphino)ferrocene]dichloro-palladium(II) in a complex with dichloromethane (1:1) and 1 g of commercial 3,6-dichloro[1,2,4]triazolo[4,3-b]pyridazine in 8 cm$^3$ of degassed N,N-dimethylformamide, and 1.96 cm$^3$ of water, after 1.5 h at 80° C. 506 mg of 3-chloro-6-(3-fluorophenyl)[1,2,4]triazolo[4,3-b]pyridazine are thus obtained in the form of a beige powder, the characteristics of which are as follows:
MASS SPECTRUM: LC/MS electrospray on WATERS UPLC-SQD:
Retention time Tr (min)=0.81;
MH+=249+.

EXAMPLE 54

6-{[6-(3-Fluorophenyl)-7,8-dihydro[1,2,4]triazolo[4,3-b]pyridazin-3-yl]sulphanyl}-1,3-benzothiazol-2-amine a) The 6-{[6-(3-fluorophenyl)-7,8-dihydro[1,2,4]triazolo[4,3-b]pyridazin-3-yl]sulphanyl}-1,3-benzothiazol-2-amine can be prepared in a manner similar to the method described in Example 44, but using 300 mg of 6-{[6-(3-fluorophenyl)[1,2,4]triazolo[4,3-b]pyridazin-3-yl]sulphanyl}-1,3-benzothiazol-2-amine and 1.49 mg of zinc in 40 cm$^3$ of glacial acetic acid, after 3 h at 50° C. 125 mg of 6-{[6-(3-fluorophenyl)-7,8-dihydro[1,2,4]triazolo[4,3-b]pyridazin-3-yl]sulphanyl}-1,3-benzothiazol-2-amine are thus obtained in the form of a white solid, the characteristics of which are as follows:
MELTING POINT: >255° C. (Büchi B-545)
MASS SPECTRUM: LC/MS electrospray on WATERS UPLC-SQD: MH+=397+; MH−=395−
$^1$H NMR SPECTRUM (300 MHz, d6-DMSO) δ ppm: 3.17 (s, 4 H) 7.32 (d, J=8.4 Hz, 1 H) 7.40 (dd, J=8.4, 2.0 Hz, 1 H) 7.43 (m partially masked, 1 H) 7.56 (td, J=8.0, 6.0 Hz, 1 H) 7.62-7.70 (m, 3 H) 7.73 (broad d, J=8.0 Hz, 1 H) 7.93 (d, J=2.0 Hz, 1 H).

EXAMPLE 55

N-(6-{[6-(4-Fluorophenyl)[1,2,4]triazolo[4,3-b]pyridazin-3-yl]sulphanyl}-1,3-benzothiazol-2-yl)morpholine-4-carboxamide a) The N-(6-{[6-(4-fluorophenyl)[1,2,4]triazolo[4,3-b]pyridazin-3-yl]sulphanyl}-1,3-benzothiazol-2-yl)morpholine-4-carboxamide can be prepared according to the method described in Example 17a, but using 640 mg of 2-[(morpholin-4-ylcarbonyl)amino]-1,3-benzothiazol-6-yl thiocyanate, 20 cm$^3$ of degassed ethanol, 10 mg of potassium dihydrogen phosphate in 0.5 cm$^3$ of water, 926 mg of DL-dithiothreitol and 496 mg of 3-chloro-6-(4-fluorophenyl)[1,2,4]triazolo[4,3-b]pyridazine. 133 mg of N-(6-{[6-(4-fluorophenyl)[1,2,4]triazolo[4,3-b]pyridazin-3-yl]sulphanyl}-1,3-benzothiazol-2-yl)morpholine-4-carboxamide are thus obtained in the form of a beige solid, the characteristics of which are as follows:

MELTING POINT: >255° C. (Büchi B-545)

MASS SPECTRUM: LC/MS electrospray on WATERS UPLC-SQD: MH+=508+; MH−=506−

¹H NMR SPECTRUM (400 MHz, d6-DMSO) δ ppm: 3.49-3.63 (m, 8 H) 7.41 (t, J=9.0 Hz, 2 H) 7.52-7.56 (broad m, 2 H) 8.02 (d, J=9.8 Hz, 1 H) 8.08-8.15 (m masked, 1 H) 8.11 (dd, J=9.0, 5.3 Hz, 2 H) 8.50 (d, J=9.8 Hz, 1 H) 11.52 (broad m, 1 H)

b) The 2-[(morpholin-4-ylcarbonyl)amino]-1,3-benzothiazol-6-yl thiocyanate can be prepared according to the method described in Example 9c, but using 2.29 g of phenyl (6-thiocyanato-1,3-benzothiazol-2-yl)carbamate ester in 70 cm³ of tetrahydrofuran and 0.6 cm³ of morpholine, after 4 h at 50° C. 2.11 g of 2-[(morpholin-4-ylcarbonyl)amino]-1,3-benzothiazol-6-yl thiocyanate are thus obtained in the form of a white solid, the characteristics of which are as follows:

MASS SPECTRUM: LC/MS electrospray on Waters ZQ:

Retention time Tr (min)=3.42;

[M+H]+: m/z 321; [M−H]−: m/z 319

EXAMPLE 56

6-{[6-(2-Fluorophenyl)[1,2,4]triazolo[4,3-b]pyridazin-3-yl]sulphanyl}-1,3-benzothiazol-2-amine a) The 6-{[6-(2-fluorophenyl)[1,2,4]triazolo[4,3-b]pyridazin-3-yl]sulphanyl}-1,3-benzothiazol-2-amine can be prepared according to the method described in Example 17a, but using 167 mg of 2-amino-1,3-benzothiazol-6-yl thiocyanate (commercial), a mixture of 5 cm³ of ethanol and 5 cm³ of degassed tetrahydrofuran, 3.71 mg of potassium dihydrogen phosphate in 0.1 cm³ of water, 372 mg of DL-dithiothreitol and 200 mg of 3-chloro-6-(2-fluorophenyl)[1,2,4]triazolo[4,3-b]pyridazine. 169 mg of 6-{[6-(2-fluorophenyl)-[1,2,4]triazolo[4,3-b]pyridazin-3-yl]sulphanyl}-1,3-benzothiazol-2-amine are thus obtained in the form of a white powder, the characteristics of which are as follows:

MELTING POINT: >255° C. (Büchi B-545)

MASS SPECTRUM: LC/MS electrospray on WATERS UPLC-SQD: MH+=395+; MH−=393−

¹H NMR SPECTRUM (300 MHz, d6-DMSO) δ ppm: 7.31 (d, J=8.5 Hz, 1 H) 7.36-7.50 (m, 3 H) 7.61-7.76 (m, 5 H) 7.95 (d, J=2.0 Hz, 1 H) 8.49 (d, J=9.8 Hz, 1 H)

b) The 3-chloro-6-(2-fluorophenyl)[1,2,4]triazolo[4,3-b]pyridazine can be prepared according to the method described in Example 17c but using 820 mg of 2-fluorophenylboronic acid, 1.84 g of barium hydroxide octahydrate, 0.43 g of [1,1'-bis(diphenylphosphino)ferrocene] dichloropalladium(II) in a complex with dichloromethane (1:1) and 1 g of commercial 3,6-dichloro[1,2,4]triazolo[4,3-b]pyridazine in 8 cm³ of degassed N,N-dimethylformamide and 1.96 cm³ of water, after 4.5 h at 80° C. 416 mg of 3-chloro-6-(2-fluorophenyl)[1,2,4]-triazolo[4,3-b]pyridazine are thus obtained in the form of beige crystals, the characteristics of which are as follows:

MASS SPECTRUM: LC/MS electrospray on WATERS UPLC-SQD:

Retention time Tr (min)=0.77;

MH+=249+.

EXAMPLE 57

N-(2-Methoxyethyl)-3-({2-[(2-methylbutyl)amino]-1,3-benzothiazol-6-yl}sulphanyl)[1,2,4]triazolo[4,3-b]pyridazin-6-amine a) The N-(2-methoxyethyl)-3-({2-[(2-methylbutyl)amino]-1,3-benzothiazol-6-yl}sulphanyl)[1,2,4]triazolo[4,3-b] pyridazin-6-amine can be prepared in the following way:

0.523 cm³ of 2-methylbutylamine is added to a solution of 400 mg of 2-bromo-1,3-benzothiazol-6-yl thiocyanate in 7 cm³ of tetrahydrofuran. After 2 h at 20° C., the suspension is concentrated to dryness under vacuum. The reaction residue is taken up in 18 cm³ of ethanol and 8 mg of potassium dihydrogen phosphate in 1.8 cm³ of water and 684 mg of DL-dithiothreitol are added thereto. The mixture is heated at 80° C. for 2 h and then 170 mg of 3-chloro-N-(2-methoxyethyl)[1,2,4]triazolo[4,3-b]pyridazin-6-amine (24b) are added and the reaction is heated for a further 18 h, and then the reaction medium is concentrated to dryness under vacuum. The residue is chromatographed by solid deposit on Biotage Quad Si25 (KP-SIL, 60 A; 32-63 μm) elution being carried out with a dichloromethane/(dichloromethane:38/methanol: 17/aqueous ammonia:2) gradient of 95/5 to 92/8. 116 mg of N-(2-methoxyethyl)-3-({2-[(2-methylbutyl)amino]-1,3-benzothiazol-6-yl}sulphanyl)[1,2,4]triazolo[4,3-b]pyridazin-6-amine are thus obtained in the form of a pale yellow powder, the characteristics of which are as follows:

MELTING POINT: sticks at 84° C. (Köfler block)

MASS SPECTRUM: LC/MS electrospray on WATERS UPLC-SQD: MH+=444+; MH−=442−

¹H NMR SPECTRUM (400 MHz, d6-DMSO) δ ppm: 0.87 (d, J=7.5 Hz, 3 H) 0.89 (d, J=6.9 Hz, 3 H) 1.14 (m, 1 H) 1.42 (m, 1 H) 1.67 (m, 1 H) 3.07-3.42 (m partially masked, 6 H) 3.21 (s, 3 H) 6.85 (d, J=9.8 Hz, 1 H) 7.30 (d, J=1.3 Hz, 2 H) 7.52 (broad t, J=5.4 Hz, 1 H) 7.83 (t, J=1.3 Hz, 1 H) 7.91 (d, J=9.8 Hz, 1 H) 8.13 (broad t, J=5.5 Hz, 1 H).

b) The 2-bromo-1,3-benzothiazol-6-ylthiocyanate can be prepared in the following way:

A mixture of 6.5 g of cuprous bromide in 666 cm³ of acetonitrile is flushed with argon for 5 min. The solution is cooled to 0-5° C. and then 4.3 cm³ of tert-butyl nitrite are added. 5 g of 2-amino-1,3-benzothiazol-6-yl thiocyanate (commercial) are then added portionwise at 0° C. The reaction is stirred for 3 h at 20° C. and then concentrated to dryness under vacuum. The residue is taken up in ethyl acetate and then washed with a saturated solution of sodium bicarbonate. The organic phase is dried over magnesium sulphate and then concentrated to dryness under vacuum. 5.05 g of 2-bromo-1,3-benzothiazol-6-yl thiocyanate are thus obtained in the form of a golden yellow powder, the characteristics of which are as follows:

MASS SPECTRUM: LC/MS electrospray on WATERS UPLC-SQD: MH+=271, 273+; MH−=481, 483−.

EXAMPLE 58

N-{6-[(6-Ethoxy[1,2,4]triazolo[4,3-b]pyridazin-3-yl) sulphanyl]-1,3-benzothiazol-2-yl}-3-methoxypropanamide a) The N-{6-[(6-ethoxy[1,2,4]triazolo[4,3-b]pyridazin-3-yl) sulphanyl]-1,3-benzothiazol-2-yl}-3-methoxypropanamide can be prepared in the following way:

7 mg of potassium dihydrogen phosphate in 0.2 cm³ of water and 699 mg of DL-dithiothreitol are added to a degassed solution of 443 mg of 2-[(3-methoxpropanoyl)

amino]-1,3-benzothiazol-6-yl thiocyanate in 10 cm³ of ethanol and 10 cm³ of tetrahydrofuran. The reaction is heated at 80° C. for 15 min and then 301 mg of 3-chloro-6-ethoxy[1,2,4]triazolo[4,3-b]pyridazine are added and the reaction is heated for a further 24 h. The reaction medium is then evaporated to dryness under reduced pressure. The residue is taken up in 20 cm³ of ethanol and 57 mg of sodium borohydride are added and the mixture is then brought to reflux for 18 h. The reaction medium is concentrated under reduced pressure. The residue is chromatographed by solid deposit on Biotage Quad 12/25 (KP-SIL, 60 A; 32-63 µm), elution being carried out with a gradient of 100% dichloromethane to 97/3 dichloromethane/methanol. 268 mg of N-{6-[(6-ethoxy[1,2,4]triazolo[4,3-b]pyridazin-3-yl)sulphanyl]-1,3-benzothiazol-2-yl}-3-methoxpropanamide are thus obtained in the form of a white powder, the characteristics of which are as follows:
MELTING POINT: 202° C. (Köfler block)
MASS SPECTRUM: LC/MS electrospray on WATERS UPLC-SQD: MH+=431+; MH-=429-
¹H NMR SPECTRUM (400 MHz, d6-DMSO) δ ppm: 1.27 (t, J=7.1 Hz, 3 H) 2.73 (t, J=6.1 Hz, 2 H) 3.24 (s, 3 H) 3.65 (t, J=6.1 Hz, 2 H) 4.27 (q, J=7.1 Hz, 2 H) 7.07 (d, J=9.8 Hz, 1 H) 7.52 (dd, J=8.6, 2.0 Hz, 1 H) 7.70 (d, J=8.6 Hz, 1 H) 8.19 (d, J=2.0 Hz, 1 H) 8.28 (d, J=9.8 Hz, 1 H) 12.41 (broad m, 1 H).

b) The 2-[(3-methoxypropanoyl)amino]-1,3-benzothiazol-6-ylthiocyanate can be prepared in a manner similar to the method described in Example 18b, but using 2.1 g of commercial 2-amino-6-thiocyanatobenzothiazole and 1.2 cm³ of 3-methoxypropionic acid chloride in 10 cm³ of pyridine and 10 cm³ of dichloromethane, after reaction for 2.5 h, at 20° C. 2.25 g of 2-[(3-methoxypropanoyl)amino]-1,3-benzothiazol-6-ylthiocyanate are thus obtained in the form of an orange solid, the characteristics of which are as follows:
MASS SPECTRUM: LC/MS electrospray on WATERS UPLC-SQD: Retention time Tr (min)=0.77; MH+=294+; [M-H]-=292-.

EXAMPLE 59

,3-b]pyridazin-3-yl)sulphanyl]-1,3-benzothiazol-2-yl}urea a) The 1-cyclopropyl-3-{6-[(6-ethoxy[1,2,4]triazolo[4,3-b]pyridazin-3-yl)sulphanyl]-1,3-benzothiazol-2-yl}urea can be prepared according to the method described in Example 9c, but using 71 mg of phenyl {6-[(6-ethoxy[1,2,4]triazolo[4,3-b]pyridazin-3-yl)sulphanyl]-1,3-benzothiazol-2-yl}carbamate in 5 cm³ of THF with 0.063 cm³ of triethylamine and 0.021 cm³ of cyclopropylamine, after 4.5 h at 60° C. The reaction residue is chromatographed by solid deposit on Biotage Quad 12/25 (KP-SIL, 60 A; 32-63 µm), elution being carried out with a dichloromethane/methanol gradient of 99/1 to 96/4. 54 mg of 1-cyclopropyl-3-{64(6-ethoxy[1,2,4]triazolo[4,3-N-pyridazin-3-yl)sulphanyl]-1,3-benzothiazol-2-yl}urea are thus obtained in the form of a white powder, the characteristics of which are as follows:
MELTING POINT: 214° C. (Köfler block)
MASS SPECTRUM: LC/MS electrospray on WATERS UPLC-SQD: MH+=428+; MH-=426-
¹H NMR SPECTRUM (400 MHz, d6-DMSO) δ ppm: 0.48 (m, 2 H) 0.67 (m, 2 H) 1.29 (t, J=7.0 Hz, 3 H) 2.61 (m, 1 H) 4.29 (q, J=7.0 Hz, 2 H) 6.95 (broad m, 1 H) 7.06 (d, J=9.8 Hz, 1 H) 7.46 (dd, J=8.6, 2.0 Hz, 1 H) 7.57 (d, J=8.6 Hz, 1 H) 8.12 (d, J=2.0 Hz, 1 H) 8.27 (d, J=9.8 Hz, 1 H) 10.62 (broad m, 1 H).

b) The phenyl {6-[(6-ethoxy[1,2,4]triazolo[4,3-b]pyridazin-3-yl)sulphanyl]-1,3-benzothiazol-2-yl}carbamate can be prepared in a manner similar to the method described in Example 9d, but with pyridine as base and solvent, using 294 mg of 6-[(6-ethoxy[1,2,4]triazolo[4,3-b]pyridazin-3-yl)sulphanyl]-1,3-benzothiazol-2-amine and 0.42 cm³ of phenyl chlorocarbonate in 10 cm³ of pyridine after 5 h of contact at 20° C. 202 mg of phenyl {6-[(6-ethoxy[1,2,4]triazolo[4,3-b]pyridazin-3-yl)sulphanyl]-1,3-benzothiazol-2-yl}-carbamate are thus obtained in the form of a white powder, the characteristics of which are as follows:
MASS SPECTRUM: LC/MS electrospray on WATERS UPLC-SQD: MH+=465+; MH-=463-.

EXAMPLE 60

N-(6-{[6-(4-Fluorophenyl)[1,2,4]triazolo[4,3-b]pyridazin-3-yl]sulphanyl}-1,3-benzothiazol-2-yl)cyclopropanecarboxamide a) The N-(6-{[6-(4-fluorophenyl)[1,2,4]triazolo[4,3-b]pyridazin-3-yl]sulphanyl}-1,3-benzothiazol-2-yl)cyclopropanecarboxamide can be prepared in a manner similar to the method described in Example 18b, but using 591 mg of 6-{[6-(4-fluorophenyl)[1,2,4]triazolo[4,3-b]pyridazin-3-yl]sulphanyl}-1,3-benzothiazol-2-amine in 3 cm³ of pyridine with 0.46 cm³ of cyclopropanecarboxylic acid chloride. After reaction for 5 h at 20° C., water is added and the precipitate is spin-filter-dried, and washed with water and with ether. After chromatography of the precipitate on silica, 201 mg of N-(6-{[6-(4-fluorophenyl)[1,2,4]triazolo[4,3-b]pyridazin-3-yl]sulphanyl}-1,3-benzothiazol-2-yl)cyclopropanecarboxamide are obtained in the form of a white powder, the characteristics of which are as follows:
MELTING POINT: >255° C. (Büchi B-545)
MASS SPECTRUM: LC/MS electrospray on WATERS UPLC-SQD: MH+=463+; MH-=461-
¹H NMR SPECTRUM (400 MHz, d6-DMSO) δ ppm: 0.92-0.98 (m, 4 H) 1.98 (m, 1 H) 7.40 (t, J=8.8 Hz, 2 H) 7.57 (dd, J=8.6, 2.0 Hz, 1 H) 7.71 (d, J=8.6 Hz, 1 H) 8.03 (d, J=9.8 Hz, 1 H) 8.10 (dd, J=8.8, 5.4 Hz, 2 H) 8.21 (d, J=2.0 Hz, 1 H) 8.51 (d, J=9.8 Hz, 1 H) 12.67 (broad m, 1 H).

EXAMPLE 61

N-(6-{[6-(4-Fluorophenyl)-7,8-dihydro[1,2,4]triazolo[4,3-b]pyridazin-3-yl]sulphanyl}-1,3-benzothiazol-2-yl)cyclopropanecarboxamide a) The N-(6-{[6-(4-fluorophenyl)-7,8-dihydro[1,2,4]triazolo[4,3-b]pyridazin-3-yl]sulphanyl}-1,3-benzothiazol-2-yl)cyclopropanecarboxamide can be prepared in a manner similar to the method described in Example 44, but using 162 mg of N-(6-{[6-(4-fluorophenyl)[1,2,4]triazolo[4,3-b]pyridazin-3-yl]sulphanyl}-1,3-benzothiazol-2-yl)cyclopropanecarboxamide in 5 cm³ of acetic acid and 690 mg of zinc, at 50° C. for 24 h. 143 mg of N-(6-{[6-(4-fluorophenyl)-7,8-dihydro[1,2,4]triazolo[4,3-b]pyridazin-3-yl]sulphanyl}-1,3-benzothiazol-2-yl)cyclopropanecarboxamide are thus obtained in the form of a white solid, the characteristics of which are as follows:
MELTING POINT: 185° C. (Köfler block)
MASS SPECTRUM: LC/MS electrospray on WATERS UPLC-SQD: MH+=465+; MH-=463-
¹H NMR SPECTRUM (400 MHz, d6-DMSO) δ ppm: 0.96 (m, 4 H) 2.00 (m, 1 H) 3.19 (s, 4 H) 7.33 (t, J=8.9 Hz, 2 H) 7.57 (dd, J=8.6, 2.0 Hz, 1 H) 7.73 (d, J=8.6 Hz, 1 H) 7.94 (dd, J=8.9, 5.5 Hz, 2 H) 8.19 (d, J=2.0 Hz, 1 H) 12.69 (broad m, 1 H).

EXAMPLE 62

3-[(2-Amino-1,3-benzothiazol-6-yl)sulphanyl]-N-cyclohexyl[1,2,4]triazolo[4,3-b]pyridazin-6-amine a) The 3-[(2-amino-1,3-benzothiazol-6-yl)sulphanyl]-N-cyclohexyl[1,2,4]-triazolo[4,3-b]pyridazin-6-amine can be prepared according to the method described in Example 17a, but using 500 mg of 2-amino-1,3-benzothiazol-6-yl thiocyanate (commercial), 10 cm$^3$ of degassed ethanol, 12 mg of potassium dihydrogen phosphate in 1 cm$^3$ of water, 1.12 g of DL-dithiothreitol and 607 mg of 3-chloro-N-cyclohexyl[1,2,4]triazolo[4,3-b]pyridazin-6-amine. 768 mg of 3-[(2-amino-1,3-benzothiazol-6-yl)sulphanyl]-N-cyclohexyl[1,2,4]-triazolo[4,3-b]pyridazin-6-amine are thus obtained in the form of a white powder, the characteristics of which are as follows:
MELTING POINT: 215° C. (Köfler block)
MASS SPECTRUM: LC/MS Electrospray on WATERS UPLC-SQD: MH+=398+; [M+2H+CH$_3$CN]+=220; MH−=396−
$^1$H NMR SPECTRUM (400 MHz, d6-DMSO) δ ppm: 1.06-1.34 (m, 5 H) 1.58 (m, 1 H) 1.66 (m, 2 H) 1.81 (m 2 H) 3.44 (m, 1 H) 6.83 (d, j=9.8 Hz, 1 H) 7.29-7.40 (m, 3 H) 7.84 (d, j=1.7 Hz, 1 H) 7.92 (d, j=9.8 Hz, 1 H) 8.53 (broad m, 2 H)

b) The 3-chloro-N-cyclohexyl[1,2,4]triazolo[4,3-b]pyridazin-6-amine can be prepared according to the method described in Example 16b, but using 5 g of 3,6-dichloro[1,2,4]triazolo[4,3-b]pyridazine, 50 cm$^3$ of N,N-dimethylformamide, 3.4 cm$^3$ of cyclohexylamine and 11.22 cm$^3$ of triethylamine, after reaction at 20° C. for 20 h and at 50° C. for 4 h, and then precipitation of the product by adding water. 4.45 g of 3-chloro-N-cyclohexyl[1,2,4]triazolo[4,3-b]pyridazin-6-amine are thus obtained, by precipitation from water, in the form of a yellowy-white powder, the characteristics of which are as follows:
MASS SPECTRUM: LC/MS Electrospray on WATERS UPLC-SQD: MH+=252+; MH−=250−
$^1$H NMR SPECTRUM (400 MHz, d6-DMSO) δ ppm: 1.13-1.43 (m, 5 H) 1.60 (m, 1 H) 1.73 (m, 2 H) 1.99 (m, 2 H) 3.66 (m, 1 H) 6.86 (d, J=9.9 Hz, 1 H) 7.42 (d, J=7.1 Hz, 1 H) 7.91 (d, J=9.9 Hz, 1 H)

EXAMPLE 63

6-{[6-(Cyclohexyloxy)[1,2,4]triazolo[4,3-b]pyridazin-3-yl]sulphanyl}-1,3-benzothiazol-2-amine a) The 6-{[6-(cyclohexyloxy)[1,2,4]triazolo[4,3-b]pyridazin-3-yl]sulphanyl}-1,3-benzothiazol-2-amine can be prepared according to the method described in Example 17a, but using 149 mg of 2-amino-1,3-benzothiazol-6-yl thiocyanate (commercial), 20 cm$^3$ of degassed ethanol, 4 mg of potassium dihydrogen phosphate in 0.2 cm$^3$ of water, 333 mg of DL-dithiothreitol and 182 mg of 3-chloro-6-(cyclohexyloxy)[1,2,4]triazolo[4,3-b]pyridazine. 130 mg of 6-{[6-(cyclohexyloxy)[1,2,4]triazolo[4,3-b]pyridazin-3-yl]sulphanyl}-1,3-benzothiazol-2-amine are obtained in the form of a yellowish powder, the characteristics of which are as follows:
MELTING POINT: >260° C. (Köfler block)
MASS SPECTRUM: LC/MS Electrospray on WATERS UPLC-SQD: MH+m/z=399+; MH−=397−
$^1$H NMR SPECTRUM (400 MHz, d6-DMSO) δ ppm: 1.18-1.47 (m, 5 H) 1.54-(m, 1 H) 1.67 (m, 2 H) 1.88 (m, 2 H) 4.76 (m, 1 H) 7.01 (d, J=9.8 Hz, 1 H) 7.23-7.32 (m, 2 H) 7.60 (broad s, 2 H) 7.81 (broad s, 1 H) 8.25 (d, j=9.8 Hz, 1 H)

b) The 3-chloro-6-(cyclohexyloxy)[1,2,4]triazolo[4,3-b]pyridazine can be prepared in the following way:
106 mg of sodium hydride at 60% in oil are added to a solution of 530 mg of cyclohexanol in 5 cm$^3$ of tetrahydrofuran at 0° C. under argon. After stirring for 15 min, 500 mg of 3,6-dichloro[1,2,4]triazolo[4,3-b]pyridazine (commercial) are added. The brown suspension is stirred, allowing the temperature to return gradually to 20° C. for 24 h. The reaction medium is poured into water and the mixture is extracted with ethyl acetate. After concentration to dryness under vacuum, a brown powder is obtained, which is washed with ether. The filtrate is concentrated to dryness and the oily yellow residue is chromatographed on Biotage Quad 12/25 (KP-SIL, 60 A; 32-63 µm), elution being carried out with a gradient of 100% dichloromethane to 95:5 dichloromethane/methanol. 184 mg of 3-chloro-6-(cyclohexyloxy)[1,2,4]triazolo[4,3-b]pyridazine are thus obtained in the form of a white powder, the characteristics of which are as follows:
MASS SPECTRUM: LC/MS Electrospray on WATERS UPLC-SQD: MH+=253+
$^1$H NMR SPECTRUM (400 MHz, d6-DMSO) δ ppm: 0.84-1.01 (m, 4 H) 1.98 (m, 1 H) 7.43 (tdd, J=8.5, 2.6, 1.0 Hz, 1 H) 7.51-7.65 (m, 2 H) 7.70 (d, J=8.5 Hz, 1 H) 7.77 (ddd, J=10.4, 2.6, 1.7 Hz, 1 H) 7.88 (ddd, J=7.8, 1.7, 1.0 Hz, 1 H) 8.05 (d, J=9.8 Hz, 1 H) 8.22 (broad d, J=2.0 Hz, 1 H) 8.54 (d, J=9.8 Hz, 1 H) 12.68 (broad m, 1 H)

EXAMPLE 64

1-(6-{[6-(3-Fluorophenyl)[1,2,4]triazolo[4,3-b]pyridazin-3-yl]sulphanyl}-1,3-benzothiazol-2-yl)-3-[2-(morpholin-4-yl)ethyl]urea The 1-(6-{[6-(3-fluorophenyl)[1,2,4]triazolo[4,3-b]pyridazin-3-yl]sulphanyl}-1,3-benzothiazol-2-yl)-3-[2-(morpholin-4-yl)ethyl]urea can be prepared according to the method described in Example 16a, but using 670 mg of 3-chloro-6-(3-fluorophenyl)[1,2,4]triazolo[4,3-b]pyridazine, 13.4 cm$^3$ of degassed ethanol, 127 mg of sodium borohydride and 1.14 g of 1-[2-(morpholin-4-yl)ethyl]-3-(6-sulphanyl-1,3-benzothiazol-2-yl)urea. 135 mg of 1-(6-{[6-(3-fluorophenyl)-[1,2,4]triazolo[4,3-b]pyridazin-3-yl]sulphanyl}-1,3-benzothiazol-2-yl)-3-[2-(morpholin-4-yl)ethyl]urea are thus obtained in the form of a beige powder, the characteristics of which are as follows:
MELTING POINT: 251° C. (Büchi B-545)
MASS SPECTRUM: LC/MS Electrospray on WATERS UPLC-SQD: MH+=551+; MH−=549−
$^1$H NMR SPECTRUM (300 MHz, d6-DMSO) δ ppm: 2.37-2.45 (m, 6 H) 3.23-3.29 (m, partially masked, 2 H) 3.59 (m, 4 H) 6.79 (broad m, 1 H) 7.44 (m, 1 H) 7.51 (dd, J=8.5, 2.0 Hz, 1 H) 7.56-7.66 (m, 2 H) 7.79 (dm, J=10.4 Hz, 1 H) 7.89 (dm, J=8.0 Hz, 1 H) 8.05 (d, J=9.9 Hz, 1 H) 8.16 (d, J=2.0 Hz, 1 H) 8.53 (d, J=9.9 Hz, 1 H) 10.96 (broad m, 1 H)

EXAMPLE 65

N-(6-{[6-(3-Fluorophenyl)[1,2,4]triazolo[4,3-b]pyridazin-3-yl]sulphanyl}-1,3-benzothiazol-2-yl)acetamide The N-(6-{[6-(3-fluorophenyl)[1,2,4]triazolo[4,3-b]pyridazin-3-yl]sulphanyl}-1, benzothiazol-2-yl)acetamide can be prepared according to the method described in Example 18b, but using 100 mg of 6-{[6-(3-fluorophenyl)[1,2,4]triazolo[4,3-b]pyridazin-3-yl]sulphanyl}-1,3-benzothiazol-2-amine in 5 cm$^3$ of pyridine and 0.318 cm$^3$ of acetic anhydride at 50° C. for 4 h. 54 mg of N-(6-{[6-(3-fluorophenyl)[1,2,4]triazolo[4,3-b]pyridazin-3-yl]sulphanyl}-1,3-benzothiazol-2-yl)acetamide are thus obtained in the form of a white powder, the characteristics of which are as follows:
MELTING POINT>255° C. (Büchi B-545)
MASS SPECTRUM: LC/MS Electrospray on WATERS UPLC-SQD: MH+=437+; MH−=435−
$^1$H NMR SPECTRUM (300 MHz, d6-DMSO) δ ppm: 2.18 (s, 3 H) 7.43 (m, 1 H) 7.52-7.65 (m, 2 H) 7.70 (d, J=8.5 Hz, 1 H) 7.77 (ddd, J=10.3, 2.7, 1.6 Hz, 1 H) 7.88 (m, 1 H) 8.05 (d, J=9.8, Hz, 1 H) 8.23 (broad d, J=2.0 Hz, 1 H) 8.54 (d, J=9.8 Hz, 1 H) 12.38 (broad m, 1 H)

EXAMPLE 66

N-(6-{[6-(4-Fluorophenyl)[1,2,4]triazolo[4,3-b]pyridazin-3-yl]sulphanyl}-1,3-benzothiazol-2-yl)-2-methylpropanamide a) The N-(6-{[6-(4-fluorophenyl)[1,2,4]triazolo[4,3-b]pyridazin-3-yl]sulphanyl}-1,3-benzothiazol-2-yl)-2-methylpropanamide can be prepared in a manner similar to the method described in Example 18b, but using 560 mg of 6-{[6-(4-fluorophenyl)[1,2,4]triazolo[4,3-b]pyridazin-3-yl]sulphanyl}-1,3-benzothiazol-2-amine and 0.212 cm$^3$ of 2-methylpropanoyl chloride in 3 cm$^3$ of pyridine after 24 h at 20° C. Next, water is added and the mixture is stirred for 5 min, then the precipitate is spin-filter-dried, washed with water and dried under vacuum. After purification on silica, 305 mg of N-(6-{[6-(4-fluorophenyl)[1,2,4]triazolo[4,3-b]pyridazin-3-yl]sulphanyl}-1,3-benzothiazol-2-yl)-2-methylpropanamide are thus obtained in the form of a pale yellow solid, the characteristics of which are as follows:
MELTING POINT>255° C. (Büchi B-545)
MASS SPECTRUM: LC/MS Electrospray on WATERS UPLC-SQD: MH+=465; MH−=463−
$^1$H NMR SPECTRUM (400 MHz, d6-DMSO) δ ppm: 1.14 (d, J=6.8 Hz, 6 H) 2.77 (m, 1 H) 7.40 (t, J=9.0 Hz, 2 H) 7.57 (dd, J=8.6, 2.0, Hz, 1 H) 7.71 (d, J=8.6, Hz, 1 H) 8.03 (d, J=9.8 Hz, 1 H) 8.10 (dd, J=9.0, 5.4 Hz, 2 H) 8.23 (d, J=2.0 Hz, 1 H) 8.52 (d, J=9.8 Hz, 1 H) 12.24 (broad s, 1 H)

EXAMPLE 67

N-(6-{[6-(3-Fluorophenyl)[1,2,4]triazolo[4,3-b]pyridazin-3-yl]sulphanyl}-1,3-benzothiazol-2-yl)cyclopropanecarboxamide a) The N-(6-{[6-(3-fluorophenyl)[1,2,4]triazolo[4,3-b]pyridazin-3-yl]sulphanyl}-1,3-benzothiazol-2-yl)cyclopropanecarboxamide can be prepared in a manner similar to the method described in Example 18b, but using 100 mg of 6-{[6-(3-fluorophenyl)[1,2,4]triazolo[4,3-b]pyridazin-3-yl]sulphanyl}-1,3-benzothiazol-2-amine in 1 cm$^3$ of pyridine with 0.028 cm$^3$ of cyclopropanecarboxylic acid chloride. After reaction for 3 h at 20° C., water is added and the precipitate is spin-filter-dried, and washed with water and with ether. After chromatography of the precipitate on a Biotage silica cartridge, 51 mg of N-(6-{[6-(3-fluorophenyl)[1,2,4]triazolo[4,3-b]pyridazin-3-yl]sulphanyl}-1,3-benzothiazol-2-yl)cyclopropanecarboxamide are obtained in the form of a white powder, the characteristics of which are as follows:
MELTING POINT: >255° C. (Büchi B-545)
MASS SPECTRUM: LC/MS Electrospray on WATERS UPLC-SQD: MH+=463+; MH−=461−

$^1$H NMR SPECTRUM (300 MHz, d6-DMSO) δ ppm: 0.84-1.01 (m, 4 H) 1.98 (m, 1 H) 7.43 (tdd, J=8.5, 2.6, 1.0 Hz, 1 H) 7.51-7.65 (m, 2 H) 7.70 (d, J=8.5 Hz, 1 H) 7.77 (ddd, J=10.4, 2.6, 1.7 Hz, 1 H) 7.88 (ddd, J=7.8, 1.7, 1.0 Hz, 1 H) 8.05 (d, J=9.8 Hz, 1 H) 8.22 (broad d, J=2.0 Hz, 1 H) 8.54 (d, J=9.8 Hz, 1 H) 12.68 (broad m, 1 H)

EXAMPLE 68

6-{[6-(4-Fluorophenyl)-7,8-dihydro[1,2,4]triazolo[4,3-b]pyridazin-3-yl]sulphanyl}-N-(2-methylbutyl)-1,3-benzothiazol-2-amine a) The 6-{[6-(4-fluorophenyl)-7,8-dihydro[1,2,4]triazolo[4,3-b]pyridazin-3-yl]sulphanyl}-N-(2-methylbutyl)-1,3-benzothiazol-2-amine can be prepared in the following way:
0.366 cm$^3$ of 2-methylbutylamine is added to a solution of 280 mg of 2-bromo-1,3-benzothiazol-6-yl thiocyanate in 7 cm$^3$ of tetrahydrofuran. The reaction medium is stirred for 2 h at 20° C., and then the suspension is concentrated to dryness under vacuum. This yellowy-beige resinous residue is taken up in 6 cm$^3$ of EtOH. The yellow suspension is degassed with argon for 10 min at 20° C. and then 5 mg of potassium dihydrogen phosphate in 0.6 cm$^3$ of water are added, followed by 467 mg of DL-dithiothreitol. The reaction medium is brought to reflux for 2 h and then 269 mg of chlorinated derivative are added. After refluxing for 18 h, the mixture is concentrated to dryness under vacuum.
The resinous residue is purified by dry deposit on Biotage Quad 25M (KP-SIL, 60 Å; 32-63 μm), elution being carried out with a gradient of 95:5 to 50:50 of dichloromethane/(dichloromethane:38/methanol:17/aqueous ammonia:2). The pale yellow powder obtained is made into a paste in MeOH and the solid is spin-filter-dried and washed with methanol. 58 mg of 6-{[6-(4-fluorophenyl)-7,8-dihydro[1,2,4]triazolo[4,3-b]pyridazin-3-yl]sulphanyl}-N-(2-methylbutyl)-1,3-benzothiazol-2-amine are thus obtained in the form of a beige powder, the characteristics of which are as follows:
MELTING POINT Mp=220° C. (Köfler block)
MASS SPECTRUM: LC/MS Electrospray on WATERS UPLC-SQD: MH+=467+; [M+2H]2+=234+; MH−=465−
$^1$H NMR SPECTRUM (400 MHz, d6-DMSO) δ ppm: 0.83-0.92 (m, 5 H) 1.15 (m, 1 H) 1.43 (m, 1 H) 1.68 (m, 1 H) 3.16 (s, 4 H) 3.19 (m, 1 H) 3.27 (m, partially masked, 2 H) 7.29-7.42 (m, 4 H) 7.91-7.99 (m, 3 H) 8.17 (broad t, J=6.2 Hz, 1 H)

b) The 3-chloro-6-(4-fluorophenyl)-7,8-dihydro[1,2,4]triazolo[4,3-b]pyridazine can be prepared in the following way:
790 mg of zinc powder are added to a mixture of 300 mg of 3-chloro-6-(4-fluorophenyl)[1,2,4]triazolo[4,3-b]pyridazine in 10 cm$^3$ of glacial acetic acid at 20° C. After stirring for 1 h, the suspension is filtered and the filtrate is concentrated to dryness under vacuum. The oily residue is purified by dry deposit on Biotage Quad 12M (KP-SIL, 60 Å; 32-63 μm), elution being carried out with a 95:5 mixture of dichloromethane/methanol. 263 mg of 3-chloro-6-(4-fluorophenyl)-7,8-dihydro[1,2,4]triazolo[4,3-b]pyridazine are thus obtained in the form of a yellowy-brown powder, the characteristics of which are as follows:
MASS SPECTRUM: LC/MS Electrospray on WATERS UPLC-SQD: MH+=251+
$^1$H NMR SPECTRUM (400 MHz, d6-DMSO) δ ppm: 3.15-3.27 (m, 4 H) 7.39 (t, J=8.8 Hz, 2 H) 8.04 (dd, J=9.0, 5.4 Hz, 2 H)

EXAMPLE 69

Pharmaceutical Composition

Tablets corresponding to the following formula were prepared:

| Product of Example 1 | 0.2 g |
|---|---|
| Excipient for a finished tablet weighing | 1 g |

(excipient details: lactose, talc, starch, magnesium stearate).

EXAMPLE 70

Pharmaceutical Composition

Tablets corresponding to the following formula were prepared:

| Product of Example 4 | 0.2 g |
|---|---|
| Excipient for a finished tablet weighing | 1 g |

(excipient details: lactose, talc, starch, magnesium stearate).

Examples 1 and 4 are taken as examples of a pharmaceutical preparation, it being possible for this preparation to be carried out, if desired, with other products in the examples in the present invention.

Pharmacological Section:
Experimental Protocols

I) Expression and Purification of MET, Cytoplasmic Domain Expression in Baculovirus:

The His-Tev-MET (956-1390) recombinant DNA in pFast-Bac (Invitrogen) is transfected into insect cells, and after several viral amplification steps, the final baculovirus stock is tested for the expression of the protein of interest.

After infection for 72 h at 27° C. with the recombinant virus, the SF21 cell cultures are harvested by centrifugation and the cell pellets are stored at −80° C.

Purification:

The cell pellets are resuspended in lysis buffer (buffer A [50 mM HEPES, pH 7.5, 250 mM NaCl, 10% glycerol, 1 mM TECP]; +cocktail of protease inhibitors, Roche Diagnostics, without EDTA, ref 1873580), stirred at 4° C. until the mixture is homogeneous and then lyzed mechanically using a "Dounce" type apparatus.

After centrifugation, the lysis supernatant is incubated for 2 h at 4° C. with nickel chelate resin (His-Trap 6 Fast Flow™, GE HealthCare). After washing with 20 volumes of buffer A, the suspension is packed into a column, and the proteins are eluted with a gradient of buffer B (TpA+290 mM imidazole).

The fractions containing the protein of interest for the purpose of electrophoretic analysis (SDS PAGE) are combined, concentrated by ultrafiltration (10 kDa cut-off) and injected onto an exclusion chromatography column (Superdex™ 200, GE HealthCare) equilibrated in buffer A.

After enzymatic cleavage of the histidine tag, the protein is reinjected onto a new IMAC nickel chelate chromatography column (His-Trap 6 Fast Flow™, GE HealthCare) equilibrated in buffer A. The fractions eluted with a gradient of buffer B and containing the protein of interest after electrophoresis (SDS PAGE) are finally combined and conserved at −80° C.

For the production of autophosphorylated protein, the previous fractions are incubated for 1 h at ambient temperature after the addition of 2 mM ATP, 2 mM $MgCl_2$, and 4 mM $Na_3VO_4$. After the reaction has been stopped with 5 mM of EDTA, the reaction mixture is injected onto a HiPrep desalifying column (GE HealthCare) preequilibrated in buffer A+4 mM $Na_3VO_4$, and the fractions containing the protein of interest (SDS PAGE analysis) are combined and stored at −80° C. The degree of phosphorylation is verified by mass spectrometry (LC-MS) and by peptide mapping.

II) Tests A and B

A) Test A: HTRF MET assay in 96-well format

MET at a final concentration of 5 nM is incubated in a final volume of 50 µl of enzymatic reaction in the presence of the test molecule (for a final concentration range of from 0.17 nM to 10 µM, 3% DMSO final concentration) in 10 mM MOPS buffer, pH 7.4, 1 mM DTT, 0.01% Tween 20. The reaction is initiated with the substrate solution to obtain final concentrations of 1 µg/ml poly-(GAT), 10 µM ATP and 5 mM $MgCl_2$. After incubation for 10 min at ambient temperature, the reaction is stopped with a 30 µl mix so as to obtain a final solution of 50 mM Hepes pH 7.5, 500 mM potassium fluoride, 0.1% BSA and 133 mM EDTA in the presence of 80 ng of streptavidin 61SAXLB Cis-Bio Int. and 18 ng of anti-phosphotyrosine Mab PT66-Europium Cryptate per well. After incubation for 2 hours at ambient temperature, the reading is taken at 2 wavelengths, 620 nm and 665 nm, on a reader for the TRACE/HTRF technique and the % inhibition is calculated from the 665/620 ratios.

The results obtained with this test A for the products of formula (I) in examples in the experimental section are such that IC50 is less than 500 nM, and in particular less than 100 nM.

B) Test B: Inhibition of the autophosphorylation of MET; ELISA technique (pppY1230,1234,1235)

a) Cell lysates: Seed MKN45 cells into 96-well plates (Cell coat BD polylysine) at 20 000 cells/well in 200 µl in RPMI medium+10% FCS+1% L-glutamine. Leave to adhere for 24 hours in an incubator.

The cells are treated the day after seeding with the products at 6 concentrations in duplicate for 1 h. At least 3 control wells are treated with the same final amount of DMSO.

Product dilution: Stock at 10 mM in pure DMSO—range from 10 mM to 30 µM with an increment of 3 in pure DMSO—intermediate 1/50 dilutions in culture medium and then removal of 10 µl added directly to the cells (200 µl): final range of 10 000 to 30 nM.

At the end of the incubation, carefully remove the supernatant and rinse with 200 µl of PBS. Next, place 100 µl of lysis buffer directly in the wells on ice and incubate at 4° C. for 30 minutes. Lysis buffer: 10 mM Tris HCl, pH7.4, 100 mM NaCl, 1 mM EDTA, 1 mM EGTA, 1% Triton X-100, 10% glycerol, 0.1% SDS, 0.5% deoxycholate, 20 mM NaF, 2 mM $Na_3VO_4$, 1 mM PMSF and cocktail of antiproteases.

The 100 µl of lysates are transferred into a V-bottomed polypropylene plate and the ELISA is performed immediately, or the plate is frozen at −80° C.

b) PhosphoMET ELISA BioSource Kit KH00281

Into each well of the kit plate, add 70 µl of kit dilution buffer+30 µL of cell lysate or 30 µl of lysis buffer for the blanks. Incubate for 2 h with gentle agitation at ambient temperature.

Rinse the wells 4 times with 400 µl of kit washing buffer. Incubate with 100 µl of anti-phospho MET antibody for 1 hour at ambient temperature.

Rinse the wells 4 times with 400 µl of kit washing buffer. Incubate with 100 µl of anti-rabbit HRP antibody for 30 minutes at ambient temperature (except for the wells of chromogen alone).

Rinse the wells 4 times with 400 μl of kit washing buffer. Introduce 100 μL of chromogen and incubate for 30 minutes in the dark at ambient temperature.

Stop the reaction with 100 μl of stop solution. Read without delay at 450 nM, 0.1 second on Wallac Victor plate reader.

C) Test C: Measurement of cell proliferation by $^{14}$c-thymidine pulse

The cells are seeded into Cytostar 96-well plates in 180 μl for 4 hours at 37° C. and 5% $CO_2$: HCT116 cells at a rate of 2500 cells per well in DMEM medium+10% foetal calf serum+1% L-glutamine and MKN45 cells at a rate of 7500 cells per well in RPMI medium+10% foetal calf serum+1% L-glutamine. After these 4 hours of incubation, the products are added in 10 μl as a 20-fold concentrated solution according to the dilution method mentioned for the ELISA. The products are tested at 10 concentrations in duplicate from 10 000 nM to 0.3 nM with an increment of 3.

After treatment for 72 h, add 10 μl of $^{14}$C-thymidine at 10 μCi/ml to obtain 0.1 μCi per well. The $^{14}$C-thymidine incorporation is measured on a Micro-Beta machine (Perkin-Elmer) after 24 hours of pulse and 96 h of treatment.

All the steps of the assay are automated on BIOMEK 2000 or TECAN stations.

The results obtained with this test B for the products of formula (I) as examples in the experimental section are such that $IC_{50}$ is less than 10 microM and in particular less than 1 microM.

The results obtained for the products as examples in the experimental section are given in the table of pharmacological results below, as follows:

for test A, the sign + corresponds to less than 500 nM and the sign ++ corresponds to less than 100 nM;
for test B, the sign + corresponds to less than 500 nM and the sign ++ corresponds to less than 100 nM;
for test C, the sign + corresponds to less than 10 microM and the sign ++ corresponds to less than 1 microM.

Table of pharmacological results:

| Example number | test A | test B | test C |
|---|---|---|---|
| 1 | ++ | ++ | ++ |
| 2 | ++ | + | ++ |
| 3 | ++ | ++ | ++ |
| 4 | ++ | ++ | ++ |
| 5 | ++ | + | ++ |
| 6 | ++ | ++ | ++ |
| 7 | ++ | + | ++ |
| 8 | ++ | − | + |
| 9 | ++ | ++ | ++ |
| 10 | ++ | ++ | ++ |
| 11 | ++ | ++ | ++ |
| 12 | ++ | ++ | ++ |
| 13 | ++ | ++ | ++ |
| 14 | ++ | ++ | ++ |
| 15 | ++ | ++ | ++ |
| 16 | ++ | ++ | ++ |
| 17 | ++ | ++ | ++ |
| 18 | ++ | + | ++ |
| 19 | ++ | ++ | ++ |
| 20 | ++ | ++ | ++ |
| 21 | ++ | + | ++ |
| 22 | ++ | + | ++ |
| 23 | ++ | ++ | ++ |
| 24 | ++ | ++ | ++ |
| 25 | ++ | + | ++ |
| 26 | ++ | ++ | ++ |
| 27 | ++ | ++ | ++ |
| 28 | ++ | ++ | ++ |
| 29 | ++ | + | ++ |
| 30 | ++ | ++ | ++ |
| 31 | ++ | + | ++ |
| 32 | ++ | ++ | ++ |
| 33 | + | ++ | ++ |
| 34 | ++ | ++ | + |
| 35 | ++ | ++ | ++ |
| 36 | ++ | ++ | ++ |
| 37 | ++ | ++ | ++ |
| 38 | ++ | ++ | ++ |
| 39 | ++ | ++ | ++ |
| 40 | ++ | ++ | ++ |
| 41 | ++ | ++ | ++ |
| 42 | ++ | ++ | ++ |
| 43 | ++ | ++ | ++ |
| 44 | ++ | ++ | ++ |
| 45 | ++ | + | ++ |
| 46 | ++ | + | ++ |
| 47 | ++ | + | ++ |
| 48 | ++ | + | ++ |
| 49 | ++ | ++ | ++ |
| 50 | ++ | + | ++ |
| 51 | ++ | ++ | ++ |
| 52 | ++ | ++ | ++ |
| 53 | ++ | ++ | ++ |
| 54 | ++ | + | ++ |
| 55 | ++ | + | ++ |
| 56 | ++ | + | ++ |
| 57 | ++ | + | ++ |
| 58 | ++ | ++ | ++ |
| 59 | ++ | ++ | ++ |
| 60 | ++ | ++ | ++ |
| 61 | ++ | ++ | ++ |
| 62 | ++ | ++ | ++ |
| 63 | ++ | + | ++ |
| 64 | ++ | ++ | ++ |
| 65 | ++ | ++ | ++ |
| 66 | ++ | + | ++ |
| 67 | ++ | ++ | ++ |
| 68 | + | − | + |

What is claimed is:

1. A method of treating cancer by inhibiting MET protein kinase, the method comprising administering to a patient in need thereof an effective amount of a compound of formula (I):

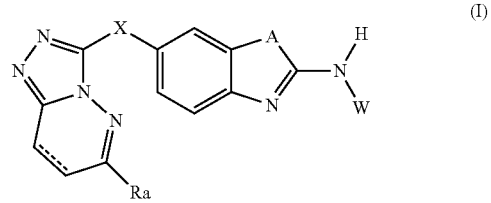

wherein:

---- represents a single or double bond;

Ra represents a hydrogen atom; a halogen atom; an alkoxy radical optionally substituted with a chlorine atom, a hydroxyl radical or a heterocycloalkyl radical; an O-cycloalkyl radical; heteroaryl radical; a phenyl radical; an NHCOalk or NHCOcycloalk radical; or an NR1R2 radical;

X represents S, SO or $SO_2$;

A represents NH or S;

W represents a hydrogen atom; an alkyl radical optionally substituted with alkoxy, heterocycloalkyl or NR3R4; or a COR radical in which R represents:

a cycloalkyl radical or an alkyl radical optionally substituted with an NR3R4, alkoxy, hydroxyl, phenyl, heteroaryl or heterocycloalkyl radical;

an alkoxy radical optionally substituted with NR3R4, alkoxy, hydroxyl or with heterocycloalkyl; an O-phenyl radical or an O—(CH$_2$)$_n$-phenyl radical, and n representing an integer from 1 to 4;

or an NR1R2 radical; R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical containing from 3 to 10 members and optionally one or more other heteroatoms chosen from O, S, N and NH;

R3 and R4, which may be identical or different, represent a hydrogen atom or an alkyl radical, a cycloalkyl radical, a heteroaryl radical or a phenyl radical that is optionally substituted, or else R3 and R4 form, with the nitrogen atom to which they are attached, a cyclic radical containing from 3 to 10 members and optionally one or more other heteroatoms chosen from O, S, N and NH;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, NH$_2$, NHalk and N(alk)$_2$ radicals, alkyl, cycloalkyl, heterocycloalkyl, CH$_2$-heterocycloalkyl, phenyl, CH$_2$-phenyl, heteroaryl, CO-phenyl and S-heteroaryl radicals; wherein the alkyl, heterocycloalkyl, phenyl and heteroaryl radicals being themselves optionally substituted with one or more radicals chosen from halogen atoms and the radicals: hydroxyl, oxo, alkyl and alkoxy containing from 1 to 4 carbon atoms, NH$_2$, NHalk and N(alk)$_2$;

wherein the term alkyl means a $C_1$ to $C_6$ alkyl group; the term alkoxy means a $C_1$ to $C_6$ alkoxy group; the term cycloalkyl means a saturated carbocyclic radical containing 3 to 10 carbon atoms; the term heterocycloalkyl means a mono or bicyclic carbocyclic radical containing from 3 to 10 members, interrupted with one or more heteroatoms, which may be the same or different chosen from oxygen, nitrogen or sulphur atoms; and the term heteroaryl means a monocyclic or bicyclic unsaturated or partially unsaturated heterocyclic radical containing at most 12 members, which may optionally contain a —C(O)— member and containing one or more heteroatoms which may be the same or different chosen from oxygen, nitrogen or sulphur atoms;

or the addition salts with pharmaceutically acceptable mineral and organic acids or with pharmaceutically acceptable mineral and organic bases of said compounds, wherein the cancer is selected from gastric cancer, renal cancer, lung cancer, and melanoma.

2. The method according to claim 1, wherein $\overline{\phantom{--}}$, X and A are as defined in claim 1;

Ra represents an alkoxy radical optionally substituted with a chlorine atom, a hydroxyl radical or a heterocycloalkyl radical; an O-cycloalkyl radical; an NHCOalk; or an NR1R2 radical;

and W represents a hydrogen atom; an alkyl radical optionally substituted with alkoxy, heterocycloalkyl or NR3R4; or a COR radical in which R represents:

a cycloalkyl radical or an alkyl radical optionally substituted with an NR3R4, alkoxy, hydroxyl, phenyl, heteroaryl or heterocycloalkyl radical;

an alkoxy radical optionally substituted with NR3R4, alkoxy, hydroxyl or with heterocycloalkyl; an O-phenyl radical or an O—(CH$_2$)$_n$-phenyl radical and n representing an integer from 1 to 4;

or an NR1R2 radical in which R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and phenyl radicals, or else R1 and R2 form, with the nitrogen atom to which they are attached, a cyclic radical containing from 3 to 10 members and optionally one or more other heteroatoms chosen from O, S, N and NH;

R3 and R4, which may be identical or different, represent a hydrogen atom or an alkyl radical, a cycloalkyl radical, a heteroaryl radical or a phenyl radical, or else R3 and R4 form, with the nitrogen atom to which they are attached, a cyclic radical containing from 3 to 10 members and optionally one or more other heteroatoms chosen from O, S, N and NH;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, NH$_2$, NHalk and N(alk)$_2$ radicals, cycloalkyl, CH$_2$-heterocycloalkyl, CH$_2$-phenyl, CO-phenyl, S-heteroaryl radicals, alkyl, heterocycloalkyl, phenyl, and heteroaryl which alkyl, heterocycloalkyl, phenyl and heteroaryl radicals are themselves optionally substituted with one or more radicals chosen from halogen atoms and the radicals: hydroxyl, oxo, alkyl and alkoxy containing from 1 to 4 carbon atoms, NH$_2$, NHalk and N(alk)$_2$;

or the addition salts with pharmaceutically acceptable mineral and organic acids or with pharmaceutically acceptable mineral and organic bases of said compounds.

3. The method according to claim 1, wherein $\overline{\phantom{--}}$, Ra and X are as defined in claim 1, and:

A represents NH or S;

W represents a hydrogen atom; an alkyl radical optionally substituted with alkoxy or heterocycloalkyl; or a COR radical in which R represents:

a cycloalkyl radical or an alkyl radical optionally substituted with an NR3R4, alkoxy, hydroxyl, phenyl, heteroaryl or heterocycloalkyl radical;

an alkoxy radical optionally substituted with NR3R4, alkoxy, hydroxyl or with heterocycloalkyl; an O-phenyl radical or an O—(CH$_2$)$_n$-phenyl radical and n representing an integer from 1 to 4;

or an NR1R2 radical, in which R1 and R2 are such that one of R1 and R2 represents a hydrogen atom or an alkyl radical and the other of R1 and R2 represents a hydrogen atom, a cycloalkyl radical or an alkyl radical optionally substituted with NR3R4 or with alkoxy, or else R1 and R2 form, with the nitrogen atom to which they are attached, a cyclic radical containing from 3 to 10 members and optionally one or more other heteroatoms chosen from O, S, N and NH;

R3 and R4, which may be identical or different, represent a hydrogen atom or an alkyl radical, or else R3 and R4 form, with the nitrogen atom to which they are attached, a cyclic radical containing from 3 to 10 members and optionally one or more other heteroatoms chosen from O, S, N and NH;

the heterocycloalkyl, heteroaryl and phenyl radicals and also the cyclic radicals that R1 and R2 or R3 and R4 can form with the nitrogen atom to which they are attached, defined above, being optionally substituted with one or more radicals chosen from halogen atoms, hydroxyl, alkoxy, $NH_2$, NHalk and $N(alk)_2$ radicals, alkyl, heterocycloalkyl, $CH_2$-heterocycloalkyl, phenyl, $CH_2$-phenyl, heteroaryl, CO-phenyl and S-heteroaryl radicals; wherein the alkyl, heterocycloalkyl, phenyl and heteroaryl radicals being themselves optionally substituted with one or more radicals chosen from halogen atoms and the radicals: hydroxyl, alkyl and alkoxy containing from 1 to 4 carbon atoms, $NH_2$, NHalk and $N(alk)_2$;

or the addition salts with pharmaceutically acceptable mineral and organic acids or with pharmaceutically acceptable mineral and organic bases of said compounds.

4. The method according to claim 1, wherein:

---- represents a single or double bond;

Ra represents a hydrogen atom a halogen atom or a phenyl radical;

X represents S, SO or $SO_2$;

A represents NH or S;

W represents a hydrogen atom or a COR radical in which R represents:

a cycloalkyl radical or an alkyl radical optionally substituted with a phenyl, heteroaryl, NR3R4 or heterocycloalkyl radical;

an alkoxy radical optionally substituted with NR3R4 of the formula O—$(CH_2)_n$—NR3R4, an O-phenyl radical or; an O—$(CH_2)_n$-phenyl radical and n representing an integer from 1 to 4;

or an NR1R2 radical in which R1 and R2 are such that one of R1 and R2 represents a hydrogen atom or an alkyl radical and the other of R1 and R2 represents a cycloalkyl radical or an alkyl radical optionally substituted with one or more radicals, which may be identical or different, chosen from hydroxyl, alkoxy, heteroaryl, heterocycloalkyl, NR3R4 and phenyl radicals, or else R1 and R2 form, with the nitrogen atom to which they are attached, a cyclic radical containing from 3 to 10 members and optionally containing one or more other heteroatoms chosen from O, S, N and NH;

R3 and R4, which may be identical or different, represent a hydrogen atom or an alkyl radical, a cycloalkyl radical, a heteroaryl radical or an optionally substituted phenyl radical, or else R3 and R4 form, with the nitrogen atom to which they are attached, a cyclic radical containing from 3 to 10 members and optionally containing one or more other heteroatoms chosen from O, S, N and NH;

all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, $NH_2$, NHalk, $N(alk)_2$ radicals, alkyl, cycloalkyl, $CH_2$-heterocycloalkyl, $CH_2$-phenyl, CO-phenyl and S-heteroaryl radicals; wherein the alkyl, heterocycloalkyl, phenyl and heteroaryl radicals being themselves optionally substituted with one or more radicals chosen from halogen atoms and the radicals: hydroxyl, oxo, alkyl and alkoxy containing from 1 to 4 carbon atoms, $NH_2$, NHalk and $N(alk)_2$;

or the addition salts with pharmaceutically acceptable mineral and organic acids or with pharmaceutically acceptable mineral and organic bases of said compounds.

5. The method according to claim 1, wherein ----, Ra and X are as defined in claim 1, and:

A represents NH or S;

W represents a hydrogen atom or an alkyl radical or a COR radical in which R represents:

an alkyl radical optionally substituted with $OCH_3$ or NR3R4;

a cycloalkyl radical;

an O—$(CH_2)_n$—$OCH_3$ radical or an O—$(CH_2)_n$—NR3R4 radical, an O-phenyl radical or an O—$(CH_2)_n$-phenyl radical, with phenyl being optionally substituted and n representing an integer from 1 to 2;

or an NR1R2 radical, in which R1 and R2 are such that one of R1 and R2 represents a hydrogen atom, or an alkyl radical and the other of R1 and R2 represents an alkyl radical optionally substituted with NR3R4, or else R1 and R2 form with the nitrogen atom to which they are attached, a cyclic radical containing from 3 to 10 members and optionally containing one or more other heteroatoms chosen from O, S, N and NH;

R3 and R4, which may be identical or different, represent a hydrogen atom or an alkyl radical, or else R3 and R4 form, with the nitrogen atom to which they are attached, a cyclic radical containing from 3-10 members optionally containing one or more other heteroatoms chosen from O, S, N and NH;

the phenyl radicals and also the cyclic radicals that R1 and R2 or R3 and R4 can form with the nitrogen atom to which they are attached, defined above, being optionally substituted with one or more radicals chosen from halogen atoms, hydroxyl, alkoxy, $NH_2$, NHalk, $N(alk)_2$ radicals, alkyl, $CH_2$-heterocycloalkyl, $CH_2$-phenyl, CO-phenyl and S-heteroaryl radicals; wherein the alkyl, heterocycloalkyl, phenyl and heteroaryl radicals being themselves optionally substituted with one or more radicals chosen from halogen atoms and the radicals: hydroxyl, alkyl and alkoxy containing from 1 to 4 carbon atoms, $NH_2$, NHalk and $N(alk)_2$;

or the addition salts with pharmaceutically acceptable mineral and organic acids or with pharmaceutically acceptable mineral and organic bases of said compounds.

6. The method according to claim 1, wherein ----, Ra and X are as defined in claim 1, and:

A represents NH or S;

W represents a hydrogen atom or a COR radical in which R represents:

an alkyl radical optionally substituted with NR3R4;

an alkoxy radical optionally substituted with NR3R4 of the formula O—$(CH_2)_n$—NR3R4 radical, an O-phenyl radical or an O—$(CH_2)_n$-phenyl radical and n representing an integer from 1 to 2;

or an NR1R2 radical, in which R1 and R2 are such that one of R1 and R2 represents a hydrogen atom or an alkyl radical and the other of R1 and R2 represents an alkyl radical optionally substituted with NR3R4, or else R1 and R2 form, with the nitrogen atom to which they are attached, a cyclic radical containing from 3 to 10 members and optionally containing one or more other heteroatoms chosen from O, S, N and NH;

R3 and R4, which may be identical or different, represent a hydrogen atom or an alkyl radical, or else R3 and R4 form, with the nitrogen atom to which they are attached, a cyclic radical containing from 3 to 10 members and optionally containing one or more other heteroatoms chosen from O, S, N and NH;

the phenyl radicals and also the cyclic radicals that R1 and R2 or R3 and R4 can form with the nitrogen atom to which they are attached, defined above, being optionally substituted with one or more radicals chosen from halogen atoms, hydroxyl, alkoxy, NH$_2$, Nhalk, N(alk)$_2$ radicals, alkyl, CH$_2$-heterocycloalkyl, CH$_2$-phenyl, CO-phenyl and S-heteroaryl radicals; wherein the alkyl, heterocycloalkyl, phenyl and heteroaryl radicals being themselves optionally substituted with one or more radicals chosen from halogen atoms and the radicals: hydroxyl, alkyl and alkoxy containing from 1 to 4 carbon atoms, NH$_2$, NHalk and N(alk)$_2$;

or the addition salts with pharmaceutically acceptable mineral and organic acids or with pharmaceutically acceptable mineral and organic bases of said compounds.

7. The method according to claim 1, wherein ----, X, A and W are as defined in claim 1, Ra represents a hydrogen atom, a chlorine atom or the radical:

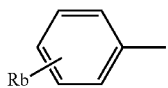

with Rb representing a halogen atom or an S-heteroaryl radical optionally substituted with a radical chosen from halogen atoms and the radicals: hydroxyl, alkyl and alkoxy containing from 1 to 4 carbon atoms, NH$_2$, NHalk and N(alk)$_2$, or the addition salts with pharmaceutically acceptable mineral and organic acids or with pharmaceutically acceptable mineral and organic bases of said compounds.

8. The method according to claim 1, wherein A represents NH, and ----, Ra, X and W are as defined in claim 1;

or the addition salts with pharmaceutically acceptable mineral and organic acids or with pharmaceutically acceptable mineral and organic bases of said compounds.

9. The method according to claim 1, wherein A represents S, and ----, Ra, X and W are as defined in claim 1;

or the addition salts with pharmaceutically acceptable mineral and organic acids or with pharmaceutically acceptable mineral and organic bases of said compounds.

10. The method according to claim 1, wherein the compound of formula (I) is selected from the group consisting of formula (Ia) and (Ib):

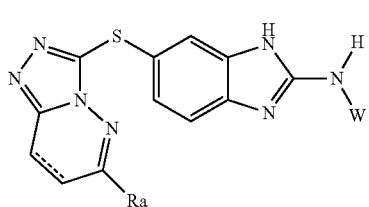

(Ia)

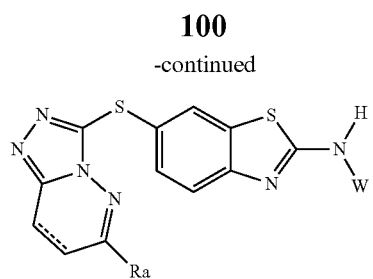

(Ib)

wherein ----, Ra and W are as defined in claim 1, or the addition salts with pharmaceutically acceptable mineral and organic acids or with pharmaceutically acceptable mineral and organic bases of said compound of formula (Ia) or (Ib).

11. The method according to claim 1 wherein the compound of formula (I) is a compound of formula (I'):

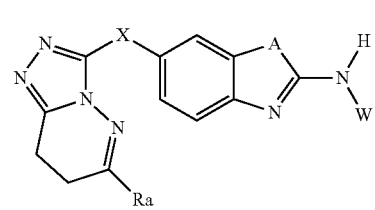

(I')

wherein the substituents Ra, X, A and W are as defined in claim 1, or the addition salts with pharmaceutically acceptable mineral and organic acids or with pharmaceutically acceptable mineral and organic bases of said compound of the formula (I').

12. The method according to claim 1 wherein the compound of formula (I) is a compound of formula (I"):

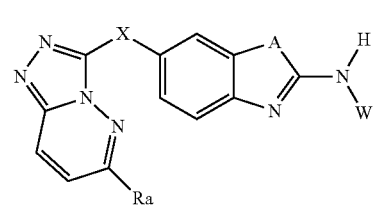

(I")

wherein the substituents Ra, X, A and W are as defined in claim 1, or the addition salts with pharmaceutically acceptable mineral and organic acids or with pharmaceutically acceptable mineral and organic bases of said compound of the formula (I").

13. The method according to claim 10 wherein the compound of formula (I) is a compound of formula (I'a):

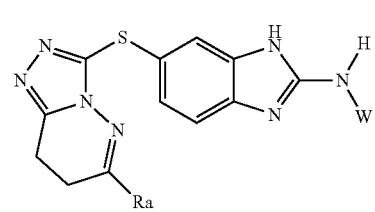

(I'a)

wherein Ra and W are as defined in claim 10,
or the addition salts with pharmaceutically acceptable mineral and organic acids or with pharmaceutically acceptable mineral and organic bases of said compound of the formula (I'a).

14. The method according to claim 10 wherein the compound of formula (I) is a compound of formula (I''a):

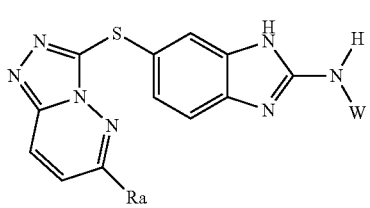

(I''a)

wherein Ra and W are as defined in claim 10,
or the addition salts with pharmaceutically acceptable mineral and organic acids or with pharmaceutically acceptable mineral and organic bases of said compound of the formula (I''a).

15. The method according to claim 10 wherein the compound of formula (I) is a compound of formula (I'b):

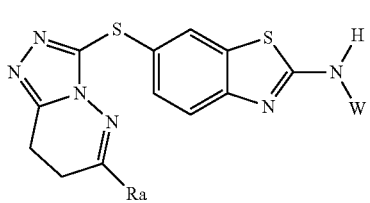

(I'b)

wherein Ra and W are as defined in claim 10,
or the addition salts with pharmaceutically acceptable mineral and organic acids or with pharmaceutically acceptable mineral and organic bases of said compound of the formula (I'b).

16. The method according to claim 10 wherein the compound of formula (I) is a compound of formula (I''b):

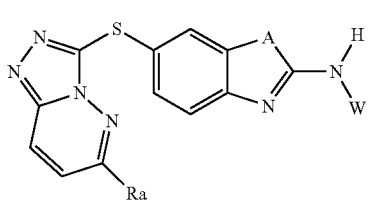

(I''b)

wherein Ra and W are as defined in claim 10,
or the addition salts with pharmaceutically acceptable mineral and organic acids or with pharmaceutically acceptable mineral and organic bases of said compound of the formula (I''b).

17. The method of claim 1 wherein the compound of formula (I) is selected from the group consisting of:

methyl (6-{[6-(4-fluorophenyl)[1,2,4]triazolo[4,3-b]pyridazin-3-yl]sulphanyl}-1,3-benzothiazol-2-yl)carbamate;

6-{[6-(4-fluorophenyl)[1,2,4]triazolo[4,3-b]pyridazin-3-yl]sulphanyl}-1,3-benzothiazol-2-amine;

methyl (6-{[6-(4-fluorophenyl)[1,2,4]triazolo[4,3-b]pyridazin-3-yl]sulphanyl}-1H-benzimidazol-2-yl)carbamate;

1-(6-{[6-(4-fluorophenyl)[1,2,4]triazolo[4,3-b]pyridazin-3-yl]sulphanyl}-1H-benzimidazol-2-yl)-3-(2-morpholin-4-ylethyl)urea;

6-{[6-(4-fluorophenyl)[1,2,4]triazolo[4,3-b]pyridazin-3-yl]sulphanyl}-1H-benzimidazol-2-amine;

1-(2-morpholin-4-ylethyl)-3-[6-([1,2,4]triazolo[4,3-b]pyridazin-3-ylsulphanyl)-1,3-benzothiazol-2-yl]urea;

1-(6-{[6-(4-fluorophenyl)[1,2,4]triazolo[4,3-b]pyridazin-3-yl]sulphanyl}-1,3-benzothiazol-2-yl)-3-(2-morpholin-4-ylethyl)urea;

1-{2-[(2R,6S)-2,6-dimethylmorpholin-4-yl]ethyl}-3-(6-{[6-(4-fluorophenyl)[1,2,4]triazolo[4,3-b]pyridazin-3-yl]sulphanyl}-1,3-benzothiazol-2-yl)urea;

(6-{[6-(4-fluorophenyl)[1,2,4]triazolo[4,3-b]pyridazin-3-yl]sulphanyl}-1,3-benzothiazol-2-yl)carbamate of 2-morpholin-4-ylethyl;

1-(6-{[6-(4-fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea;

N-(6-{[6-(4-fluorophenyl)[1,2,4]triazolo[4,3-b]pyridazin-3-yl]sulphanyl}-1,3-benzothiazol-2-yl)-4-morpholin-4-ylbutanamide;

1-[2-(diethylamino)ethyl]-3-(6-{[6-(4-fluorophenyl)[1,2,4]triazolo[4,3-b]pyridazin-3-yl]sulphanyl}-1,3-benzothiazol-2-yl)urea;

1-{6-[(6-methoxy[1,2,4]triazolo[4,3-b]pyridazin-3-yl)sulphanyl]-1,3-benzothiazol-2-yl}-3-[2-(morpholin-4-yl)ethyl]urea;

N-[6-({6-[(2-methoxyethyl)amino][1,2,4]triazolo[4,3-b]pyridazin-3-yl}sulphanyl)-1,3-benzothiazol-2-yl]acetamide;

6-{[6-(4-fluorophenyl)[1,2,4]triazolo[4,3-b]pyridazin-3-yl]sulphanyl}-N-[2-(morpholin-4-yl)ethyl]-1,3-benzothiazol-2-amine;

phenyl 6-{[6-(4-fluorophenyl)[1,2,4]triazolo[4,3-b]pyridazin-3-yl]sulphanyl}-1,3-benzothiazol-2-yl)carbamate;

1-{6-[(6-ethoxy[1,2,4]triazolo[4,3-b]pyridazin-3-yl)sulphanyl]-1,3-benzothiazol-2-yl}-3-[2-(morpholin-4-yl)ethyl]urea;

1-{6-[(6-ethoxy-7,8-dihydro[1,2,4]triazolo[4,3-b]pyridazin-3-yl)sulphanyl]-1,3-benzothiazol-2-yl}-3-[2-(morpholin-4-yl)ethyl]urea;

N-[6-({6-[(2-methoxyethyl)amino][1,2,4]triazolo[4,3-b]pyridazin-3-yl}sulphanyl)-1,3-benzothiazol-2-yl]cyclopropanecarboxamide;

1-(6-{[6-(4-fluorophenyl)[1,2,4]triazolo[4,3-b]pyridazin-3-yl]sulphanyl}-1,3-benzothiazol-2-yl)-3-[2-(4-oxidomorpholin-4-yl)ethyl]urea;

6-{[6-(1-methyl-1H-pyrazol-4-yl)[1,2,4]triazolo[4,3-b]pyridazin-3-yl]sulphanyl}-1,3-benzothiazol-2-amine;

1-(6-{[6-(4-fluorophenyl)-7,8-dihydro[1,2,4]triazolo[4,3-b]pyridazin-3-yl]sulphanyl}-1,3-benzothiazol-2-yl)-3-[2-(morpholin-4-yl)ethyl]urea;

oxetan-2-ylmethyl (6-{[6-(4-fluorophenyl)[1,2,4]triazolo[4,3-b]pyridazin-3-yl]sulphanyl}-1,3-benzothiazol-2-yl)carbamate;

N-{6-[(6-methoxy[1,2,4]triazolo[4,3-b]pyridazin-3-yl)sulphanyl]-1,3-benzothiazol-2-yl}cyclopropanecarboxamide;

N-(6-{[6-(4-fluorophenyl)[1,2,4]triazolo[4,3-b]pyridazin-3-yl]sulphanyl}-1,3-benzothiazol-2-yl)acetamide;

1-{6-[(6-methoxy[1,2,4]triazolo[4,3-b]pyridazin-3-yl)sulphanyl]-1,3-benzothiazol-2-yl}-3-[2-(pyrrolidin-1-yl)ethyl]urea;
6-[(6-ethoxy[1,2,4]triazolo[4,3-b]pyridazin-3-yl)sulphanyl]-1,3-benzothiazol-2-amine;
6-{[6-(3-fluorophenyl)[1,2,4]triazolo[4,3-b]pyridazin-3-yl]sulphanyl}-1,3-benzothiazol-2-amine;
1-cyclopropyl-3-{6-[(6-ethoxy[1,2,4]triazolo[4,3-b]pyridazin-3-yl)sulphanyl]-1,3-benzothiazol-2-yl}urea;
N-(6-{[6-(4-fluorophenyl)[1,2,4]triazolo[4,3-b]pyridazin-3-yl]sulphanyl}-1,3-benzothiazol-2-yl)cyclopropanecarboxamide;
N-(6-{[6-(4-fluorophenyl)-7,8-dihydro[1,2,4]triazolo[4,3-b]pyridazin-3-yl]sulphanyl}-1,3-benzothiazol-2-yl)cyclopropanecarboxamide;
1-(6-{[6-(3-fluorophenyl)[1,2,4]triazolo[4,3-b]pyridazin-3-yl]sulphanyl}-1,3-benzothiazol-2-yl)-3-[2-(morpholin-4-yl)ethyl]urea;
1,1-Dimethylethyl (6-{[6-(4-fluorophenyl)[1,2,4]triazolo[4,3-b]pyridazin-3-yl]sulphanyl}-1,3-benzothiazol-2-yl)carbamate;
Methyl (6-{[6-(4-fluorophenyl)-7,8-dihydro[1,2,4]triazolo[4,3-b]pyridazin-3-yl]sulphanyl}-1H-benzimidazol-2-yl)carbamate;
6-[(4-{3-[(2-amino-1,3-benzothiazol-6-yl)sulphanyl]-7,8-dihydro[1,2,4]triazolo[4,3-b]pyridazin-6-yl}phenyl)sulphanyl]-1,3-benzothiazol-2-amine;
1-(6-{[6-(4-Fluorophenyl)[1,2,4]triazolo[4,3-b]pyridazin-3-yl]sulphanyl}-1,3-benzothiazol-2-yl)-3-[2-(4-methylpiperazin-1-yl)ethyl]urea;
1,1-Dimethylethyl (6-{[6-(morpholin-4-yl)[1,2,4]triazolo[4,3-b]pyridazin-3-yl]sulphanyl}-1,3-benzothiazol-2-yl)carbamate;
N-(6-{[6-(Morpholin-4-yl)[1,2,4]triazolo[4,3-b]pyridazin-3-yl]sulphanyl}-1,3-benzothiazol-2-yl)acetamide;
1,1-Dimethylethyl (6-{[6-(4-methylpiperazin-1-yl)[1,2,4]triazolo[4,3-b]pyridazin-3-yl]sulphanyl}-1,3-benzothiazol-2-yl)carbamate hydrochloride;
1-(6-{[6-(1H-Imidazol-1-yl)[1,2,4]triazolo[4,3-b]pyridazin-3-yl]sulphanyl}-1,3-benzothiazol-2-yl)-3-[2-(morpholin-4-yl)ethyl]urea;
1,1-Dimethylethyl {6-[(6-methoxy[1,2,4]triazolo[4,3-b]pyridazin-3-yl)sulphanyl]-1,3-benzothiazol-2-yl}carbamate;
1,1-Dimethylethyl[6-({6-[(2-methoxyethyl)amino][1,2,4]triazolo[4,3-b]pyridazin-3-yl}sulphanyl)-1,3-benzothiazol-2-yl]carbamate;
N-(6-{[6-(4-Methylpiperazin-1-yl)[1,2,4]triazolo[4,3-b]pyridazin-3-yl]sulphanyl}-1,3-benzothiazol-2-yl)acetamide;
6-{[6-(4-Fluorophenyl)[1,2,4]triazolo[4,3-b]pyridazin-3-yl]sulphanyl}-N-(2-methoxyethyl)-1,3-benzothiazol-2-amine;
1-[2-(Morpholin-4-yl)ethyl]-3-(6-{[6-(morpholin-4-yl)[1,2,4]triazolo[4,3-b]pyridazin-3-yl]sulphanyl}-1,3-benzothiazol-2-yl)urea;
1-{6-[(6-Amino[1,2,4]triazolo[4,3-b]pyridazin-3-yl)sulphanyl]-1,3-benzothiazol-2-yl}-3-[2-(morpholin-4-yl)ethyl]urea;
N-(3-{[2-({[2-(Morpholin-4-yl)ethyl]carbamoyl}amino)-1,3-benzothiazol-6-yl]sulphanyl}[1,2,4]triazolo[4,3-b]pyridazin-6-yl)acetamide;
2,2-Dimethyl-N-(3-{[2-({[2-(morpholin-4-yl)ethyl]carbamoyl}amino)-1,3-benzothiazol-6-yl]sulphanyl}[1,2,4]triazolo[4,3-b]pyridazin-6-yl)propanamide;
1-[2-(Morpholin-4-yl)ethyl]-3-(6-{[6-(oxetan-2-ylmethoxy)[1,2,4]triazolo[4,3-b]pyridazin-3-yl]sulphanyl}-1,3-benzothiazol-2-yl)urea;
N-[6-({6-[(2-Methoxyethyl)amino][1,2,4]triazolo[4,3-b]pyridazin-3-yl}sulphanyl)-1,3-benzothiazol-2-yl]-4-(morpholin-4-yl)butanamide;
Ethyl {6-[(6-methoxy[1,2,4]triazolo[4,3-b]pyridazin-3-yl)sulphanyl]-1,3-benzothiazol-2-yl}carbamate;
3-Methoxypropyl {6-[(6-methoxy[1,2,4]triazolo[4,3-b]pyridazin-3-yl)sulphanyl]-1,3-benzothiazol-2-yl}carbamate;
3-Methoxypropyl [6-({6-[(2-methoxyethyl)amino][1,2,4]triazolo[4,3-b]pyridazin-3-yl}sulphanyl)-1,3-benzothiazol-2-yl]carbamate;
1-[6-({6-[(2-Methoxyethyl)amino][1,2,4]triazolo[4,3-b]pyridazin-3-yl}sulphanyl)-1,3-benzothiazol-2-yl]-3-[2-(pyrrolidin-1-yl)ethyl]urea;
2-Methylpropan-2-yl (6-{[6-(4-chloro-2-hydroxybutoxy)[1,2,4]triazolo[4,3-b]pyridazin-3-yl]sulphanyl}-1,3-benzothiazol-2-yl)carbamate;
2-Methylpropan-2-yl [6-({6-[3-chloro-2-(hydroxymethyl)-2-methylpropoxy][1,2,4]triazolo[4,3-b]pyridazin-3-yl}sulphanyl)-1,3-benzothiazol-2-yl]carbamate;
6-{[6-(3-Fluorophenyl)-7,8-dihydro[1,2,4]triazolo[4,3-b]pyridazin-3-yl]sulphanyl}-1,3-benzothiazol-2-amine;
N-(6-{[6-(4-Fluorophenyl)[1,2,4]triazolo[4,3-b]pyridazin-3-yl]sulphanyl}-1,3-benzothiazol-2-yl)morpholine-4-carboxamide;
6-{[6-(2-Fluorophenyl)1,2,4]triazolo[4,3-b]pyridazin-3-yl]sulphanyl}-1,3-benzothiazol-2-amine;
N-(2-Methoxyethyl)-3-({2-[(2-methylbutyl)amino]-1,3-benzothiazol-6-yl}sulphanyl)[1,2,4]triazolo[4,3-b]pyridazin-6-amine;
N-{6-[(6-Ethoxy[1,2,4]triazolo[4,3-b]pyridazin-3-yl)sulphanyl]-1,3-benzothiazol-2-yl}-3-methoxypropanamide;
3-[(2-Amino-1,3-benzothiazol-6-yl)sulphanyl]-N-cyclohexyl[1,2,4]triazolo[4,3-b]pyridazin-6-amine;
6-{[6-(Cyclohexyloxy)[1,2,4]triazolo[4,3-b]pyridazin-3-yl]sulphanyl}-1,3-benzothiazol-2-amine;
N-(6-{[6-(3-Fluorophenyl)[1,2,4]triazolo[4,3-b]pyridazin-3-yl]sulphanyl}-1,3-benzothiazol-2-yl)acetamide;
N-(6-{[6-(4-Fluorophenyl)[1,2,4]triazolo[4,3-b]pyridazin-3-yl]sulphanyl}-1,3-benzothiazol-2-yl)-2-methylpropanamide;
N-(6-{[6-(3-Fluorophenyl)[1,2,4]triazolo[4,3-b]pyridazin-3-yl]sulphanyl}-1,3-benzothiazol-2-yl)cyclopropanecarboxamide and
6-{[6-(4-Fluorophenyl)-7,8-dihydro[1,2,4]triazolo[4,3-b]pyridazin-3-yl]sulphanyl}-N-(2-methylbutyl)-1,3-benzothiazol-2-amine or the addition salts with pharmaceutically acceptable mineral and organic acids or with pharmaceutically acceptable mineral and organic bases of said compounds.

18. A method of inhibiting MET protein kinase in a subject comprising administering to the subject a compound of formula (I):

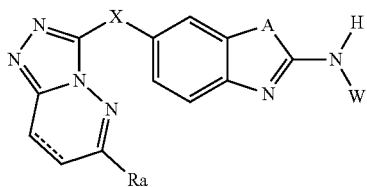

wherein:
- ⎓ represents a single or double bond;
- Ra represents a hydrogen atom; a halogen atom; an alkoxy radical optionally substituted with a chlorine atom, a hydroxyl radical or a heterocycloalkyl radical; an O-cycloalkyl radical; heteroaryl radical; a phenyl radical; an NHCOalk or NHCOcycloalk radical; or an NR1R2 radical;
- X represents S, SO or $SO_2$;
- A represents NH or S;
- W represents a hydrogen atom; an alkyl radical optionally substituted with alkoxy, heterocycloalkyl or NR3R4; or a COR radical in which R represents:
  - a cycloalkyl radical or an alkyl radical optionally substituted with an NR3R4, alkoxy, hydroxyl, phenyl, heteroaryl or heterocycloalkyl radical;
  - an alkoxy radical optionally substituted with NR3R4, alkoxy, hydroxyl or with heterocycloalkyl; an O-phenyl radical or an O—$(CH_2)_n$-phenyl radical, and n representing an integer from 1 to 4;
- or an NR1R2 radical; R1 and R2 are such that one of R1 and R2 represents a hydrogen atom or an alkyl radical and the other of R1 and R2 represents a hydrogen atom, a cycloalkyl radical or an alkyl radical optionally substituted with one or more radicals, which may be identical or different, chosen from hydroxyl, alkoxy, heteroaryl, heterocycloalkyl, NR3R4 and optionally substituted phenyl radicals, or else R1 and R2 form, with the nitrogen atom to which they are attached, a cyclic radical containing from 3 to 10 members and optionally one or more other heteroatoms chosen from O, S, N and NH;
- R3 and R4, which may be identical or different, represent a hydrogen atom or an alkyl radical, a cycloalkyl radical, a heteroaryl radical or a phenyl radical that is optionally substituted, or else R3 and R4 form, with the nitrogen atom to which they are attached, a cyclic radical containing from 3 to 10 members and optionally one or more other heteroatoms chosen from O, S, N, and NH;
- all the heterocycloalkyl, heteroaryl and phenyl radicals defined above and also the cyclic radicals that R1 and R2 or R3 and R4 can form with the nitrogen atom to which they are attached, being optionally substituted with one or more radicals chosen from halogen atoms, hydroxyl, oxo, alkoxy, $NH_2$, NHalk and $N(alk)_2$ radicals, alkyl, cycloalkyl, heterocycloalkyl, $CH_2$-heterocycloalkyl, phenyl, $CH_2$-phenyl, heteroaryl, CO-phenyl and S-heteroaryl radicals; wherein the alkyl, heterocycloalkyl, phenyl and heteroaryl radicals being themselves optionally substituted with one or more radicals chosen from halogen atoms and the radicals: hydroxyl, oxo, alkyl and alkoxy containing from 1 to 4 carbon atoms, $NH_2$, NHalk and $N(alk)_2$;
- wherein the term alkyl means a $C_1$ to $C_6$ alkyl group; the term alkoxy means a $C_1$ to $C_6$ alkoxy group; the term cycloalkyl means a saturated carbocyclic radical containing 3 to 10 carbon atoms; the term heterocycloalkyl means a mono or bicyclic carbocyclic radical containing from 3 to 10 members, interrupted with one or more heteroatoms, which may be the same or different chosen from oxygen, nitrogen or sulphur atoms; and the term heteroaryl means a monocyclic or bicyclic unsaturated or partially unsaturated heterocyclic radical containing at most 12 members, which may optionally contain a —C(O)— member and containing one or more heteroatoms which may be the same or different chosen from oxygen, nitrogen or sulphur atoms;
- or the addition salts with pharmaceutically acceptable mineral and organic acids or with pharmaceutically acceptable mineral and organic bases of said compounds.

* * * * *

UNITED STATES PATENT AND TRADEMARK OFFICE
CERTIFICATE OF CORRECTION

Page 1 of 2

PATENT NO.         : 9,115,134 B2
APPLICATION NO.    : 14/011110
DATED              : August 25, 2015
INVENTOR(S)        : Eva Albert et al.

It is certified that error appears in the above-identified patent and that said Letters Patent is hereby corrected as shown below:

On the Title Page, section "OTHER PUBLICATIONS", right-hand column, lines 23-25 of this column: please replace "N-(2-Chloro-6-Methylphenyl)-2-[[6-[4-(2-Hydroxyethyl)-1-Piperazinyl)]-2-Methyl-4-Pyrimidinyl] Amino)]-1,3-Thiazole-5-Carboxamide" with --N-(2-Chloro-6-Methylphenyl)-2-[[6-[4-(2-Hydroxyethyl)-1-Piperazinyl)]-2-Methyl-4-Pyrimidinyl]Amino)]-1,3-Thiazole-5-Carboxamide--.

In the Claims:
At column 95, claim number 1, line 8: please replace:
"or an NR1R2 radical; R1 and R2 are such that" with
--or an NR1R2 radical;
R1 and R2 are such that--;

At column 97, claim number 4, line 29: please replace "a hydrogen atom a halogen atom" with --a hydrogen atom, a halogen atom--;

At column 97, claim number 4, line 39: please replace "or;" with --or--;

At column 98, claim number 6, line 59: please delete "radical";

Signed and Sealed this
Seventeenth Day of May, 2016

Michelle K. Lee
*Director of the United States Patent and Trademark Office*

CERTIFICATE OF CORRECTION (continued)
U.S. Pat. No. 9,115,134 B2

In the Claims:

At column 101, claim number 16, line 45: please replace:

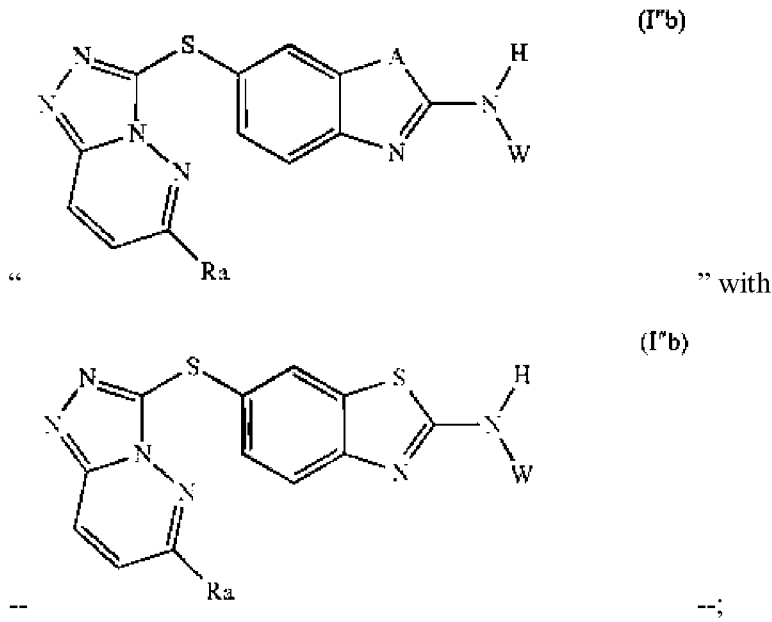

" " with " ";

At column 102, claim number 17, lines 62-64: please replace:

"N-{6-[(6-methoxy[1,2,4]triazolo[4,3-b]pyridazin-3-yl)
   sulphanyl]-1,3-benzothiazol-2-
   yl}cyclopropanecarboxamide;"

with

--N-{6-[(6-methoxy[1,2,4]triazolo[4,3-b]pyridazin-3-yl)
   sulphanyl]-1,3-benzothiazol-2-yl}cyclopropanecarboxamide;--

At column 104, claim number 17, lines 34-35: please replace "6-{[6-(2-Fluorophenyl)1,2,4]triazolo[4,3-b]pyridazin-3-yl]sulphanyl}-1,3-benzothiazol-2-amine;" with --6-{[6-(2-Fluorophenyl)[1,2,4]triazolo[4,3-b]pyridazin-3-yl]sulphanyl}-1,3-benzothiazol-2-amine;--; and At column 105, claim number 18, line 33: please replace:

"or an NR1R2 radical; R1 and R2 are such that" with

--or an NR1R2 radical;
R1 and R2 are such that--.